United States Patent
Sircar et al.

(10) Patent No.: US 6,521,666 B1
(45) Date of Patent: Feb. 18, 2003

(54) INHIBITORS OF α4 MEDIATED CELL ADHESION

(75) Inventors: Ila Sircar, San Diego, CA (US); Kristjan S. Gudmundsson, Raleigh, NC (US); Richard Martin, San Diego, CA (US)

(73) Assignee: Tanabe Seiyaku Co., Ltd., Osaka (JP)

(*) Notice: Subject to any disclaimer, the term of this patent is extended or adjusted under 35 U.S.C. 154(b) by 0 days.

(21) Appl. No.: 09/619,712

(22) Filed: Jul. 19, 2000

Related U.S. Application Data

(63) Continuation of application No. PCT/US99/00993, filed on Jan. 19, 1999.
(60) Provisional application No. 60/071,840, filed on Jan. 20, 1998.

(51) Int. Cl.$^7$ .................... C07C 233/87; A61K 31/245; A61P 43/00
(52) U.S. Cl. ........................... 514/576; 562/445
(58) Field of Search ................ 514/576; 562/445

(56) References Cited

U.S. PATENT DOCUMENTS 6,191,171 B1   2/2001   DeLaszlo et al.

FOREIGN PATENT DOCUMENTS

| WO | WO9512611 A1 | 5/1995 |
|---|---|---|
| WO | WO9526360 A1 | 10/1995 |
| WO | WO9622966 | 8/1996 |
| WO | WO9633170 A1 | 10/1996 |
| WO | WO9853814 A1 | 12/1998 |
| WO | WO9853817 A1 | 12/1998 |
| WO | WO9853818 A1 | 12/1998 |
| WO | WO9854207 A1 | 12/1998 |
| WO | WO9858902 | 12/1998 |
| WO | WO9906390 A1 | 2/1999 |
| WO | WO9906431 A1 | 2/1999 |
| WO | WO9906432 A1 | 2/1999 |
| WO | WO9906433 A1 | 2/1999 |
| WO | WO9906434 A1 | 2/1999 |
| WO | WO9906435 A1 | 2/1999 |
| WO | WO9906436 A1 | 2/1999 |
| WO | WO9906437 A1 | 2/1999 |
| WO | WO9910312 A1 | 3/1999 |
| WO | WO9910313 A1 | 3/1999 |
| WO | WO9926615 A1 | 6/1999 |
| WO | WO9926921 A1 | 6/1999 |
| WO | WO9926922 A1 | 6/1999 |
| WO | WO9935163 A1 | 7/1999 |
| WO | WO9937618 A1 | 7/1999 |
| WO | WO9943642 A1 | 9/1999 |
| WO | WO9948879 A1 | 9/1999 |
| WO | WO9961465 A1 | 12/1999 |
| WO | WO9964390 A1 | 12/1999 |
| WO | WO9964395 A1 | 12/1999 |
| WO | WO9967230 A1 | 12/1999 |
| WO | WO0037429 A2 | 6/2000 |

OTHER PUBLICATIONS

Shroff et al., *Bioorganic & Medicinal Chemistry Letters*, vol. 6, No. 21, pp. 2495–2500 (1996).
Viney et al., *The Journal of Immunology*, vol. 157, pp. 2488–2497 (1996).
Briskin et al., *J. Immunol.*, vol. 156, pp. 719–726 (1996).
Chemical Abstracts, vol. 65, No. 10, Abstract No. 15302d (1966).

*Primary Examiner*—Ceila Chang
*Assistant Examiner*—Andrea D. Small
(74) *Attorney, Agent, or Firm*—Birch, Stewart, Kolasch & Birch, LLP

(57) ABSTRACT

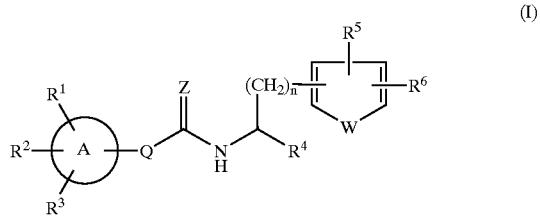

The present invention relates to a pharmaceutical composition comprising as an active ingredient a compound of formula (I), wherein Ring A is an aromatic or a heterocyclic ring; Q is a bond, carbonyl, lower alkylene, lower alkenylene, —O-(lower alkylene)-, etc.; n is 0, 1 or 2; Z is oxygen or sulfur, W is oxygen, sulfur, —CH═CH—, —NH— or —N═CH—; $R^1$, $R^2$ and $R^3$ are the same or different and are hydrogen, halogen, hydroxyl, a substituted or unsubstituted lower alkyl group, a substituted or unsubstituted lower alkoxy group, a substituted or unsubstituted amino group, etc.; $R^4$ is tetrazolyl, carboxyl group, amide or ester; $R^5$ is hydrogen, nitro, amino, hydroxyl, lower alkanoyl, lower alkyl etc.; $R^6$ is selected from (a) a substituted or unsubstituted phenyl group, (b) a substituted or unsubstituted pyridyl group, (c) a substituted or unsubstituted thienyl group, (d) a substituted or unsubstituted benzofuranyl group, etc.; or a pharmaceutically acceptable salt thereof.

42 Claims, No Drawings

INHIBITORS OF α4 MEDIATED CELL ADHESION

This application is a con of PCT/US99/00993 Jan. 19, 1999 and claims benefit of No. 60/071,840 Jan. 20, 1998.

BACKGROUND OF THE INVENTION

1. Field of the Invention

The present invention relates to pharmaceutical compositions comprising molecules that are inhibitors of α4 mediated (including α4β7) adhesion and which could be useful in treating conditions such as asthma, diabetes, rheumatoid arthritis, inflammatory bowel disease and other diseases involving leukocyte infiltration of the gastrointestinal tract or other epithelial lined tissues; such as, skin, urinary tract, respiratory airway and joint synovium.

The inhibitors of the present invention could also be useful in treating conditions involving leukocyte infiltration of other tissues including lung, blood vessels, heart and nervous system as well as transplanted organs such as kidney, liver, pancreas and heart.

2. Description of the Related Art

The adhesion of leukocyte to endothelial cells or extracellular matrix proteins is a fundamental process for immunity and inflammation and involves multiple adhesive interactions. The earliest events in this process include leukocyte rolling followed by changes in integrin avidity, which leads to subsequent firm adhesion (for reviews see Butcher, Cell 67:1033–1036 (1991); Harlan, Blood 3:513–525 (1985); Hemler, Annu. Rev. Immunol. 8:365–400 (1990); Osborn, Cell 62:3–6 (1990); Shimizu et al., Immunol. Rev. 114:109–143 (1990); Springer, Nature 346:425–434 (1990); Springer, Cell 76:301–314 (1994)). In response to chemotactic factors, the leukocytes must migrate through two adjacent endothelial cells and into tissues that are composed, in part, of the extracellular matrix protein fibronectin (FN) (see Wayner et al., J. Cell Biol. 105:1873–1884 (1987)) and collagen (CN) (see Bornstein et al., Ann. Rev. Biochem. 49:957–1003 (1980) and Miller, Chemistry of the collagens and their distribution. In Connective Tissue Biochemistry. K. A. Piez and A. H. Reddi, editors. Elsevier, Amsterdam. 41–78. (1983)) Important recognition molecules that participate in these reactions belong to the integrin gene superfamily (for reviews see Hemler, Annu. Rev. Immunol. 8:365–400 (1990); Hynes, Cell 48:549–554 (1987); Shimizu et al., Immunol. Rev. 114:109–143 (1990); and Springer, Nature 346:425–434 (1990)).

Integrins are composed of non-covalently associated subunits, referred to as the alpha (α) and beta (β) subunits (for reviews see Hemler, Annu. Rev. Immunol. 8:365–400 (1990); Hynes, Cell 48:549–554 (1987); Shimizu et al., Immunol. Rev. 114:109–143 (1990); and Springer, Nature 346:425–434 (1990)). To date, 8 integrin β subunits have been identified which can associate with 16 distinct α subunits to form 22 distinct integrins. The β7 integrin subunit, first cloned by Erle et al., (Erle et al., J. Biol. Chem. 266:11009–11016 (1991)) is expressed only on leukocytes and is known to associate with two distinct α subunits, α4 (Ruegg et al., J. Cell Biol. 117:179–189 (1992)) and αE (Cerf-Bensussan et al., Eur. J. Immunol. 22:273–277 (1992) and Kilshaw et al., Eur. J. Immunol. as its sole ligand.

The α4β7 complex has three known ligands (VCAM, CS-1, MAdCAM). One ligand which shows unique specificity for α4β7 is Mucosal Addressing Cell Adhesion Molecule (MAdCAM) (see Andrew et al., J. Immunol 153:3847–3861 (1994); Briskin et al., Nature 363:461–464 (1993); and Shyjan et al., J. Immunol 156:2851–2857 (1996)). MAdCAM is highly expressed on Peyer's patch high endothelial venules, in mesenteric lymph nodes, and on gut lamina propria and mammary gland venules (Berg et al., Immunol. Rev. 105:5 (1989)). Integrin α4β7 and MAdCAM have been shown to be important in regulating lymphocyte trafficking to normal intestine (Holzmann et al., Cell 56:37 (1989)).

The second ligand for α4β7 is connecting segment 1 (CS-1), an alternatively spliced region of the FN A chain (see Guan et al., Cell 60:53–61 (1990) and Wayner et al., J. Cell Biol. 109:1321–1330 (1989)). The cell-binding site within this alternatively spliced region is composed of 25 amino acids where the carboxy terminal amino acid residues, EILDVPST, form the recognition motif (see Komoriya et al., J. Biol. Chem. 266:15075–15079 (1991) and Wayner et al., J. Cell Biol. 116:489–497 (1992)).

The third ligand for α4β7 is vascular cell adhesion molecule 1 (VCAM-1), a cytokine inducible protein expressed on endothelial cells (see Elices et al., Cell 60:577–584 (1990) and Ruegg et al., J. Cell Biol. 117:179–189 (1992)). VCAM and CS-1 (see Elices et al., Cell 60:577–584 (1990)) are two ligands which are shared by α4β7 and α4β1. It remains to be unequivocally shown whether MAdCAM, VCAM and CS-1 bind to the same site on α4β7. Using a panel of monoclonal antibodies, Andrew et al., showed that α4β7 interaction with its three ligands involve distinct but overlapping epitopes (Andrew et al., J. Immunol 153:3847–3861 (1994)).

UTILITY OF THE INVENTION

A number of in vitro and in vivo studies indicate that α4 plays a critical role in the pathogenesis of a variety of diseases. Monoclonal antibodies directed against α4 have been tested in a variety of disease models. Efficacy of anti-α4 antibody was demonstrated in a rat and mouse model of experimental autoimmune encephalomyelitis (see Baron et al., J. Exp. Med. 177:57–68 (1993) and Yednock et al., Nature 356:63–66 (1992)). A significant number of studies have been done to evaluate the role of α4 in allergic airways (see Abraham et al., J. Clin. Invest. 93:776–787 (1994); Bochner et al., J. Exp. Med. 173:1553–1556 (1991); Walsh et al., J. Immunol 146:3419–3423 (1991); and Weg et al., J. Exp. Med. 177:561–566 (1993)). For example, monoclonal antibodies to α4 were effective in several lung antigen challenge models (see Abraham et al., J. Clin. Invest. 93:776–787 (1994) and Weg et al., J. Exp. Med. 177:561–566 (1993)). Interestingly, blockade of cellular recruitment is not seen in certain lung models even though there is abrogation of the late phase response (see Abraham et al., J. Clin. Invest. 93:776–787 (1994)). The cotton-top tamarin, which experiences spontaneous chronic colitis, showed a significant attenuation of colitis when anti-α4 antibody was administered (see Bell et al., J. Immunol. 151:4790–4802 (1993) and Podolsky et al., J. Clin. Invest. 92:372–380 (1993)). Monoclonal antibody to α4 inhibits insulitis and delays the onset of diabetes in the non-obese diabetic mouse (see Baron et al., J. Clin. Invest. 93:1700–1708 (1994); Burkly et al., i Diabetes 43:529–534 (1994); and Yang et al., Proc. Natl. Acad. Sci. USA 90:10494–10498 (1993)). Other diseases where α4 has been implicated include rheumatoid arthritis (see Laffon et al., J. Clin. Invest. 88:546–552 (1991) and Morales-Ducret et al., J. Immunol. 149:1424–1431 (1992)) and atherosclerosis (see Cybulsky et al., Science 251:788–791 (1991)). Delayed type hypersensitivity reaction (see Issekutz, J. Immunol.

147:4178–4184 (1991)) and contact hypersensitivity response (see Chisholm et al., *Eur. J. Immunol.* 23:682–688 (1993) and Ferguson et al., *J. Immunol.* 150:1172–1182 (1993)) are also blocked by anti-α4 antibodies. For an excellent review of in vivo studies implicating α4 in disease (see Lobb et al., *J. Clin. Invest.* 94:1722–1728 (1995)).

Although these studies clearly implicate α4 in a variety of diseases, it is not clear whether the inhibition seen was due to blocking α4β1, α4β7, or both. Recently, several studies have addressed this issue using an antibody which recognizes the α4β7 complex (see Hesterberg et al., *Gastroenterology* (1997)), antibodies against β7 or antibodies directed against MAdCAM (see Picarella et al., *J. Immunol.* 158:2099–2106 (1997)), for which α4β1 does not bind. In the primate model of inflammatory bowel disease, it was shown that antibodies to the α4β7 complex ameliorated inflammation and decreased diarrhea (see Hesterberg et al., Gastroenterology, *111:1373–1380* (1996)). In a second model, monoclonal antibodies to β7 or MAdCAM blocked recruitment of lymphocytes to the colon and reduced the severity of inflammation in the colon of scid mice reconstituted with CD45RB$^{high}$ CD4$^+$ cells (see Picarella et al., *J. Immunol.* 158:2099–2106 (1997)). This, together with the fact that gut-associated lymphoid tissue is severely impaired in β7 knock out mice, suggests that α4β7 may be an important intervention point for inflammatory bowel disease.

The expression of α4β7 on a variety of leukocytes and the increase in α4β7 positive cells in diseased tissues implicates that the receptor may play an important role in cellular recruitment to other sites of inflammation in addition to trafficking to the gut. CD4$^+$, CD8$^+$ T-cells, B-cells, NK cells, and eosinophils from human peripheral blood were shown to express high levels of α4β7 (see Picarella et al., *J. Immunol.* 158:2099–2106 (1997)). Increased numbers of α4β7+ T-cells were found in the synovial membrane of rheumatoid arthritis patients and it was predicted that the augmented expression of α4β7 may contribute to the development and perpetuation of this disease (see Lazarovits et al., *J. Immunol.* 151:6482–6489 (1993)). In the nonobese diabetic mouse, MAdCAM was expressed on high endothelial venules in inflamed islets within the pancreas suggesting a role for α4β7 in diabetes (see Kelner et al., *Science* 266:1395–1399 (1994)). The distribution of α4β7 on lymphocytes and eosinophils (see Erle et al., *J. Immunol.* 153:517–528 (1994)), together with in vitro studies showing that α4β7mediates human eosinophil adhesion to VCAM, CS-1 and MAdCAM (see Walsh et al., (Immunology 89:112–119, 1996), suggests that this integrin may be a target molecule in asthma. Collectively, these data suggest that integrin α4β7 may play an important role in a variety of inflammatory diseases.

N-terminal domain (domain 1) of MAdCAM has homology to the N-terminal integrin recognition domains in both VCAM and ICAM (see Briskin et al., *Nature* 363:461–464 (1993)). Using site-directed mutagenesis on MAdCAM, the binding motif was identified in the first domain as three linear amino acid residues within a C-D loop (see Viney et al., *J. Immunol.* 157:2488–2497 (1996)). Mutations of L40, D41 and T42 resulted in a complete loss of binding activity to α4β7, suggesting that LDT on MADCAM is involved in binding loop (see Viney et al., *J. Immunol.* 157:2488–2497 (1996)). Alignment of this region on MAdCAM with other integrin ligands such as VCAM or CS-1 reveals that there is a conserved binding motif or consensus sequence, consisting of G/Q I/L E/D T/S and P/S residues (see Briskin et al., *J. Immunol.* 156:719–726 (1996)). Further support comes from the fact that linear and cyclic peptides containing LDT were shown to block cell adhesion to MAdCAM in vitro (see Shroff et al., *Bioorganic & Medicinal Chemistry Letters* 6:2495–2500 (1996) and Viney et al., *J. Immunol.* 157:2488–2497 (1996)).

The use of monoclonal antibodies against integrins in vivo has demonstrated that a number of integrins are indeed valid therapeutic targets for inflammatory and cardiovascular diseases and in organ transplantation. The objective here was to define an orally bioavailable, non-peptide, small molecule antagonist of α4β7. Small molecules that are potent inhibitors of α4β7 mediated adhesion to either MAdCAM, VCAM, or CS-1 and which could be useful for the treatment of inflammatory disease are disclosed.

ABBREVIATIONS

BOP-C1: Bis(2-oxo-3-oxazolidinyl)phosphinic chloride
BOP reagent: Benzotriazol-1-yloxy-tris(dimethylamino) phosphonium hexafluorophosphate
DCC: 1,3-Dicyclohexylcarbodiimide
EDC: 1-Ethyl-3-(3-dimethylaminopropyl)carbodiimide
THF: Tetrahydrofuran
DMF: N,N-Dimethylformamide
DIEA: Diisopropylethylamine
DMAP: 4-(N,N-Dimethylamino)pyridine
DBU: 1,8-Diazabicyclo[5.4.0]undec-7-ene
CDI: Carbonyldiimidazole
HOBT: 1-Hydroxybenzotriazole
Boc: tert-Butoxycarbonyl
Tf$_2$O: Triflic anhydride
Tf: Trifluoromethanesulfonyl
TFA: Trifluoroacetic acid
DME: 1,2-Dimethoxyethane
MsCl: Methanesulfonyl chloride
DIAD: Diisopropyl azodicarboxylate
Ac: Acetyl
Me: Methyl
Et: Ethyl
Ph: Phenyl
Bn: Benzyl
EtOAc: Ethyl acetate (=AcOEt)
mCPBA: m-Chloroperbenzoic acid
TMS: Trimethylsilyl
h: hour(s)
min: minute(s)
satd: Saturated Additionally, several phrases are utilized for which specific meanings and interpretations exist. These are as follows:

The use of "lower" preceding a group such as alkyl, alkoxy, alkylene or alkane are meant to encompass 1 to 6 carbon atoms either in a straight chain or in a branched chain and the use of "lower" preceding alkanoyl, alkenyl, or alkenylene are meant to encompass 2 to 7 carbon atoms either in a straight chain or in a branched chain. The use of "lower" preceding cycloalkyl or cycloalkoxy are meant to encompass 3 to 7 carbon atoms.

The use of phrases such as "morpholino-lower alkyl", "hydroxy-lower alkoxy" and the like are meant to refer to groups wherein the functional group preceding the hyphen is a substituent of the functional group that follows the hyphen. For example, "hydroxy-lower alkoxy" would refer to a lower alkoxy group containing at least one hydroxy substituent.

The use of phrases such as "a lower alkyl group substituted by a halogen atom", "phenyl group substituted by a lower alkoxy group" and the like are meant to refer to functional groups containing at least one substituent. For example, "a lower alkyl group substituted by a halogen atom" would refer to a lower alkyl group containing at least one halogen atom, and "phenyl group substituted by a lower alkoxy group" would refer to at least one lower alkoxy group. This type of phraseology is meant to be interpreted by one of skill in the art, therefore, any deviations and combinations of this type of nomenclature is also within the abilities of those skilled in the art to interpret. Accordingly, this type of nomenclature is not to be applied to combinations that would not result in a realistic type of molecule or substituent.

SUMMARY OF THE INVENTION

The present invention relates to a pharmaceutical composition comprising therapeutically effective amount of a compound of the formula [I]:

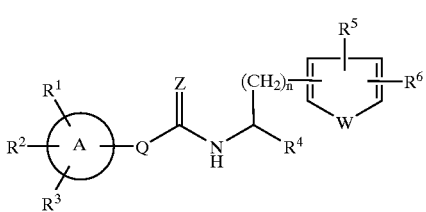

wherein
Ring A is an aromatic hydrocarbon ring or a heterocyclic ring;
Q is a bond, a carbonyl group, a lower alkylene group which may be substituted by a hydroxyl group or phenyl group, a lower alkenylene group, or a —O-(lower alkylene)-group;
n is an integer of 0, 1 or 2;
W is oxygen atom, sulfur atom, a —CH=CH— group or a —N=CH— group;
Z is oxygen atom or sulfur atom;
$R^1$, $R^2$, $R^3$ are the same or different and are selected from the group consisting of:
  a) hydrogen atom,
  b) a halogen atom,
  c) a substituted or unsubstituted lower alkyl group,
  d) a substituted or unsubstituted lower alkoxy group,
  e) a nitro group,
  f) a substituted or unsubstituted amino group,
  g) a carboxyl group or an amide or an ester thereof,
  h) a cyano group,
  i) a lower alkylthio group,
  j) a lower alkanesulfonyl group,
  k) a substituted or unsubstituted sulfamoyl group,
  l) a substituted or unsubstituted aryl group,
  m) a substituted or unsubstituted heterocyclic group, and
  n) hydroxyl group;
or two of $R^1$, $R^2$ and $R^3$ may combine each other at the terminal thereof to form a lower alkylenedioxy group;
$R^4$ is tetrazolyl group, a carboxyl group, or an amide or an ester thereof;
$R^5$ is a group selected from the group consisting of:
  a) a hydrogen atom,
  b) a nitro group,
  c) a substituted or unsubstituted amino group,
  d) a hydroxyl group,
  e) a lower alkanoyl group,
  f) a substituted or unsubstituted lower alkyl group,
  g) a lower alkoxy group,
  h) a halogen atom, and
  i) 2-oxopyrrolidinyl group;
$R^6$ is a group selected from the group consisting of:
  a) a substituted or unsubstituted phenyl group, and
  b) a substituted or unsubstituted heteroaryl group; or a pharmaceutically acceptable salt thereof.

The present invention also relates to a method for treating or preventing conditions caused by α4 (including α4β7 and α4β1) mediated cell adhesion which comprises administering a compound of the formula [I].

Further, the present invention also relates to a novel compound, which is a compound of the formula [I] with the proviso that when Ring A is a benzene ring, it is not substituted with methyl group in the 3- and the 5-positions or in the 2- and the 4-positions; or a pharmaceutically acceptable salt thereof.

DETAILED DESCRIPTION OF THE INVENTION

The novel compound of the present invention may exist in the form of optical isomers based on asymmetric carbon atoms thereof, and the present invention also includes these optical isomers and mixtures thereof.

In an embodiment of the present invention, the steric configuration of the compound need not be fixed. The compound of the present invention may be a compound with a sole configuration or a mixture thereof with several different configurations.

In the above formula (I), "aromatic hydrocarbon ring" may be a mono-, bi- or tri-cyclic aromatic hydrocarbon ring such as a benzene ring, a naphthalene ring, an anthracene ring, a fluorene ring.

In the above formula (I), "heterocyclic ring" may be a heteroatom-containing mono-, bi- or tri-cyclic ring. Examples of "heterocyclic ring" may be pyridine ring, pyrimidine ring, pyridazine ring, pyrazine ring, quinoline ring, isoquinoline ring, quinazoline ring, phthalazine ring, imidazole ring, isoxazole ring, pyrazole ring, oxazole ring, thiazole ring, indole ring, benzazole ring, benzothiazole ring, benzimidazole ring, benzofuran ring, furan ring, thiophene ring, pyrrole ring, oxadiazole ring, thiadiazole ring, triazole ring, tetrazole ring, pyrrole ring, indoline ring, indazole ring, isoindole ring, purine ring, morpholine ring, quinoxaline ring, benzothiophene ring, pyrrolidine ring, benzofurazane ring, benzothiadiazole ring, thiazolidine ring, imidazothiazole ring, dibenzofuran ring, and isothiazole ring.

In the above formula (I), "aryl group" may be a mono-, bi- or tri-cyclic aromatic group. Examples of "aryl group" may be a phenyl group, a naphthyl group, an anthryl group and a fluorenyl ring.

In the above formula (I), "heterocyclic group" may be a mono-, bi- or tri-cyclic ring containing a heteroatom such as nitrogen atom, oxygen atom, and sulfur atom. Examples of "heterocyclic group" may be pyridyl group, pyrimidinyl group, pyridazinyl group, pyrazinyl group, quinolyl group, isoquinolyl group, quinazolinyl group, phthalazinyl group, imidazolyl group, isoxazolyl group, pyrazolyl group, oxazolyl group, thiazolyl group, indolyl group, benzazolyl group, benzothiazolyl group, benzimidazolyl group, benzofuranyl group, furyl group, thienyl group, pyrrolyl group, oxadiazolyl group, thiadiazolyl group, triazolyl group, tetrazolyl group, pyrrolyl group, indolinyl group, indazolyl group, isoindolyl group, purinyl group, morpholinyl group, quinoxalinyl group, benzothienyl group, pyrrolidinyl group, benzofurazanyl group, benzothiadiazolyl group, thiazolidinyl group, imidazothiazolyl group, dibenzofuranyl group, isothiazolyl group, pyrrolinyl group, piperidinyl group, piperazinyl group, and tetrahydropyranyl group.

In the above formula (I), "heteroaryl group" may be a mono-, bi- or tri-cyclic aromatic group containing a heteroatom such as nitrogen atom, oxygen atom, and sulfur atom. Examples of "heteroaryl group" may be a "heterocyclic ring" other than pyrrolidinyl group, pyrrolinyl group, piperidinyl group, piperazinyl group, morpholinyl group, and tetrahydropyranyl group. Preferable examples of the "heteroaryl group" may be pyridyl group, thienyl group, benzofuranyl group, pyrimidyl group, and isoxazolyl group.

The novel compound among the compound [I] of the present invention is indicated as follows:

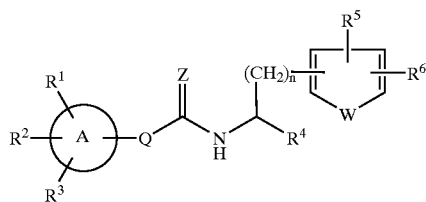

[I]

wherein
Ring A is an aromatic hydrocarbon ring or a heterocyclic ring;
Q is a bond, a carbonyl group, a lower alkylene group which may be substituted by a hydroxyl group or phenyl group, a lower alkenylene group, or a —O-(lower alkylene)-group;
n is an integer of 0, 1 or 2;
W is oxygen atom, sulfur atom, a —CH=CH— group or a —N=CH— group;
Z is oxygen atom or sulfur atom;
$R^1$, $R^2$ and $R^3$ are the same or different and are selected from the group consisting of:
  a) hydrogen atom,
  b) a halogen atom,
  c) a substituted or unsubstituted lower alkyl group,
  d) a substituted or unsubstituted lower alkoxy group,
  e) a nitro group,
  f) a substituted or unsubstituted amino group,
  g) a carboxyl group or an amide or an ester thereof,
  h) a cyano group,
  i) a lower alkylthio group,
  j) a lower alkanesulfonyl group,
  k) a substituted or unsubstituted sulfamoyl group,
  l) a substituted or unsubstituted aryl group,
  m) a substituted or unsubstituted heterocyclic group, and
  n) hydroxyl group;
  or two of $R^1$, $R^2$ and $R^3$ may combine each other at the terminal thereof to form a lower alkylenedioxy group;
$R^4$ is tetrazolyl group, a carboxyl group, or an amide or an ester thereof;
$R^5$ is a group selected from the group consisting of:
  a) a hydrogen atom,
  b) a nitro group,
  c) a substituted or unsubstituted amino group,
  d) a hydroxyl group,
  e) a lower alkanoyl group,
  f) a substituted or unsubstituted lower alkyl group,
  g) a lower alkoxy group,
  h) a halogen atom, and
  j) 2-oxopyrrolidinyl group;
$R^6$ is a group selected from the group consisting of:
  a) a substituted or unsubstituted phenyl group,
  b) a substituted or unsubstituted heteroaryl group;
with the proviso that when Ring A is a benzene ring, the ring is not substituted with methyl group in the 3- and the 5-positions or in the 2- and the 4-positions; or a pharmaceutically acceptable salt thereof.

A preferred configuration of the active ingredient of the present invention is represented by the formula [I-A]:

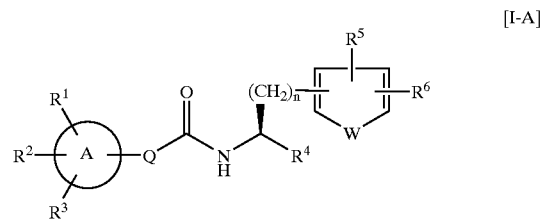

[I-A]

wherein symbols are the same as defined above.

A preferred embodiment of the present invention is the compound [I] with the additional proviso that when Ring A is a benzene ring, the ring is substituted in at least one of 2- and 6-positions.

Another preferred embodiment of the present invention is the compound (I) wherein $R^1$, $R^2$ and $R^3$ are selected from the group consisting of:
  a) hydrogen atom,
  b) a halogen atom,
  c) a substituted or unsubstituted lower alkoxy group,
  d) a nitro group,
  e) a substituted or unsubstituted amino group,
  f) a carboxyl group or an amide or an ester thereof,
  g) a cyano group,
  h) a lower alkylthio group,
  i) a lower alkanesulfonyl group,
  j) a substituted or unsubstituted sulfamoyl group,
  k) a substituted or unsubstituted aryl group,
  l) a substituted or unsubstituted heterocyclic group, and
  m) hydroxyl group, or two of $R^1$, $R^2$ and $R^3$ may combine with each other at the terminal thereof to form a lower alkylenedioxy group.

A more preferred configuration of the active ingredient of the present invention is represented by the formula [I-B]:

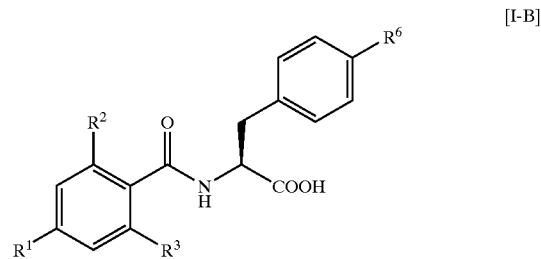

[I-B]

wherein symbols are the same as defined above.

In more preferred embodiment of the present invention, $R^1$ is hydrogen atom, a halogen atom, carboxyl group, carbamoyl group, nitro group, a substituted or unsubstituted amino group, a substituted or unsubstituted heterocyclic ring;

$R^2$ is hydrogen atom, a lower alkyl group or a halogen atom;

$R^3$ is hydrogen atom, a lower alkyl group or a halogen atom;

$R^6$ is a phenyl group which may be substituted at 2-, 4-, and/or 6-position of the phenyl group by a group selected from the group consisting of:
1) a halogen atom,
2) a substituted or unsubstituted lower alkoxy group,
3) a substituted or unsubstituted lower alkyl group,
4) a substituted or unsubstituted amino group,
5) a substituted or unsubstituted carbamoyl group, and
6) a substituted or unsubstituted sulfamoyl group.

In further preferred embodiment of the present invention, $R^6$ is a phenyl group which may be substituted by a group selected from the group consisting of:
1) a lower alkoxy group, and
2) a lower alkyl group which may be substituted by a group selected from a substituted or unsubstituted amino group, a substituted or unsubstituted piperidinyl group, a substituted or unsubstituted morpholino group, a substituted or unsubstituted piperazinyl group, a substituted or unsubstituted pyrrolidinyl group, and a substituted or unsubstituted imidazolidinyl group.

In another embodiment of the present invention,

Ring A is a benzene ring, a pyridine ring, a pyrazine ring, a furan ring, an isoxazole ring, a benzofuran ring, a thiophene ring, a pyrrole ring, or an indole ring;

$R^1$, $R^2$ and $R^3$ are selected from the group consisting of:
a) hydrogen atom,
b) a halogen atom,
c) a lower alkyl group which may be substituted by a halogen atom or a (halogenobenzoyl)amino group,
d) a lower alkoxy group which may be substituted by a halogen atom,
e) a nitro group,
f) an amino group which may be substituted by 1–2 groups selected from the group consisting of 1) a lower alkyl group, 2) a lower alkanoyl group, 3) a halogenobenzoyl group, 4) a lower alkoxycarbonyl group, 5) a lower alkanesulfonyl group which may be substituted by a halogen atom, 6) a benzenesulfonyl group which may be substituted by a lower alkyl group, a trihalogeno-lower alkyl group, a halogen atom or a lower alkoxy group, 7) thiophenesulfonyl group, 8) a carbamoyl group which may be substituted by a lower alkyl group, a lower alkyl-phenyl group, 9) a thiocarbamoyl group which may be substituted by a lower alkyl group, phenyl group, a phenyl-lower alkyl group, 10) thiazolinyl group, and 11) a sulfamoyl group which may be substituted by a lower alkyl group;
g) a carboxyl group,
h) a carbamoyl group which may be substituted by a lower alkanesulfonyl group,
i) a lower alkoxycarbonyl group,
j) a cyano group,
k) a lower alkylthio group,
l) a lower alkanesulfonyl group,
m) a sulfamoyl group,
n) a phenyl group,
o) a pyrrolidinyl group which may be substituted by oxo group,
p) a pyrrolyl group which may be substituted by a group selected from the group consisting of 1) a lower alkanoyl group which may be substituted by a halogen atom, 2) a halogen atom, 3) formyl group, and 4) a lower alkyl group which may be substituted by hydroxy group,
q) a thienyl group,
r) an isoxazolyl group which may be substituted by a lower alkyl group,
s) a thiazolyl group,
t) a pyrazolyl group,
u) a pyrazinyl group,
v) a pyridyl group, and
w) hydroxyl group;

$R^4$ is selected from the group consisting of:
a) carboxyl group,
b) a lower alkoxycarbonyl group which may be substituted by 1) pyridyl group or 2) an amino group which may be substituted by a lower alkyl group,
c) a lower cycloalkoxy carbonyl group,
d) a carbamoyl group which may be substituted by a hydroxy group or a lower alkanesulfonyl group, and
e) a tetrazolyl group;

$R^5$ is selected from the group consisting of:
a) a hydrogen atom,
b) a nitro group,
c) an amino group which may be substituted by a lower alkanoyl group, a lower alkoxycarbonyl group or a lower alkanesulfonyl group,
d) a hydroxyl group,
e) a lower alkanoyl group,
f) a lower alkyl group which may be substituted by 1) hydroxyl group, or 2) an imino group which is substituted by hydroxyl group or a lower alkoxy group,
g) a lower alkoxy group,
h) a halogen atom,
i) 2-oxopyrrolidinyl group;

$R^6$ is the group selected from the group consisting of:
a) a phenyl group which may have 1–5 substituents selected from the group consisting of:
1) a halogen atom,
2) a nitro group,
3) a formyl group,
4) a hydroxyl group,
5) a carboxyl group,
6) a lower alkoxy group which may be substituted by a group selected from the group consisting of i) a carboxyl group or an amide or an ester thereof, ii) hydroxyl group, iii) a cyano group, iv) a halogen atom, v) an amino group which may be substituted by a lower alkyl group, vi) a pyridyl group, vii) a thiazolyl group which may be substituted by a lower alkyl group, viii) an isoxazolyl group which may be substituted by a lower alkyl group, ix) a piperidyl group which may be substituted by a lower alkyl group, x) a pyrrolidinyl group which may be substituted by a lower alkyl group, xi) a phenyl group which may be substituted by a halogen atom, xii) a furyl group, xiii) a thienyl group, and xiv) a lower alkoxy group
7) a lower alkyl group which may be substituted by a group selected from the group consisting of i) a halogen atom, ii) hydroxyl group, iii) carboxyl group or an amide or an ester thereof, iv) a lower alkoxy group, v) an amino group which may be substituted by 1–2 groups selected from the group consisting of a lower alkyl group, a hydroxy-lower alkyl group, a (lower alkylamino)-lower alkyl group, phenyl-lower alkyl group, a phenyl group, and a pyridyl group, vi) a piperidinyl group which may be substituted by a lower alkylenedioxy group, an oxo group or a hydroxy group, vii) a morpholino group which may be substituted by a lower alkyl group, viii) thiomorpholino group which may be oxidized, ix) piperazinyl group which may be substituted by a lower alkyl group, a hydroxy-lower alkyl group, a lower alkanoyl group or a phenyl-lower alkyl group, x) pyrrolidinyl group which may be substituted by oxo group, and xi) a imidazolidine group which may be substituted by 1–3 groups selected from the group consisting of a lower alkyl group and oxo group, 8) a lower alkenyl group which may be substituted by carboxyl group or an amide or an ester thereof, 9) an amino group which may be substituted by a group selected from the group consisting of i) a phenyl group, ii) a lower alkoxycarbonyl group, iii) a lower alkanesulfonyl group, iv) a carbamoyl group which may be substituted by a lower alkyl group or a lower alkyl-phenyl group, v) a lower alkanoyl group, vi) a lower alkyl group, vii) a lower alkenyl group, and viii) a thiocarbamoyl group which may be substituted by a lower alkyl group, 10) a carbamoyl group which may be substituted by a lower alkyl group, a hydroxy-lower alkyl group, a morpholino-lower alkyl group, a phenyl-lower alkyl group or a lower alkanesulfonyl group, 11) a sulfamoyl group which may be substituted by a group consisting of i) a lower alkyl group, ii) a benzoyl group, iii) a lower alkoxycarbonyl group, and iv) a lower alkanoyl group, 12) a lower alkenyloxy group, 13) a lower alkylenedioxy group, 14) a piperazinylcarbonyl group which may be substituted by a lower alkyl group, 15) a lower alkanoyl group, 16) cyano group, 17) a lower alkylthio group, 18) a lower alkanesulfonyl group, 19) a lower alkylsulfinyl group, and 20) a group of the formula: —(CH$_2$)$_q$—O— wherein q is an integer of 2 or 3;

b) a pyridyl group which may be substituted by a lower alkyl group;

c) a thienyl group which may be substituted by a group selected from the group consisting of:
1) a halogen atom,
2) a lower alkyl group which may be substituted by hydroxyl group,
3) cyano group,
4) formyl group,
5) a lower alkoxy group, and
6) a lower alkanoyl group;

d) a benzofuranyl group;

e) a pyrimidinyl group which may be substituted by a lower alkoxy group;

f) a isoxazolyl group which may be substituted by a lower alkyl group; and g) a pyrrolyl group which may be substituted by a lower alkoxycarbonyl group.

In preferred embodiment of the present invention,

Ring A is a benzene ring,

Q is a bond,

W is a —CH=CH— group, $R^1$ is selected from the group consisting of:
a) hydrogen atom,
b) a halogen atom,
c) a lower alkyl group,
d) a lower alkoxy group,
e) nitro group,
f) an amino group which may be substituted by a group selected from the group consisting of 1) a lower alkyl group, 2) a lower alkanoyl group, 3) a lower alkoxycarbonyl group, 4) a lower alkanesulfonyl group which may be substituted by a halogen atom, 5) a benzenesulfonyl group which may be substituted by a lower alkyl group, a trihalogeno-lower alkyl group, a halogen atom or a lower alkoxy group, 6) thiophenesulfonyl group, 7) a carbamoyl group which may be substituted by a lower alkyl group or a lower alkyl-phenyl group, 8) a thiocarbamoyl group which may be substituted by a lower alkyl group, and 9) a sulfamoyl group which may be substituted by a lower alkyl group,
g) carboxyl group
h) a carbamoyl group which may be substituted by a lower alkanesulfonyl group,
i) a lower alkanesulfonyl group,
j) a sulfamoyl group,
k) phenyl group,
l) a pyrrolidinyl group which may be substituted by oxo group,
l) a pyrrolyl group which may be substituted by a lower alkyl group,
m) a thienyl group,
n) an isoxazolyl group which may be substituted by a lower alkyl group,
o) a thiazolyl group
p) a pyrazolyl group,
q) a pyrazinyl group,
r) a pyridyl group, and
s) hydroxyl group;

$R^2$ is hydrogen atom, or a halogen atom;

$R^3$ is hydrogen atom, or a halogen atom;

$R^4$ is a) a carboxyl group,
b) a lower alkoxycarbonyl group which may be substituted by a lower alkyl-amino group, or
c) a carbamoyl group which may be substituted by a lower alkanesulfonyl group;

$R^5$ is selected from the group consisting of:
a) hydrogen atom,
b) an amino group which may be substituted by a lower alkanoyl group, a lower alkoxycarbonyl group or a lower alkanesulfonyl group,
c) a lower alkanoyl group,
d) a lower alkyl group which may be substituted by 1) hydroxyl group, or 2) an imino group which is substituted by hydroxyl group or a lower alkoxy group,
e) a lower alkoxy group, and
f) a halogen atom;

$R^6$ is a phenyl group which may have 1–5 substituents selected from the group consisting of:
a) a halogen atom,
b) formyl group,
c) a hydroxyl group,
d) a lower alkoxy group which may be substituted by 1) a carboxyl group, 2) a hydroxyl group, 3) a cyano group, 4) a halogen atom, 5) an amino group which may be substituted by a lower alkyl group, 6) a pyridyl group, 7) a phenyl group, 8) a thienyl group, or 9) a lower alkoxy group, e) a lower alkyl group which may be substituted by 1) an amino group which may be substituted by a lower alkyl group, a hydroxy-lower alkyl group, a lower alkylamino-lower alkyl group or a phenyl group, 2) a piperidinyl group which may be substituted by a lower alkylenedioxy group, 3) a morpholino group which may be substituted by a lower alkyl group, 4) a thiomorpholino group in which sulfur atom may be oxidized, 5) a piperazinyl group which may be substituted by a lower alkyl group, a hydroxy-lower alkyl group, a lower alkanoyl group or a phenyl-lower alkyl group, 6) pyrrolidinyl group which may be substituted by oxo group, or 7) an imidazolidinyl group which may be substituted by 1–3 groups selected from the group consisting of a lower alkyl group and oxo group, f) an amino group which may be substituted by 1) a lower alkoxycarbonyl group, 2) a lower alkanesulfonyl group, 3) a carbamoyl group which may be substituted by a lower alkyl group a lower alkyl-phenyl group, 4) a lower alkanoyl group, 5) a lower alkyl group, 6) a lower alkenyl group, or 7) a thiocarbamoyl group which may be substituted by a lower alkyl group, g) a carbamoyl group which may be substituted by 1) a lower alkyl group, 2) a hydroxy-lower alkyl group, 3) a morpholino-lower alkyl group, 4) a phenyl-lower alkyl group, or 5) a lower alkanesulfonyl group, h) a sulfamoyl group which may be substituted by a lower alkyl group, i) a lower alkenyloxy group, j) a lower alkylenedioxy group, k) a cyano group, l) a lower alkylthio group, and m) a lower alkanesulfonyl group.

In more preferred embodiment of the present invention, $R^1$ is 1) hydrogen atom, 2) a halogen atom, 3) a lower alkanoylamino group, 4) a lower alkoxycarbonylamino group, 5) a lower alkanesulfonylamino group which may be substituted by a halogen atom, 6) a benzenesulfonylamino group which may be substituted by a lower alkyl group, a trihalogeno-lower alkyl group, a halogen atom or a lower alkoxy group, 7) thiophenesulfonylamino group, 8) an ureido group which may be substituted by a lower alkyl group or a lower alkyl-phenyl group, 9) a lower alkyl-thioureido group, or 10) a lower alkylsulfamoylamino group, $R^2$ is a halogen atom, $R^3$ is hydrogen atom or a halogen atom, and $R^6$ is a phenyl group which may have 1–3 substituents selected from the group consisting of 1) a lower alkoxy group, 2) a lower alkyl group which may be substituted by a group selected from the group consisting of a lower alkylamino group, a hydroxy-lower alkylamino group, a lower alkylamino-lower alkylamino group, piperidinyl group, a lower alkyl-piperidinyl group, morpholino group, a lower alkyl-morpholino group, a thiomorpholino group, piperazinyl group, a lower alkyl-piperazinyl group, a lower alkanoyl-piperazinyl group, and a pyrrolidinyl group, 3) a sulfamoyl group which may be substituted by a lower alkyl group, 4) a carbamoyl group which may be substituted by a lower alkyl group.

In another more preferred embodiment of the present invention, $R^1$ is hydrogen atom, $R^3$ is a halogen atom, and $R^6$ is 2-(lower alkoxy)phenyl group, 2,6-di(lower alkoxy) phenyl group, 2,6-di(lower alkoxy)-4-[[N,N-di(lower alkyl) amino]lower alkyl]phenyl group, 2,6-di(lower alkoxy)4-[(4-lower alkyl-1-piperazinyl)lower alkyl]phenyl group, 2,6-di (lower alkoxy)-4-[1-piperidinyl-lower alkyl]phenyl group, 2,6-di(lower alkoxy)-4-[N,N-di(lower alkyl)carbamoyl] phenyl group or 2,6-di(lower alkoxy)-4-[(morpholino)lower alkyl]phenyl group.

In another more preferred embodiment of the present invention, a lower alkoxy group is methoxy group.

Preferred compounds as the active ingredient of the present invention may be selected from the group consisting of:

N-(2,6-dichlorobenzoyl)-4-(2,6-dimethoxyphenyl)-L-phenylalanine;

N-(2,6-dichlorobenzoyl)-4-[2,6-dimethoxy-4-(piperidinomethyl)phenyl]-L-phenylalanine;

N-(2,6-dichlorobenzoyl)-4-[2,6-dimethoxy-4-[(4-methylpiperazinyl)amino]phenyl]-L-phenylalanine;

N-(2,6-dichlorobenzoyl)-4-[2,6-dimethoxy-4-(morpholinomethyl)phenyl]-L-phenylalanine;

N-(2,6-dichlorobenzoyl)-4-[2,6-dimethoxy-4-(N,N-dimethylamino)phenyl]-L-phenylalanine;

N-(2,6-dichlorobenzoyl)-4-[2,6-dimethoxy-4-(N,N-dimethylcarbamoyl)phenyl]-L-phenylalanine;

N-(2,6-dichloro-4-hydroxybenzoyl)-4-(2,6-dimethoxyphenyl)-L-phenylalanine;

N-(2,6-dichlorobenzoyl)-4-(2-ethoxy-6-methoxyphenyl)-L-phenylalanine;

N-(2,6-difluorobenzoyl)-4-(2-6,dimethoxyphenyl)-L-phenylalanine;

N-(2,6-dichlorobenzoyl)-4-(2,3-methylenedioxy-6-methoxyphenyl)-L-phenylalanine;

N-(2,6-dichlorobenzoyl)-3-(1-hydroxyethy)-4-(2,6-dimethoxyphenyl)-L-phenylalanine;

N-(2,6-dichlorobenzoyl)-4-(2,4,6-trimethoxyphenyl)-L-phenylalanine;

N-[2,6-dichloro-4-[(trifluoromethanesulfonyl)amino] benzoyl]-4-(2,6-dimethoxyphenyl)-L-phenylalanine; or N-[2,6-dichloro-4-[(2-thienylsulfonyl)amino]benzoyl]-4-(2, 6-dimethoxyphenyl)-L-phenylalanine;

or a lower alkyl ester such as ethyl ester thereof;

or pharmaceutically acceptable salt thereof.

The active ingredient of the present invention may be used in the form of an ester or amide thereof. As the ester thereof, there may be mentioned a) a lower alkyl ester which may be substituted by 1) pyridyl group, 2) an amino group which may be substituted by a lower alkyl group, 3) a lower alkanoyloxy group, 4) an aryl group; b) a lower alkenyl ester; c) a lower alkynyl ester; d) a lower cycloalkyl ester; e) an aryl ester. As the amide thereof, there may be mentioned an amide (—CONH$_2$) which may be substituted by 1) a lower alkyl group, a lower cycloalkyl group, aryl group, aryl-lower alkyl group, hydroxy group or a lower alkanesulfonyl group;

An ester of the formula [I] includes, for example, an ester which can be converted to the corresponding carboxylic acid in a body, for example, a lower alkyl ester (e.g., methyl ester), a lower alkanoyloxy-lower alkyl ester (e.g., acetoxymethyl ester) and the like. An amide of the formula [I] includes, for example, an N-unsubstituted amide, an N-monosubstituted amide (e.g., an N-lower alkyl amide), an N,N-disubstituted amide (e.g., an N,N-(lower alkyl)(lower alkyl) amide) and the like.

A pharmaceutically acceptable salt of the formula [I] includes, for example, a salt with an inorganic acid (e.g., hydrochloride, sulfate), a salt with an organic acid (e.g., p-toluenesulfonate, maleate), a salt with an inorganic base (e.g., a salt with an alkali metal such as a sodium salt or a potassium salt) or a salt with an amine (e.g., an ammonium salt).

The active ingredient of the present invention may be used either in a free form or in the form of pharmaceutically acceptable salts thereof. Pharmaceutically acceptable salts include acid-addition salts with inorganic acid or organic acid (e.g., hydrochloride, sulfate, nitrate, hydrobromide, methanesulfonate, p-toluenesulfonate, acetate), salt with inorganic base, organic base or amino acid (e.g., triethylamine salt, a salt with lysine, an alkali metal salt, an alkali earth metal, salt and the like).

The active ingredient may be formulated into a pharmaceutical composition comprising a therapeutically effective amount of the compound as defined above and a pharmaceutically acceptable carrier or diluent.

The composition can be used for treating or preventing $\alpha_4$ (including $\alpha_4\beta_1$ and $\alpha_4\beta_7$ adhesion mediated conditions in a mammal such as a human, especially used for treatment or prevention of $\alpha_4\beta_7$ adhesion mediated conditions. This method may comprise administering to a mammal or a human patient an effective amount of the compound or composition as explained above.

This method can be used to treat or prevent such inflammatory conditions as rheumatoid arthritis, asthma, psoriasis, eczema, contact dermatitis and other skin inflammatory diseases, diabetes, multiple sclerosis, systemic lupus erythematosus (SLE), inflammatory bowel disease including ulcerative colitis and Crohn's disease, and other diseases involving leukocyte infiltration of the gastrointestinal tract, or other epithelial lined tissues, such as skin, urinary tract, respiratory airway, and joint synovium. The method can be preferably used for treatment or prevention of inflammatory bowel disease including ulcerative colitis and Crohn's disease.

The present invention also relates to a method for inhibiting the interaction of a cell bearing a ligand of MAdCAM-1, including $\alpha 4\beta 7$ integrins, with MAdCAM-1 or a portion thereof (e.g., the extracellular domain), comprising contacting the cell with an active ingredient of the present invention. In one embodiment, the present invention relates to a method of inhibiting the MAdCAM-mediated interaction of a first cell bearing an $\alpha 4\beta 7$ integrin with MAdCAM, for example with a second cell bearing MAdCAM, comprising contacting the first cell with an active ingredient of the present invention. In another embodiment, the invention relates to a method of treating an individual suffering from a disease associated with leukocyte recruitment to tissues (e.g., endothelium) expressing the molecular MAdCAM-1.

Another embodiment of the present invention is a method of treating an individual suffering from a disease associated with leukocyte infiltration of tissues expressing the molecule MAdCAM-1.

According to the present method, the cell bearing the ligand for MAdCAM-1 is contacted with an effective amount of an (i.e., one or more) inhibitor as represented by Structural Formula [I]. As used herein, an inhibitor is a compound which inhibits (reduces or prevents) the binding of MAdCAM-1 to a ligand, including $\alpha 4\beta 7$ integrin, and/or which inhibits the triggering of a cellular response mediated by the ligand. An effective amount can be an inhibitory amount (such an amount sufficient to achieve inhibition of adhesion of a cell bearing a MAdCAM-1 ligand to MAdCAM-1). Ligands for MAdCAM-1 include $\alpha 4\beta 7$ integrins, such as human $\alpha 4\beta 7$ integrin, and its homologs from other species such as mice (also referred to as $\alpha 4\beta p$ or LPAM-1 in mice).

For example, the adhesion of a cell which naturally expresses a ligand for MAdCAM-1, such as a leukocyte (e.g., B lymphocyte, T lymphocyte) or other cells which express a ligand for MAdCAM-1 (e.g., a recombinant cell), to MAdCAM-1 can be inhibited in vitro and/or in vivo according to the present method.

In another aspect, the present invention relates to a method of treating an individual (e.g., a mammal, such as a human or other primate) suffering from a disease associated with leukocyte (e.g., lymphocyte, monocyte) infiltration of tissues (including recruitment and/or accumulation of leukocytes in tissues) which express the molecule MAdCAM-1. The method comprises administering to the individual a therapeutically effective amount of an inhibitor (i.e., one or more inhibitors) of Structural Formula [I]. For example, inflammatory diseases, including diseases which are associated with leukocyte infiltration of the gastrointestinal tract (including gut-associated endothelium), other mucosal tissues, or tissues expressing the molecular MAdCAM-1 (e.g., gut-associated tissues, such as venules of the lamina propria of the small and large intestine; and mammary gland (e.g., lactating mammary gland)), can be treated according to the present method. Similarly, an individual suffering from a disease associated with leukocyte infiltration of tissues as a result of binding of leukocytes to cells (e.g., endothelial cells) expressing the molecule MAdCAM-1 can be treated according to the present invention.

Diseases which can be treated accordingly include inflammatory bowel disease (IBD), such as ulcerative colitis, Crohn's disease and pouchitis resulting after proctocolectomy and ileoanal anastomosis after IBD; and other gastrointestinal diseases associated with leukocyte infiltration, such as Celiac disease, nontropical Sprue, enteropathy associated with seronegative arthropathies, lymphocytic and graft versus host diseases.

Pancreatitis and insulin-dependent diabetes mellitus are other diseases which can be treated using the present method. It has been reported that MAdCAM-1 is expressed by some vessels in the exocrine pancreas from NOD (nonobese diabetic) mice, as well as from BALB/c and SJL mice. Expression of MAdCAM-1 was reportedly induced on endothelium in inflamed islets of the pancreas of the NOD mouse, and MAdCAM-1 was the predominant address in expressed by NOD islet endothelium at early stages of insulitis (Hanninen, A. et al., J. Clin. Invest., 92: 2509–2515 (1993)). Further, accumulation of lymphocytes expressing $\alpha 4\beta 7$ within islets was observed, and MAdCAM-1 was implicated in the binding of lymphoma cells via $\alpha 4\beta 7$ to vessels from inflamed islets (Hanninen, A., et al., J. Clin. Invest., 92: 2509–2515 (1993)).

Examples of inflammatory diseases associated with mucosal tissues which can be treated according to the present method include mastitis (mammary gland), cholecystitis, cholangitis or pericholangitis (bile duct and surrounding tissue of the liver), chronic bronchitis, chronic sinusitis, asthma, and graft versus host disease (e.g., in the gastrointestinal tract). Chronic inflammatory diseases of the lung which result in interstitial fibrosis, such as hypersensitivity pneumonitis, collagen disease (in SLE and RA), sarcoidosis, and other idiopathic conditions can be amenable to treatment.

Vascular cell adhesion molecule-1 (VCAM-1), which recognizes the $\alpha 4\beta 1$ integrin (VLA-4), has been reported to play a role in in vivo leukocyte recruitment (Silber et al., J. Clin. Invest. 93:1554–1563 (1994)). However, these therapeutic targets are likely to be involved in inflammatory processes in multiple organs, and a functional blockade could cause systemic immune dysfunction. In contrast to VCAM-1, MAdCAM-1 is preferentially expressed in the gastrointestinal tract and mucosal tissues, binds the $\alpha 4\beta 7$ integrin found on lymphocytes, and participates in the homing of these cells to mucosal sites, such as Peyer's patches in the intestinal wall (Hamann et al., J. Immunol., 152:3282–3293 (1994)). As inhibitors of the binding of MAdCAM-1 to α4β7 integrin, the active ingredients of the present invention have the potential for fewer side effects due to, for example, effects on other tissue types where adhesion is mediated by other receptors, such as α4β1 integrin.

Undesired symptoms of the condition listed herein can alleviated using the present method. The symptoms may be caused by inappropriate cell adhesion and/or cell activation to release proinflammatory mediators mediated by α4β7 integrins. Such inappropriate cell adhesion or signal transduction would typically be expected to occur as a result of increased VCAM and/or MAdCAM expression on the surface of endothelial cells. Increased VCAM, MAdCAM and/or CS-1 expression can be due to a normal inflammatory response or due to abnormal inflammatory states The present method can be used to assess the inhibitory effect of a compound of the present invention and of other potential antagonists useful in the method on the interaction of MAdCAM-1 with a ligand for MAdCAM-1 in vitro or in vivo.

Compounds suitable for use in therapy can also be evaluated in vivo, using suitable animal models. Suitable animal models of inflammation have been described. For example, NOD mice provide animal model of insulin-dependent diabetes mellitus. CD45 RB$^{Hi}$ SCID model provide a model in mice with similarity to both Crohn's disease and ulcerative colitis (Powrie, F. et al., Immunity, 1: 553–562 (1994)). Captive cotton-top tamarins, a New World nonhuman primate species, develop spontaneous, often chronic, colitis that clinically and histolgocially resembles ulcerative colitis in humans (Madara, J. L. et al., Gastroenterology, 88: 13–19 (1985)). The tamarin model and other animal models of gastrointestinal inflammation using BALB/c mice (a (DSS)-induced inflammation model; DSS, dextran sodium sulfate). IL-10 knockout mice which develop intestinal lesions similar to those of human inflammatory bowel disease have also been described (Strober, W. and Ehrhardt, R. O., Cell, 75: 203–205 (1993)).

According to the method, an inhibitor can be administered to an individual (e.g., a human) alone or in conjunction with another agent, such as an additional pharmacologically active agent (e.g., sulfasalazine, an antiinflammatory compound, or a steroidal or other nonsteroidal antiinflammatory compound). A compound can be administered before, along with or subsequent to administration of the additional agent, in amounts sufficient to reduce or prevent MAdCAM-mediated binding to a ligand for MAdCAM-1, such as human α4β7.

An effective amount of the active ingredient can be administered by an appropriate route in a single dose or multiple doses. An effective amount is a therapeutically effective amount sufficient to achieve the desired therapeutic and/or prophylactic effect (such as an amount sufficient to reduce or prevent MAdCAM-mediated binding to a MAdCAM ligand, thereby inhibiting leukocyte adhesion and infiltration and associated cellular responses. Suitable dosages of active ingredient of the present invention for use in therapy, diagnosis or prophylaxis, can be determined by methods known in the art and can be dependent, for example, upon the individual's age, sensitivity, tolerance and overall well-being.

The active ingredient of the present invention or pharmaceutically acceptable salts thereof may be administered either orally or parenterally, and it may be used as a suitable pharmaceutical preparation, for example, a tablet, a granule, a capsule, a powder, an injection, and an inhalation by a conventional process.

The dose of the active ingredient of the present invention or a pharmaceutically acceptable salt thereof varies depending on an administration method, age, body weight, and state of a patient, but, in general, the daily dose is preferably about 0.1 to 100 mg/kg/day, particularly preferably 1 to 100 mg/kg/day.

Pharmaceutical Compositions

As indicated previously, the active ingredient of formula [I] can be formulated into pharmaceutical compositions. In determining when a compound of formula [I] is indicated for the treatment of a given disease, the particular disease in question, its severity, as well as the age, sex, weight, and condition of the subject to be treated, must be taken into consideration and this perusal is to be determined by the skill of the attendant physician.

For medical use, the amount of a compound of Formula [I] required to achieve a therapeutic effect will, of course, vary both with the particular compound, the route of administration, the patient under treatment, and the particular disorder or disease being treated. A suitable daily dose of a compound of Formula [I], or a pharmaceutically acceptable salt thereof, for a mammalian subject suffering from, or likely to suffer from, any condition as described herein before is 0.1 mg to 100 mg of the compound of formula [I], per kilogram body weight of the (systemic) mammalian subject. In the case of systemic administration, the dose may be in the range of 0.5 to 100 mg of the compound per kilogram body weight, the most preferred dosage being 0.5 to 50 mg/kg of mammal body weight administered two to three times daily. In the case of topical administration, e.g., to the skin or eye, a suitable dose may be in the range of 0.1 $\mu$g to 100 $\mu$g of the compound per kilogram, typically about 0.1 $\mu$g/kg.

In the case of oral dosing, a suitable dose of a compound of Formula [I], or a physiologically acceptable salt thereof, may be as specified in the preceding paragraph, but preferably is from 1 mg to 50 mg of the compound per kilogram, the most preferred dosage being from 5 mg to 25 mg/kg of mammal body weight, for example, from 1 to 10 mg/kg. Most preferably, a unit dosage of an orally administrable composition encompassed by the present invention contains less than about 1.0 g of a formula [I] compound.

It is understood that the ordinarily skilled physician or veterinarian will readily determine and prescribe the effective amount of a compound of Formula [I] to prevent or arrest the progress of the condition for which treatment is administered. In so proceeding, the physician or veterinarian could employ relatively low doses at first, subsequently increasing the dose until a maximum response is obtained.

The compounds and compositions of the present invention can be administered to patients suffering from a condition listed herein in an amount which is effective to fully or partially alleviate undesired symptoms of the condition. The symptoms may be caused by inappropriate cell adhesion or cell activation to release proinflammatory mediators mediated by α4β7 integrins. Such inappropriate cell adhesion or signal transduction would typically be expected to occur as a result of increased VCAM-1 and/or MAdCAM expression on the surface of endothelial cells. Increased VCAM-1, MAdCAM and/or CS-1 expression can be due to a normal inflammation response or due to abnormal inflammatory states. In either case, an effective dose of a compound of the invention may reduce the increased cell adhesion due to increased VCAM-1 and/or MAdCAM expression by endothelial cells. Reducing the adhesion observed in the disease state by 50% can be considered an effective reduction in adhesion. More preferably, a reduction in ex vivo adhesion by 90%, is achieved. Most preferably, adhesion mediated by VCAM-1, MAdCAM and/or CS-1 interaction is abolished by an effective dose. Clinically, in some instances, effect of the compound can be observed as a decrease in white cell infiltration into tissues or a site of injury. To achieve a therapeutic effectiveness, then, the compounds or compositions of the present invention are administered to provide a dose effective to reduce or eliminate inappropriate cell adhesion or inappropriate cell activation to alleviate undesired symptoms.

While it is possible for an active ingredient to be administered alone, it is preferable to present it as a pharmaceutical formulation comprising a compound of Formula [I] and a pharmaceutically acceptable carrier thereof. Such formulations constitute a further feature of the present invention.

The formulations, both for human and veterinary medical use, of the present invention comprise an active ingredient of Formula [I], in association with a pharmaceutically acceptable carrier thereof and optionally other therapeutic ingredients), which are generally known to be effective in treating the disease or condition encountered. The carrier(s) must be "acceptable" in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal inhalation (e.g., with an aerosol) or buccal administration. Such formulation are understood to include long-acting formulations known in the art. Oral and parenteral administration are preferred modes of administration.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired form.

Formulations of the present invention suitable for oral administration may be in the form of discrete units such as capsules, cachets, tablets, or lozenges, each containing a predetermined amount of the active ingredient in the form of a powder or granules; in the form of a solution or suspension in an aqueous liquid. Formulations for other uses could involve a nonaqueous liquid; in the form of an oil-in-water emulsion or a water-in-oil emulsion; in the form of an aerosol; or in the form of a cream or ointment or impregnated into a transdermal patch for use in administering the active ingredient transdermally, to a patient in need thereof. The active ingredient of the present inventive compositions may also be administered to a patient in need thereof in the form of a bolus, electuary, or paste.

The practitioner is referred to "Remington: The Science and Practice of Pharmacy," 19th Edition, c. 1995 by the Philadelphia College of Pharmacy and Science, as a comprehensive tome on pharmaceutical preparations.

According to the present invention, the novel compound [I] can be prepared by the following methods.

Method A

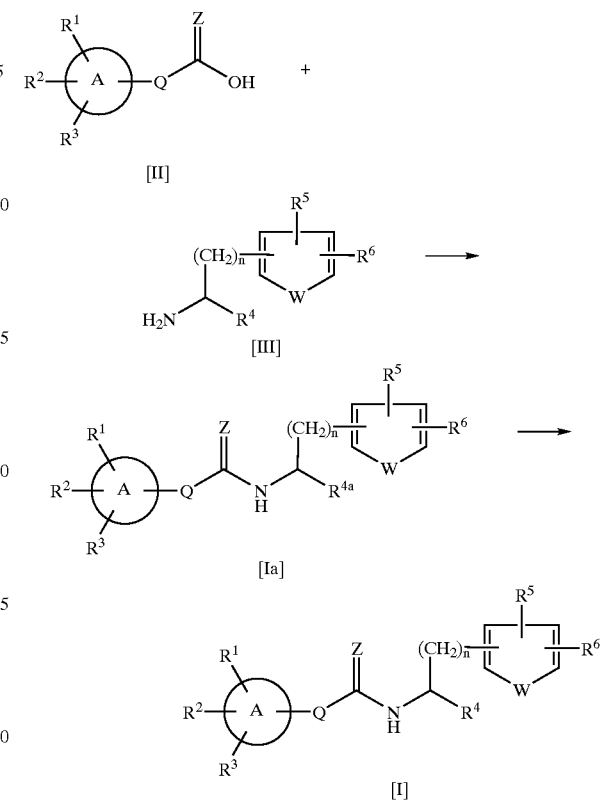

(wherein $R^{4a}$ is an ester group, and other symbols are the same as defined above)

The compound of the formula [I] or a pharmaceutically acceptable salt thereof may be prepared by:

(1) condensing a compound of the formula [II] a salt thereof or a reactive derivative thereof with a compound of the formula [III] or a salt thereof, (2) converting the ester group of the compound of the formula [Ia] into a carboxyl group, if desired, and (3) converting the carboxyl group of the resulting compound into an ester group, an amide group, a tetrazolyl group or a pharmaceutically acceptable salt thereof, if further desired.

A salt of the compound [II] and/or [III] includes, for example, a salt with an inorganic acid (e.g., trifluoroacetate, hydrochloride, sulfate), a salt with an inorganic base (e.g., an alkali metal salt such as a sodium salt or a potassium salt, an alkaline earth metal salt such has a barium salt or calcium salt).

(1) The condensation reaction can be carried out by a conventional method for a usual amide bond synthesis.

The condensation reaction of the compound [II] or a salt thereof with the compound [III] or a salt thereof is carried out in the presence of a condensing reagent with or without a base in a suitable solvent or without a solvent. The condensing reagent can be selected from any one which can be used for a conventional amide bond synthesis, for example, BOP-Cl, BOP reagent, DCC, EDC or CDI.

The base can be selected from an organic base (e.g., DIEA, DMAP, DBU, $Et_3N$), an alkali metal hydride (e.g., NaH, LiH), an alkali metal carbonate (e.g., $Na_2CO_3$, $K_2CO_3$), an alkali metal hydrogen carbonate (e.g., $NaHCO_3$, $KHCO_3$), an alkali metal amide (e.g., $NaNH_2$), an alkali metal alkoxide (e.g., NaOMe, KOMe), a lower alkyl alkali metal salt (e.g., n-BuLi, t-BuLi), an alkali metal hydroxide (e.g., NaOH, KOH), an alkaline earth metal hydroxide (e.g., Ba(OH)$_2$), and the like.

The solvent can be selected from any one which does not disturb the condensation reaction, for example, CH$_2$Cl$_2$, THF, DMF or a mixture thereof. The reaction is carried out at a temperature of 0° C. to room temperature, preferably at room temperature.

The condensation reaction of the compound [III] or a salt thereof with the reactive derivative of the compound [II], for example, with an acid halide (e.g., an acid chloride), a reactive ester (e.g., an ester with p-nitrophenol), an anhydride thereof, a mixed anhydride with other carboxylic acid (e.g., a mixed anhydride with acetic acid), and the like, is carried out in the presence of a base or without a base in a solvent or without a solvent.

The base can be selected from an organic base (e.g., DIEA, DMAP, DBU, Et$_3$N), an alkali metal hydride (e.g., NaH, LiH), an alkali metal carbonate (e.g., Na$_2$CO$_3$, K$_2$CO$_3$), an alkali metal hydrogen carbonate (e.g., NaHCO$_3$, KHCO$_3$), an alkali metal amide (e.g., NaNH$_2$), an alkali metal alkoxide (e.g., NaOMe, KOMe), a lower alkylalkali metal salt (e.g., n-BuLi, t-BuLi), an alkali metal hydroxide (e.g., NaOH, KOH), an alkaline earth metal hydroxide (e.g., Ba(OH)$_2$), and the like.

The solvent can be selected from any one which does not disturb the condensation reaction, for example, CH$_2$Cl$_2$, C$_2$H$_4$Cl$_2$, Et$_2$O, THF, DMF, CH$_3$CN, DMSO, benzene, toluene or a mixture thereof. The reaction is carried out at a temperature of −30° C. to 100° C.

(2) The conversion of the ester group into a carboxyl group can be carried out by a conventional method, which is selected according to the type of the ester group to be removed, for example, hydrolysis using a base (e.g., LiOH, NaOH) or an acid (e.g., HCl), treatment with an acid (e.g., TFA), catalytic reduction using a catalyst (e.g., palladium on activated carbon) and the like. The ester group can be selected from a conventional ester, for example, a lower alkyl ester, a lower alkenyl ester, a lower alkynyl ester, an aryl-lower alkyl ester (e.g., benzyl ester), an aryl ester (e.g., phenyl ester) and the like.

(3) The conversion of the carboxyl group into an ester group, an amide group or tetrazolyl group or conversion of the compound into a pharmaceutically acceptable salt thereof can be carried out by a conventional method. Particularly, the conversion of the carboxyl group into an ester group or an amide group can be carried out in a similar manner as described in Method A-(1). The conversion of the carboxyl group into tetrazolyl group is detailed in Procedure N below.

Method B

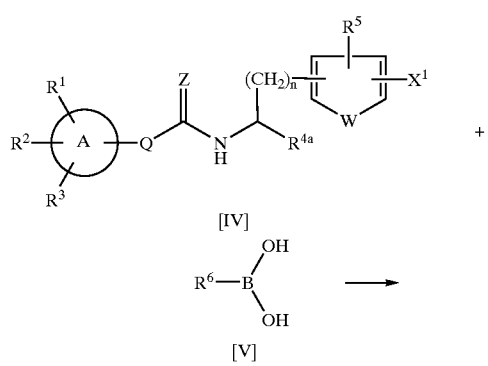

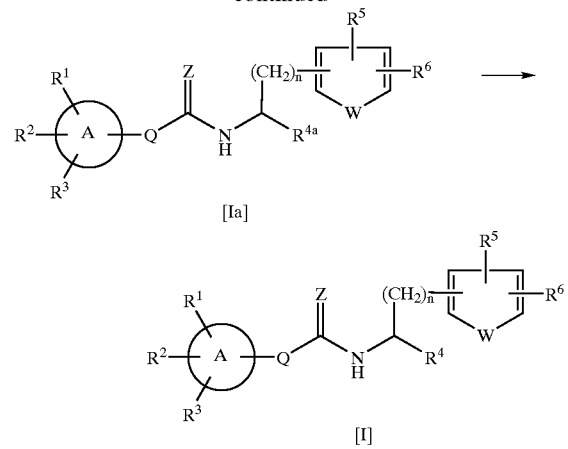

(wherein X$^1$ is a leaving group and other symbols are the same as defined above.)

The compound of the formula [I] can be prepared by:

(1) reacting a compound of the formula [IV] with a compound of the formula [V], (2) converting the ester group of the compound of the formula [Ia] into a carboxyl group, if desired, and (3) converting the carboxyl group of the resulting compound into an ester group, an amide group, a tetrazolyl group or a pharmaceutically acceptable salt thereof, if further desired.

Examples of the leaving group X$^1$ may be a halogen atom and a trifluoromethanesulfonyloxy group.

(1) The coupling reaction can be carried out by a conventional aryl coupling method, e.g., Suzuki coupling method (for reference of Suzuki coupling method: (a) Suzuki et al., *Synth. Commun.* 1981, 11, 513, (b) Suzuki, *Pure and Appl. Chem.* 1985, 57, 1749–1758, (c) Suzuki et al., *Chem. Rev.* 1995, 95, 2457–2483, (d) Shieh et al., *J. Org. Chem.* 1992, 57, 379–381), (e) Martin et al., *Acta Chemica Scandinavica,* 1993, 47, 221–230.)

The coupling reaction can be carried out, for example, at a temperature of room temperature to 100° C., preferably at a temperature of 80° C. to 100° C., in the presence of tetrakis(triphenylphosphine)palladium and a base (e.g., an inorganic base such as K$_2$CO$_3$) in an organic solvent. The organic solvent can be selected from any one which does not disturb the coupling reaction, for example, toluene, DME, DMF, H$_2$O or a mixture thereof.

(2) The conversion of ester group into carboxyl group can be carried out according to Method A-(2).

(3) The conversion of carboxyl group into ester group or amide group, a tetrazolyl group or pharmaceutically acceptable salt can be carried out according to Method A-(3).

Method C

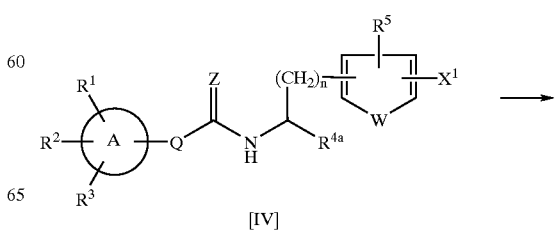

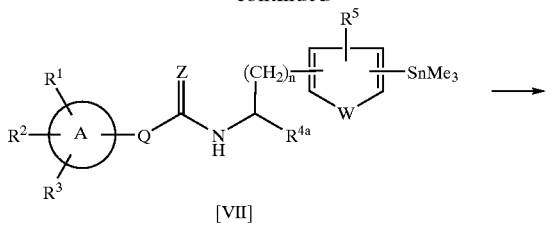

[VII]

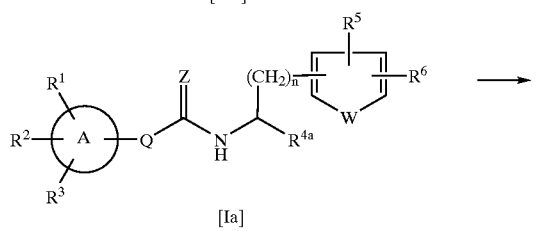

[Ia]

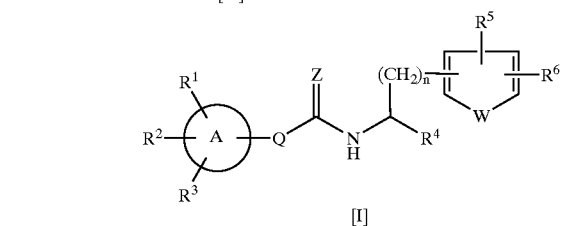

[I]

(wherein symbols are the same as defined above.)

The compound of the formula [I] can be also prepared by:
(1) converting the compound [IV] to the corresponding organotin compound (e.g., the compound of the formula [VII]),
(2) reacting the compound [VII] with a compound of the formula [VIII]:

R⁶—X  [VIII]

wherein X is a leaving group and $R^6$ is the same as defined above,
(3) converting the ester group of the compound of the formula [Ia] into a carboxyl group, if desired, and
(4) converting the carboxyl group of the resulting compound into an ester group, an amide group, a tetrazolyl group or a pharmaceutically acceptable salt thereof, if further desired.

Examples of the leaving group X is a halogen atom and a trifluoromethanesulfonyloxy group.

(1) The conversion of the compound [IV] to the organotin compound [VII] can be carried out, for example, by reacting the compound [IV] with hexaalkylditin (e.g., hexamethylditin) at a temperature of room temperature to 150° C., preferably at a temperature of 80° C. to 110° C., in the presence of tetrakis(triphenylphosphine)palladium and an additive (e.g., LiCl) in an organic solvent. The organic solvent can be selected from any one which does not disturb the coupling reaction, for example, dioxane, toluene, DME, DMF, H₂O or a mixture thereof.

(2) The coupling reaction can be carried out by a conventional aryl coupling method, e.g., Stille coupling method (for reference of Stille coupling method: Stille et al., *Angew. Chem. Int. Ed. Engl.*, 25, 508 (1986))

The coupling reaction can be carried out, for example, at a temperature of room temperature to 150° C., preferably at a temperature of 80° C. to 120° C., in the presence of tetrakis(triphenylphosphine)palladium in an organic solvent. The organic solvent can be selected from any one which does not disturb the coupling reaction, for example, toluene, DME, DMF, H₂O or a mixture thereof.

(3) The conversion of ester group into carboxyl group can be carried out according to Method A-(2).

(4) The conversion of carboxyl group into ester group or amide group, a tetrazolyl group or pharmaceutically acceptable salt can be carried out according to Method A-(3).

The compound [IV] may be prepared by condensing the compound of the formula [IIa]:

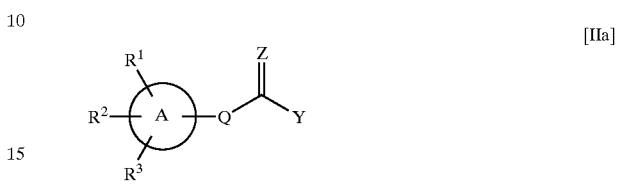

[IIa]

wherein Y is a halogen atom and the other symbols are the same as defined above, with the compound of the formula [IIIa]:

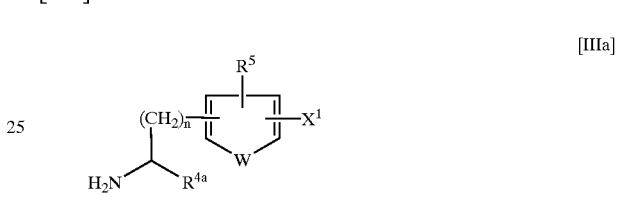

[IIIa]

wherein the symbols are the same as defined above or a salt thereof by the conventional method for the usual peptide synthesis as described above for the condensation reaction of the compound [III] or a salt thereof with the reactive derivative of the compound [II] (e.g., an acid halide).

The compound [IV] may be also prepared by:
(1) condensing the compound [IIa] with the compound of the formula [IIIb]:

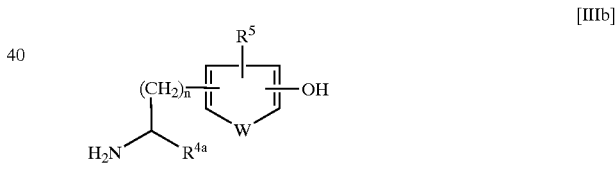

[IIIb]

wherein the symbols are the same as defined above or a salt thereof by the similar manner as described above,
(2) converting the hydroxyl group of the resulting compound into a leaving group by the conventional method. For example, the conversion of the hydroxy group into trifluoromethanesulfonyloxy group can be carried out by using triflic anhydride at 0° C. in the presence of a base(e.g., pyridine, NEt₃, DIEA) in an organic solvent (e.g., CH₂Cl₂, THF or a mixture thereof).

The compound [III] may be prepared by:
(1) condensing the compound of the formula [VIa]:

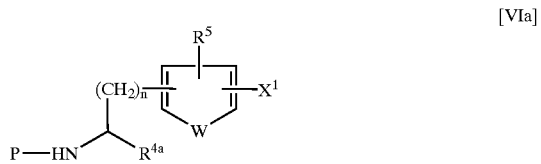

[VIa]

wherein P is a protecting group for an amino group and other symbols are the same as defined above with the compound [V] by a conventional aryl coupling method which is well known as Suzuki coupling method, (2) removing the protecting group for the amino group of the resulting compound.

The protecting group for the amino group can be selected from a conventional protecting group for an amino group, for example, a substituted or unsubstituted aryl-lower alkoxycarbonyl group (e.g., benzyloxycarbonyl group, p-nitrobenzyloxycarbonyl group), a lower alkoxycarbonyl group (e.g., tert-butoxycarbonyl group) and the like.

The removal of the protecting group for the amino group can be carried out by a conventional method, which is selected according to the type of the protecting group to be removed, for example, catalytic reduction using a catalyst (e.g., palladium on activated carbon), treatment with an acid (e.g., TFA) and the like.

The condensation reaction can be carried out in a similar manner as described for the coupling reaction of the compound [IV] and [V].

The compound [VIa] wherein $X^1$ is trifluoromethanesulfonyloxy group may be prepared by reacting the compound of the formula [VIb]:

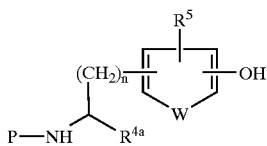

[VIb]

wherein the symbols are the same as defined above with triflic anhydride in a similar manner as described for the preparation of the compound [IV].

The compound [V] may be prepared by a conventional method (e.g., reference (a) Kuivila et al., J. Am. Chem. Soc., 1961, 83, 2159; (b) Gerrard, The Chemistry of Boron; Academic Press: New York, 1961; (c) Muetterties, The Chemistry of Boron and its Compounds: Wiley: New York, 1967; (d) Alamansa et al., J. Am. Chem. Soc., 1994, 116, 11723–11736):

(1) reacting a substituted or unsubstituted aryl lithium or a substituted or unsubstituted heteroaryl lithium with trimethyl borate at a temperature of −100° C. to room temperature in an organic solvent (e.g., diethyl ether, THF or the mixture thereof), and (2) hydrolyzing the resulting compound by a conventional method.

The hydrolysis can be carried out at room temperature in an organic solvent (e.g., diethyl ether, THF or the mixture thereof) in the presence of mild acid (e.g., AcOH or citric acid) and water.

The desired compound [I] of the present invention can be converted to each other. Such conversion of the present compound [I] into the other compound [I] may be carried out in an organic solvent by selecting one of the following procedures (Procedure A to K) according to the type of the substituent thereof. The organic solvent can be selected from any one which does not disturb the said procedure.

Procedure A: Reduction of Carbonyl Group

The compound [I] wherein $R^1$, $R^2$, $R^3$, $R^5$ or the substituent of the $R^6$ group is a hydroxy-lower alkyl group such as a hydroxymethyl group or a group of the formula: lower alkyl-CH(OH)— can be prepared by the reduction of the compound [I] wherein the corresponding $R^1$, $R^2$, $R^3$, $R^5$ or the substituent of the $R^6$ group is a carboxyl group, a formyl group or a group of the formula: lower alkyl-CO—. The reduction reaction can be carried out by a conventional method using a reducing agent such as borane, alkali metal borohydride (e.g., sodium borohydride) and the like at a temperature of 0° C. to room temperature in an organic solvent, e.g., methanol, ethanol, THF or the mixture thereof.

Procedure B: Oxidation of Formyl Group

The compound [I] wherein $R^1$, $R^2$, $R^3$, $R^5$ or the substituent of the $R^6$ group is a carboxyl group can be prepared by the oxidation of the compound [I] wherein the corresponding $R^1$, $R^2$, $R^3$, $R^5$ or the substituent of the $R^6$ group is a formyl group. The oxidation reaction can be carried out by a conventional method using an oxidizing agent, e.g., $KMnO_4$ and the like at a temperature of 0° C. to 50° C., preferably at a temperature of 30° C. to 50° C., in an organic solvent, e.g., acetone, $H_2O$ or the mixture thereof.

Procedure C: Reduction of Nitro Group

The compound [I] wherein $R^1$, $R^2$, $R^3$, $R^5$ or the substituent of the $R^6$ group is an amino group or has an amino group can be prepared by the reduction of the compound [I] wherein the corresponding $R^1$, $R^2$, $R^3$, $R^5$ or the substituent of the $R^6$ group is a nitro group or has a nitro group. The reduction reaction can be carried out by a conventional method, e.g., 1) a catalytic reduction using a catalyst such as Raney-nickel or a palladium on activated carbon and the like under a hydrogen atmosphere at room temperature in an organic solvent, e.g., methanol, $H_2O$ or the mixture thereof, 2) chemical reduction using metal and inorganic acid, such as Fe/HCl, Sn/HCl, $SnCl_2$/HCl and the like, or 3) reduction with a reducing agent, such as $Na_2S_2O_4$, in a suitable solvent, e.g., methanol, ethanol, $H_2O$ or the mixture thereof or without a solvent at a temperature of 0° C. to 80° C.

Procedure D: Removal of Protecting Group (D-1) The compound [I] wherein $R^1$, $R^2$, $R^3$, $R^5$ or the substituent of the $R^6$ group is an amino group or has an amino group can be prepared by the deprotection of the amino group of the compound [I] wherein the corresponding $R^1$, $R^2$, $R^3$, $R^5$ or the substituent of the $R^6$ groups is an N-protected amino group or has an N-protected amino group and the protecting group is a conventional protecting group for an amino group, e.g., benzyloxycarbonyl group, tert-butoxycarbonyl group, 9-fluorenylmethoxycarbonyl group, allyl group and the like. The deprotection reaction can be carried out by a conventional method, which is selected according to the type of the protecting group to be removed, e.g., 1) catalytic reduction using a catalyst such as palladium on activated carbon under a hydrogen atmosphere, 2) a treatment with an acid such as hydrogen chloride or TFA, 3) a treatment with an amine such as piperidine, 4) a treatment with a catalyst such as Wilkinson's catalyst, at room temperature or with heating in an organic solvent, e.g., $CH_2Cl_2$, THF, MeOH, EtOH and MeCN, or without an organic solvent.

(D-2) The compound [I] wherein $R^1$, $R^2$, $R^3$, $R^5$ or the substituent of the $R^6$ group is a sulfamoyl group can be prepared by the deprotection of the compound [I] wherein the corresponding $R^1$, $R^2$, $R^3$, $R^5$ or the substituent of the $R^6$ group is an N-protected sulfamoyl group and the protecting group is a conventional protecting group for a sulfamoyl group, e.g., tert-butyl group and the like. The deprotection reaction can be carried out by a conventional method, which is selected according to the type of the protecting group to be removed, e.g., a treatment with an acid such as TFA at a room temperature in an organic solvent, e.g., $CH_2Cl_2$, or without an organic solvent.

(D-3) The compound [I] wherein $R^1$, $R^2$, $R^3$, $R^4$, $R^5$ or the substituent of the $R^6$ group is a carboxyl group or has a carboxyl group can be prepared by the deprotection of the compound [I] wherein the corresponding $R^1$, $R^2$, $R^3$, $R^4$, $R^5$ or the substituent of the $R^6$ group is a protected carboxyl group or has a protected carboxyl group and the protecting group is a conventional protecting group for a carboxyl group, e.g., a lower alkyl group, a lower alkenyl group, a lower alkynyl group, an aryl-lower alkyl group, an aryl group and the like. The deprotection reaction can be carried out by a conventional method, which is selected according to the type of the protecting group to be removed, for example, hydrolysis using a base (e.g., NaOH, LiOH, KOH) or an acid (e.g., hydrochloric acid) treatment with an acid (e.g., TFA), catalytic reduction using a catalyst (e.g., palladium on activated carbon) and the like, at room temperature in an organic solvent (e.g., MeOH, EtOH or THF) or without an organic solvent.

(D-4) The compound [I] wherein $R^1$, $R^2$, $R^3$, $R^5$ or the substituent of the $R^6$ group is a hydroxyl group or has a hydroxyl group can be prepared by the deprotection of the compound [I] wherein the corresponding $R^1$, $R^2$, $R^3$, $R^5$ or the substituent of the $R^6$ group is a protected hydroxyl group or has a protected hydroxyl group and the protecting group is a conventional protecting group for a hydroxyl group, e.g., a methyl group, methoxymethyl group, tetrahydropyranyl group and the like. The deprotection reaction can be carried out by a conventional method, which is selected according to the type of the protecting group to be removed, for example, a treatment with $BBr_3$ for the demethylation of a methoxy group, and a treatment with HCl at a temperature of $-78°$ C. to room temperature in an organic solvent, e.g., $CH_2Cl_2$ and MeOH for removal of methoxymethyl group.

Procedure E: Acylation of Amino Group (E-1) The compound [I] wherein $R^1$, $R^2$, $R^3$, $R^5$ or the substituent of the $R^6$ group is an N-acylamino group, e.g., a lower alkanoylamino group, a lower alkoxycarbonylamino group, an arylcarbonylamino group, a chlorosulfonylcarbamoylamino group (such as 3-chlorosulfonylureido group), a lower alkyl carbamoylamino group (such as 3-(lower alkyl)ureido group), a substituted or unsubstituted arylcarbamoyl amino group (such as 3-(substituted or unsubstituted aryl)ureido group), a (substituted or unsubstituted lower alkyl)thiocarbamoylamino group (such as 3-(lower alkyl) thioureido group, 3-(phenyl-lower alkyl)thioureido group) can be prepared by the N-acylation of the compound [I] wherein the corresponding $R^1$, $R^2$, $R^3$, $R^5$ or the substituent of the $R^6$ group is an amino group. The N-acylation reaction can be carried out by a conventional method using 1) an acylating reagent, e.g., a lower alkanoyl halide, a lower alkanoic acid anhydride, a lower alkyl halogenoformate such as a lower alkyl chloroformate, an aryl carbonyl halide, a chlorosulfonyl isocyanate, a lower alkyl isocyanate, a substituted or unsubstituted aryl isocyanate or a lower alkyl isocyanate, or 2) when preparing a lower alkoxycarbonylamino group, a (lower alkyl)carbamoylamino group, a substituted or unsubstituted arylcarbamoyl amino group, a (substituted or unsubstituted lower alkyl) thiocarbamoylamino group, a condensing reagent, e.g., CDI, thioCDI, and a requisite amine or alcohol, at a temperature of $0°$ C. to $100°$ C., preferably at a temperature of room temperature to $90°$ C., with a base (e.g., DIEA, DMAP, pyridine, $NaHCO_3$, $Na_2CO_3$, $KHCO_3$, $K_2CO_3$) or without a base in an organic solvent (e.g., THF, $CH_3CN$, $CH_2Cl_2$, DMF, toluene, acetone and the mixture thereof).

(E-2) The compound [I] wherein $R^1$, $R^2$, $R^3$, $R^5$ or the substituent of the $R^6$ group is an N-(lower alkylsulfonyl) amino group (e.g., methanesulfonylamino group), an N-(substituted or unsubstituted arylsulfonyl)amino group (e.g., p-toluenesulfonylamino group, benzenesulfonylamino group) or an N-(substituted or unsubstituted heteroarylsulfonyl)amino group (e.g., quinolinosulfonylamino group) can be prepared by the N-sulfonylation of the compound [I] wherein the corresponding $R^1$, $R^2$, $R^3$, $R^5$ or the substituent of the $R^6$ group is an amino group. The N-sulfonylation reaction can be carried out by a conventional method using a lower alkylsulfonyl halide or a substituted or unsubstituted arylsulfonyl halide or a substituted or unsubstituted heteroarylsulfonyl halide in the presence of a base (e.g., pyridine, DMAP, $Et_3N$, DIEA, $NaHCO_3$, $KHCO_3$, $Na_2OC_3$, $K_2CO_3$) at a temperature of $0°$ C. to room temperature, preferably at room temperature, in an organic solvent (e.g., $CH_2Cl_2$, THF, DMF, $CH_3CN$, toluene, acetone and the mixture thereof).

(E-3) The compound [I] wherein $R^1$, $R^2$, $R^3$, $R^5$ or the substituent of the $R^6$ group is a ureido group can be prepared by the hydrolysis of the compound [I] wherein the corresponding $R^1$, $R^2$, $R^3$, $R^5$ or the substituent of the $R^6$ group is a 3-chlorosulfonylureido group. The hydrolysis can be carried out using a base (e.g., LiOH, NaOH and the like) or an acid (e.g., HCl) at room temperature in a suitable solvent (e.g., THF, $CH_3CN$, $H_2O$) or a mixture thereof.

Procedure F: Alkylation of Hydroxyl Group

The compound [I] wherein $R^1$, $R^2$, $R^3$, $R^5$ or the substituent of the $R^6$ group is a substituted or unsubstituted lower alkoxy group, e.g., a substituted or unsubstituted heterocycloalkyl-lower alkoxy group (such as a substituted or unsubstituted piperidyl-lower alkoxy group, or a substituted or unsubstituted pyrrolidinyl-lower alkoxy group), an aryl-lower alkoxy group, a heteroaryl-lower alkoxy group (such as a pyridyl-lower alkoxy group, a substituted or unsubstituted thiazolyl-lower alkoxy group, a substituted or unsubstituted isoxazolyl-lower alkoxy group, a substituted or unsubstituted thienyl-lower alkoxy group), a lower alkoxycarbonyl-lower alkoxy group, a carboxy-lower alkoxy group, a hydroxy-lower alkoxy group, a cyano-lower alkoxy group or a lower alkoxy group, can be prepared by the alkylation of the compound [I] wherein the corresponding $R^1$, $R^2$, $R^3$, $R^5$ or the substituent of the $R^6$ group is a hydroxy group, followed by the deprotection of the protecting group for carboxyl group or hydroxyl group by a conventional method, if desired. The alkylation reaction can be carried out using a halogenated lower alkane not having a substituent (e.g., methyl iodide) or that having a substituent such as a substituted or unsubstituted aryl group (e.g., unsubstituted aryl-lower alkyl halide such as benzyl bromide), a substituted or unsubstituted heteroaryl group (e.g., substituted or unsubstituted heteroaryl-lower alkyl halide such as pyridylmethyl bromide, isoxazolylmethyl bromide, thiazolylmethyl bromide), a heterocycloalkyl group (e.g., substituted heterocycloalkyl-lower alkyl halide such as N-lower alkylpyrrolidinyl-lower alkyl bromide, N-lower alkylpiperidyl-lower alkyl bromide), a lower alkoxycarbonyl group (e.g., halogenoalkanoic acid lower alkyl ester such as methyl bromoacetate) or a cyano group (e.g., bromoacetonitrile) in the presence of a base (e.g., $Et_3N$, DIEA, $NaHCO_3$, $KHCO_3$, $Na_2CO_3$, $K_2CO_3$, $KHCO_3$, $CsCO_3$) at a temperature of room temperature to $50°$ C. in an organic solvent (e.g., $CH_2Cl_2$, THF, DMF, $CH_3CN$, toluene).

The alkylation reaction can be also carried out by using a conventional alkylation method such as Mitsunobu Reaction (for reference of Mitsunobu reaction: (a) Mitsunobu, *Synthesis*, 1–28, (1981), (b) Hughes, *Organic Reactions*, 42, 335 (1992), (c) Mitsuhashi et al., *J. Am. Chem. Soc.*, 94, 26 (1972)).

Procedure G: Halogenation of Hydroxyl Group

The compound [I] wherein $R^1$, $R^2$, $R^3$, $R^5$ or the substituent of the $R^6$ group is a halogenated lower alkyl group can be prepared by the halogenation of the compound [I] wherein the corresponding $R^1$, $R^2$, $R^3$, $R^5$ or the substituent of the $R^6$ group is a hydroxyl lower alkyl group. The halogenation reaction can be carried out by the conventional method using, for example, a combination of tetrahalomethane (e.g., $CBr_4$) and triphenylphosphine at a room temperature in an organic solvent (e.g., $CH_2Cl_2$).

Procedure H: Conversion of Halogenated Alkyl Group to Alkoxy Alkyl Group

The compound [I] wherein $R^1$, $R^2$, $R^3$, $R^5$ or the substituent of the $R^6$ group is a lower alkoxy-lower alkyl group can be prepared by reacting the compound [I] wherein the corresponding $R^1$, $R^2$, $R^3$, $R^5$ or the substituent of the $R^6$ group is a halogenated lower alkyl group with an alkali metal lower alkoxide (e.g., sodium methoxide) at room temperature in an organic solvent (e.g., DMF, THF, $CH_3CN$).

Procedure I: Conversion of Carboxyl Group into Carbamoyl Group

The compound [I] wherein $R^1$, $R^2$, $R^3$, $R^4$, $R^5$ or the substituent of the $R^6$ group is a substituted or unsubstituted carbamoyl group (e.g., an N-lower alkylcarbamoyl group, an N,N-(lower alkyl)(lower alkyl)carbamoyl group, an N-(hydroxy-lower alkyl)carbamoyl group, an N-(morpholino-lower alkyl)carbamoyl group, an N-(aryl-lower alkyl)carbamoyl group, an N-(lower alkanesulfonyl) carbamoyl group, a hydroxycarbamoyl group, a carbamoyl group) can be prepared by condensing the compound [I] wherein the corresponding $R^1$, $R^2$, $R^3$, $R^4$, $R^5$ or the substituent of the $R^6$ group is a carboxyl group with a substituted or unsubstituted amine (e.g., a lower alkylamine, an N,N-(lower alkyl)(lower alkyl)amine, a (hydroxy-lower alkyl)amine, a (morpholino-lower alkyl)amine, an (aryl-lower alkyl)amine, hydroxyamine, ammonia) or a lower alkanesulfonamide.

The condensation reaction can be carried out by the conventional method for a usual peptide synthesis as described for the condensing reaction of the compound [II] and [III].

Procedure J: Reductive Alkylation (J-1) The compound [I] wherein $R^1$, $R^2$, $R^3$, $R^5$ or the substituent of the $R^6$ group is an amino-lower alkyl group, a lower alkyl amino-lower alkyl group or an arylamino-lower alkyl group can be prepared by the reductive alkylation of the corresponding ammonia, lower alkyl amine or aryl amine with the compound [I] wherein the corresponding $R^1$, $R^2$, $R^3$, $R^5$ or the substituent of the $R^6$ group is a formyl group. The reductive alkylation reaction can be carried out by the conventional method using a reductive agent (e.g., sodium cyanoborohydride) and an acid (e.g., HCl) at room temperature in an organic solvent (e.g., MeOH, THF, dioxane, or the mixture thereof).

(J-2) The compound [I] wherein $R^1$, $R^2$, $R^3$, $R^5$ or the substituent of the $R^6$ group is an N,N-dimethylamino group can be prepared by the reductive alkylation of the compound [I] wherein the corresponding $R^1$, $R^2$, $R^3$, $R^5$ or the substituent of the $R^6$ group is an amino group. The reductive alkylation can be carried out by the conventional method using formaldehyde, a reducing agent (e.g., sodium cyanoborohydride) and an acid (e.g., HCl) at room temperature in an organic solvent (e.g., MeOH, EtOH, THE, dioxane) or $H_2O$ or the mixture thereof.

Procedure K: Wittig Reaction

The compound [I] wherein $R^1$, $R^2$, $R^3$, $R^5$ or the substituent of the $R^6$ group is a lower alkokycarbonyl-ethenyl group can be prepared by the Wittig reaction of the compound [I] wherein the corresponding $R^1$, $R^2$, $R^3$, $R^5$ or the substituent of the $R^6$ group is a formyl group. The Wittig reaction can be carried out by the conventional method using, for example, (triphenylphosphoranylidene)acetic acid lower alkyl ester at a temperature of 50° C. to 100° C. in an organic solvent (e.g., toluene, THF).

Procedure L: Conversion of Halogenated Alkyl Group to Amino Alkyl Group

The compound [I] wherein $R^1$, $R^2$, $R^3$, $R^5$ or the substituent of the $R^6$ group is a lower alkyl group which is substituted by a substituted or unsubstituted amino group, a substituted or unsubstituted piperidinyl group, a substituted or unsubstituted morpholino group, a thiomorpholino group which may be oxidized, a substituted or unsubstituted piperazinyl group, or a substituted or unsubstituted pyrrolidinyl group can be prepared by reacting the compound [I] wherein the corresponding $R^1$, $R^2$, $R^3$, $R^5$ or the substituent of the $R^6$ group is a halogenated lower alkyl group with a requisite amine at room temperature or under cooling in an organic solvent (e.g., DMF, THF, $CH_2Cl_2$) or without a solvent, with or without a base such as $Et_3N$, DIEA.

In particular, the compound [I] wherein $R^1$ and $R^5$ are hydrogen atoms, $R^2$ and $R^3$ are halogen atoms, and $R^6$ is a phenyl group substituted by a lower alkoxy group and a lower alkyl group which is substituted by a group selected from the group consisting of a substituted or unsubstituted amino group, a substituted or unsubstituted piperidinyl group, a substituted or unsubstituted morpholino group, a substituted or unsubstituted piperazinyl group and a substituted or unsubstituted pyrrolidinyl group can be prepared by reacting the compound [I] wherein $R^1$ and $R^5$ are hydrogen atoms, $R^2$ and $R^3$ are halogen atoms, and $R^6$ is a phenyl group substituted by a lower alkoxy group and a halogeno-lower alkyl group with a requisite amine such as a substituted or unsubstituted ammonia, a substituted or unsubstituted piperidine, a substituted or unsubstituted morpholine, a substituted or unsubstituted piperazine and a substituted or unsubstituted pyrrolidine. The reaction can be carried out as described above.

Procedure M: Conversion of Carbonyl Group to Thiocarbonyl Group

The compound wherein Z is sulfur atom can be prepared by reacting the compound [I] wherein Z is oxygen atom with Lawesson's reagent in a suitable organic solvent (e.g., toluene, xylene) at a temperature of 50° C. to 150° C.

Procedure N: Conversion of Carboxyl Group to Tetrazoly Group

The compound [I] wherein $R_4$ is tetrazolyl group can be prepared from the compound [I] wherein $R_4$ is carboxyl group following the procedure described in the J. Med. Chem., 41, 1513–1518, 1998. The procedure can be summarized in the following scheme:

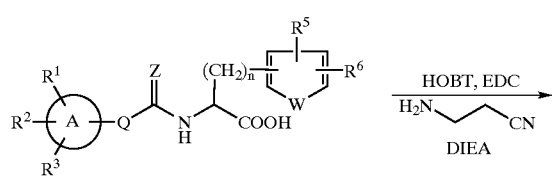

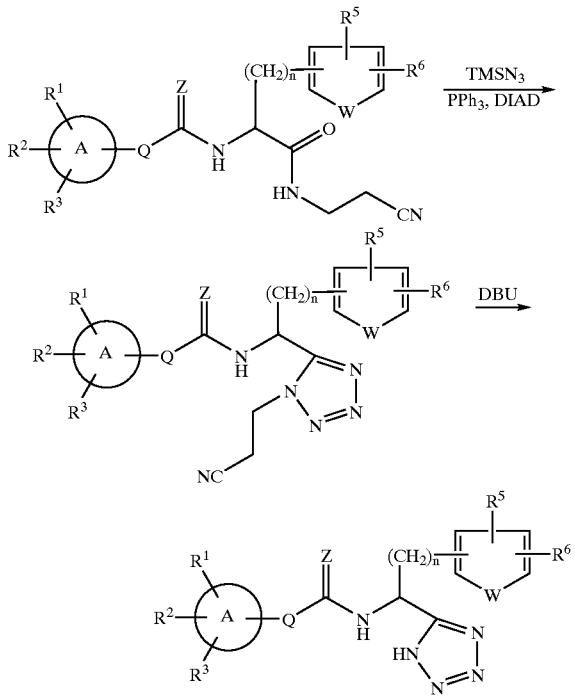

Procedure O: Conversion of Carboxyl Group to Alkoxycarbonyl Group

The compound [I] wherein $R^1$, $R^2$, $R^3$, $R^4$, $R^5$ or the substituent of the $R^6$ group is a substituted or unsubstituted lower alkoxycarbonyl group can be prepared by condensing the compound [I] wherein the corresponding $R^1$, $R^2$, $R^3$, $R^4$, $R^5$ or the substituent of the $R^6$ group is a carboxyl group with a substituted or unsubstituted alcohol (e.g., a halogeno-lower alcohol, pyridyl-lower alcohol, a (lower alkylamino)-lower alcohol, a lower alkoxy-lower alcohol).

The condensation reaction can be carried out by the conventional method for a usual ester synthesis as described for Method A-(3).

Procedure P: Reduction of Hydroxyl Group

The compound [I] wherein $R^1$, $R^2$, $R^3$, $R^5$ or the substituent of the $R^6$ group is a lower alkyl group can be prepared by reducing the compound [I] wherein the corresponding $R^1$, $R^2$, $R^3$, $R^5$ or the substituent of the $R^6$ group is a hydroxy-lower alkyl group. The reduction can be carried out using a reducing reagent such as a silane compound (e.g., $Et_3SiH$) in the presence of Lewis acid (e.g., $BF_3$, $TiCl_4$) in a suitable organic solvent (e.g., MeCN, $CH_2Cl_2$, THF) at a temperature of 0° C. to −78° C.

Procedure Q: Halogenation of Phenyl Group

The compound [I] wherein $R^6$ is a substituted or unsubstituted halogeno-phenyl group can be prepared by reacting the compound [I] wherein $R^6$ is a substituted or unsubstituted phenyl group with halogenating reagent (e.g., $Bu_4NBr_3$, 3,5-dichloro-1-fluoropyridinium triflate) in a suitable solvent (e.g., MeCN, $CH_2Cl_2$, THF) at room temperature or with heating.

Procedure R: Nitration of Phenyl Group

The compound [I] wherein $R^6$ is a substituted or unsubstituted nitro-phenyl group can be prepared by reacting the compound [I] wherein $R^6$ is a substituted or unsubstituted phenyl group with $HNO_3$ in a suitable solvent (e.g., THF, NeCN, MeOH, EtOH) at a temperature of room temperature to 100° C.

Procedure S: Converting Phenyl Group to Carbamoyl-phenyl Group

The compound [I] wherein $R^6$ is a substituted or unsubstituted carbamoyl-phenyl group can be prepared by 1) reacting the compound [I] wherein $R^6$ is a substituted or unsubstituted phenyl group with chlorosulfonyl isocyanate and 2) hydrolyzing the obtained compound. The reaction of the compound [I] and the isocyanate can be carried out in a suitable solvent (e.g., MeCN, $CH_2Cl_2$, THF) at a temperature of 0° C. to room temperature. The hydrolysis can be carried out with an acid (e.g., HCl, $HNO_3$, $H_2SO_4$) in a suitable solvent (e.g., MeCN, $H_2O$) at a temperature of room temperature to 100° C.

Procedure T: Conversion of Alkanoyl Group to Imino-alkyl Group

The compound [I] wherein $R^1$, $R^2$, $R^3$, $R^5$ or the substituent of the $R^6$ group is a (hydroxyimino)-lower alkyl or (a lower alkoxyimino)-lower alkyl group can be prepared by reacting the compound [I] wherein the corresponding $R^1$, $R^2$, $R^3$, $R^5$ or the substituent of the $R^6$ group is a lower alkanoyl group with hydroxyamine or a lower alkoxyamine in a suitable solvent such as a lower alcohol (e.g., MeOH, EtOH, PrOH or BuOH) and MeCN, with a base such as alkali metal acetate (e.g., NaOAc) at room temperature or with heating.

Procedure U: Conversion of Halogen Atom to Heterocyclic Group

The compound [I] wherein $R^1$, $R^2$ or $R^3$ is a substituted or unsubstituted heterocyclic group can be prepared by reacting the compound [I] wherein the corresponding $R^1$, $R^2$ or $R^3$ is halogen atom with a (substituted or unsubstituted heterocyclic)boronic acid using a conventional aryl coupling method such as Suzuki Coupling method. The coupling reaction can be carried out following the procedure as describe in Method A.

Procedure V: Oxidation of Sulfur Atom

The compound [I] wherein the substituent of the $R^6$ group is a lower alkylsulfinyl group, a lower alkylsulfonyl group, a thiomorpholino-lower alkyl S-oxide group a thiomorpholino-lower alkyl S,S-dioxide group can be prepared by oxidizing the compound [I] wherein the corresponding substituent of the $R^6$ group is a lower alkylthio group or a thiomorpholino-lower alkyl group with an oxidant such as a peracid (e.g., mCPBA, $H_2O_2$, AcOOH, PhCOOOH) in a suitable solvent (e.g., $CH_2Cl_2$) at room temperature or under cooling.

Procedure W: Imidation of Hydroxy-lower alkyl

The compound [I] wherein $R^1$, $R^2$, $R^3$ or the substituent of the $R^6$ group is a lower alkyl group which is substituted by succinimido group or 2,5-dioxo-1-imidazolidinyl group optionally substituted by a lower alkyl group can be prepared by the imidation of the compound [I] wherein the corresponding $R^1$, $R^2$, $R^3$ or the substituent of the $R^6$ group is a hydroxy-lower alkyl group. The imidation can be carried out by using a conventional method such as Mitsunobu Reaction (reference of Mitsunobu reaction is made in Procedure F). The reaction can be carried out by reacting the compound [I] with a di(lower alkyl) azodicarboxylate (e.g., diethyl azodicarboxylate), a tri(lower alkyl)- or triarylphosphine (e.g., triphenylphospphine), and a requisite imide (e.g., succinimide or hydantoin optionally substituted by a lower alkyl group), in a suitable organic solvent (e.g., $Et_2O$ and THF) at a temperature of −20° C. to 50° C.

The active ingredient of the present invention are exemplified by the following examples but not limited thereby.

EXAMPLES

Example 1

N-(2,6-Dichlorobenzoyl)-4-(2-methoxyphenyl)-L-phenylalanine methyl ester (1A) and N-(2,6-Dichlorobenzoyl)-4-(2-methoxyphenyl)-L-phenylalanine (1B).

1) Pyridine (3.58 mL) was added to a solution of N-(tert-butoxycarbonyl)-L-tyrosine methyl ester (4.36 g) in anhydrous CH$_2$Cl$_2$ (100 mL) under N$_2$. The solution was cooled to 0° C. and triflic anhydride (3 mL) was added dropwise with stirring. After the addition was over the ice-bath was removed and the mixture was stirred for 3 h at room temperature. The mixture was sequentially washed with water, 1 N HCl and water. The resulting CH$_2$Cl$_2$ solution was finally washed with NaHCO$_3$, followed by water, dried (MgSO$_4$) and evaporated. The residue was purified by flash column chromatography (silica gel; eluent: toluene/EtOAc 9:1) to yield N-(tert-butoxycarbonyl)-O-(trifluoromethanesulfonyl)-L-tyrosine methyl ester (6.2 g) ESMS: m/z 500 (MH$^+$).

2) To a mixture of 2-methoxybenzene boronic acid (0.446 g) and anhydrous K$_2$CO$_3$ (0.84 g) in toluene/DMF (25 mL/2.5 mL) under N$_2$ was added a solution of the product obtained above (1.0 g) in 5 mL of toluene. Pd(PPh$_3$)$_4$ (0.48 g) was added and the mixture was heated at 80° C. for 24 h. The mixture was cooled, filtered through Celite and evaporated. The residue was taken up in EtOAc and washed with water. The organic layer was dried (MgSO$_4$), evaporated, and the crude material was purified by flash column chromatography (silica gel; eluent: EtOAc/hexane 1/3) to yield N-(tert-butoxycarbonyl)-4-(2-methoxyphenyl)-L-phenylalanine methyl ester (0.64 g). ESMS: m/z 386 (MH$^+$)

3) To a solution of the product obtained above (2.97 g) in CH$_2$Cl$_2$ (20 mL) was added TFA (20 mL) and the mixture stirred for 1.5 h. The solution was evaporated. The residue was dissolved in CH$_2$Cl$_2$ (20 mL) and the solution was evaporated. This process was repeated once more and finally the residue was dried under high vacuum to yield the TFA salt of 4-(2-methoxyphenyl)-L-phenylalanine methyl ester (2.93 g). ESMS: m/z 286 (MH$^+$).

4) To a solution of the product obtained above (2.3 g) in CH$_2$Cl$_2$ (30 mL) containing DIEA (2.24 g) at 0° C. was added a solution of 2,6-dichlorobenzoyl chloride (0.99 mL) with stirring. The mixture was warmed to room temperature and stirred for 24 h. The mixture was washed sequentially with water, 1N HCl, satd. NaHCO$_3$ and brine. The resulting CH$_2$Cl$_2$ solution was dried (MgSO$_4$), evaporated, and the crude material was purified by flash column chromatography (silica gel; eluent: EtOAc/hexane 1/4) to yield N-(2,6-dichlorobenzoyl)-4-(2-methoxyphenyl)-L-phenylalanine methyl ester (1.64 g) (1A). ESMS: m/z 458 (MH$^+$)

5) The product obtained above (0.1 g) was dissolved in a mixture of THF/MeOH (5 mL/2 mL). A solution of LiOH (monohydrate, 14 mg) in 2 mL of water was added and the mixture was stirred at room temperature for 3 h. The mixture was evaporated and the residue was treated with water. The resulting mixture was adjusted to pH 2 with 1N HCl and the mixture was extracted with EtOAc. The organic layer was washed with brine, dried and evaporated to N-(2,6-Dichlorobenzoyl)-4-(2-methoxyphenyl)-L-phenylalanine (0.08 g) (1B). ESMS: m/z 444 (MH$^+$). mp. 211° C.

Example 2

N-[(S)-2-Phenylpropionyl]-4-(2-methoxyphenyl)-L-phenylalanine

1) A mixture of 4-(2-methoxyphenyl)-L-phenylalanine methyl ester hydrochloride (0.03 g), (S)-2-phenylpropionic acid (0.014 g), EDC (0.02 g), HOBT (0.021 g) and DIEA (0.034 mL) in DMF (5 mL) was stirred at room temperature for 18 h. DMF was removed and the residue was partitioned between EtOAc and water. The organic layer was evaporated and washed sequentially with 10% citric acid, satd. NaHCO$_3$ and brine. The resulting organic layer was dried (MgSO$_4$), evaporated and the residue was purified by flash column chromatography (silica gel; eluent: CH$_2$Cl$_2$/EtOAc 9:1) to yield N-[(S)-2-phenylpropionyl]-4-(2-methoxyphenyl)-L-phenylalanine methyl ester (0.031 g). ESMS: m/z 417 (MH$^+$).

2) The product obtained above (0.031 g) was dissolved in a mixture of THF/MeOH (3 mL/0.3 mL). 2N LiOH (0.07 mL) was added and the mixture was stirred at room temperature for 3 h. The mixture was evaporated and the residue was treated with water. The resulting mixture was adjusted to pH 2 with 1N HCl and the mixture was extracted with EtOAc. The organic layer was washed with brine, dried and evaporated to yield the title compound (0.02 g). ESMS: m/z 403 (MH$^+$).

Example 3

N-(2,6-Difluorobenzoyl)-4-(2,6-dimethoxyphenyl)-L-phenylalanine 1) 2,6-Dimethoxybenzeneboronic acid (0.5 g) was dissolved in DME (10 mL). To the solution was added K$_2$CO$_3$ (0.7 g), N-(tert-butoxycarbonyl)-O-(trifluoromethanesulfonyl)-L-tyrosine methyl ester (0.4 g), Pd(Ph$_3$P)$_4$ (0.6 g) and water (0.2 mL). The resulting mixture was heated to 80° C. overnight. Subsequently EtOAc and water were added to the mixture. The EtOAc layer was dried (MgSO$_4$) and evaporated. The residue was purified by flash column chromatography (silica gel; eluent: EtOAc/hexane 1:2) to give N-(tert-butoxycarbonyl)-4-(2,6-dimethoxyphenyl)-L-phenylalanine methyl ester (380 mg).

2) To the product obtained above was added CF$_3$COOH (5 mL) and the mixture was stirred at room temperature for 4 h. The excess CF$_3$COOH was removed under reduced pressure. The residue was dissolved in CH$_2$Cl$_2$ and washed with saturated sodium bicarbonate. The organic phase was dried (MgSO$_4$) and evaporated to give 4-(2,6-dimethoxyphenyl)-L-phenylalanine methyl ester (260 mg).

3) The product obtained above (140 mg) was dissolved in dry CH$_2$Cl$_2$ (10 mL). To the mixture was added Et$_3$N (0.15 mL) and 2,6-difluorobenzoyl chloride (72 μL) and the mixture was stirred at room temperature for 6 h. CH$_2$Cl$_2$ was added, and the organic phase was washed with water, dried (MgSO$_4$), and evaporated. The residue was purified by flash column chromatography (silica gel; eluent: EtOAc/hexane 1:2) to give N-(2,6-difluorobenzoyl)-4-(2,6-dimethoxyphenyl)-L-phenylalanine methyl ester(160 mg). ESMS: m/z 455 (MH$^+$)

4) A solution of LiOH (monohydrate, 12 mg) in 0.4 mL of water was added to a solution of the product obtained above (90 mg) in THF (5 mL). Few drops of MeOH were added and the mixture was stirred at room temperature overnight. The excess organic solvent was removed under reduced pressure, water was added to the residue and the resulting solution was acidified with 10% citric acid. The resulting solid was collected by filtration, washed with water and dried to give the title compound (70 mg). ESMS: m/z 441 (MH$^+$).

Example 4

N-(2,6-Dichlorobenzoyl)-4-(2-thienyl)-L-phenylalanine methyl ester (4A) and: N-(2,6-Dichlorobenzoyl)-4-(2-thienyl)-L-phenylalanine (4B)

1) To a mixture of 2-thienylboronic acid (1.135 g) and anhydrous K$_2$CO$_3$ (2.23 g) in toluene/DMF (75 mL/7.5 mL)

under N$_2$ was added a solution of N-(tert-butoxycarbonyl)-O-(trifluoromethanesulfonyl)-L-tyrosine methyl ester (3.42 g) in 5 mL of toluene. Pd(PPh$_3$)$_4$ (1.4 g) was added and the mixture was heated at 80° C. for 24 h. After usual work-up as shown in Example 1 the crude material was purified by flash column chromatography (silica gel; eluent: EtOAc/hexane 1:3) to yield N-(tert-butoxycarbonyl)-4-(2-thienyl)-L-phenylalanine methyl ester(1.81 g). ESMS: m/z 362 (MH$^+$).

2) To a solution of the product obtained above (1.53 g) in CH$_2$Cl$_2$ (25 mL) was added TFA (25 mL) and the mixture was stirred for 1.5 h at room temperature. The mixture was evaporated. The residue was partitioned between CH$_2$Cl$_2$ (20 mL) and satd. NaHCO$_3$. The organic layer was separated, washed with brine, dried (MgSO$_4$) and evaporated to give 4-(2-thienyl)-L-phenylalanine methyl ester. The free base was treated with a solution of 10% HCl in Et$_2$O to provide the HCl salt (1.036 g). ESMS: m/z 262 (MH$^+$).

3) To a mixture of the HCl salt obtained above (0.2 g) in CH$_2$Cl$_2$ (5 mL) containing DIEA (0.42 mL) at 0° C. was added a solution of 2,6-dichlorobenzoyl chloride (0.12 mL) in CH$_2$Cl$_2$ (1 mL). The mixture was warmed to room temperature and stirred for 24 h, and washed sequentially with water, 1N HCl, saturated NaHCO$_3$ and brine. The organic layer was dried (MgSO$_4$), evaporated, and the residue was purified by flash column chromatography (silica gel; eluent: CH$_2$Cl$_2$/EtOAc/hexane 1:1:6) to yield N-(2,6-dichlorobenzoyl)-4-(2-thienyl)-L-phenylalanine methyl ester (0.15 g) (4A). ESMS: m/z 434 (MH$^+$).

4) The product obtained above (0.1 g) was dissolved in a mixture of THF/MeOH (5 mL/2 mL). A solution of LiOH (monohydrate, 14 mg) in 2 mL of water was added and the mixture was stirred at room temperature for 3 h. The mixture was evaporated and the residue was treated with water. The mixture was adjusted to pH 2 with 1N HCl and extracted with EtOAc. The extract was washed with brine, dried (MgS0$_4$) and evaporated to yield: N-(2,6-Dichlorobenzoyl)-4-(2-thienyl)-L-phenylalanine (0.08 g) (4B). ESMS: m/z 420 (MH$^+$).

Example 5

N-(2,6-Dichlorobenzoyl)-4-(2-methoxyphenyl)-D-phenylalanine

1) A solution of 2,6-dichlorobenzoylchloride (0.68 mL) in CH$_2$Cl$_2$ (5 mL) was added to a solution of an ice-cold solution of D-tyrosine methyl ester HCl salt (1.0 g) and DIEA (2.26 mL) in CH$_2$Cl$_2$ (15 mL). The mixture was stirred at room temperature for 24 h. The mixture was diluted with CH$_2$Cl$_2$ (50 mL) and washed successively with H$_2$O, 1 N HCl and brine. The organic layer was dried (MgSO$_4$) and evaporated, and the residue was recrystallized from EtOAc and hexanes to yield 1.46 g of N-(2,6-dichlorobenzoyl)-D-tyrosine methyl ester. ESMS: m/z 369 (MH$^+$).

2) Triflic anhydride (0.27 mL) was added slowly to an ice-cold solution of the product obtained above (0.5 g) in CH$_2$Cl$_2$ containing pyridine (0.33 mL). The mixture was stirred for 2.5 h and was washed successively with water, 1 N HCl, satd. NaHCO$_3$ and water. The organic layer was dried (MgSO$_4$), evaporated and the residue was purified by flash column chromatography (silica gel; eluent: toluene/EtOAc 9:1) to yield 0.65 g of N-(2,6-dichlorobenzoyl)-O-(trifluoromethanesulfonyl) -D-tyrosine methyl ester. ESMS: m/z 501 (MH$^+$).

3) Pd(PPh$_3$)$_4$ (0.09 g) was added to a suspension of 2-methoxybenzene boronic acid (0.082 g), K$_2$CO$_3$ (0.16 g) and the product obtained above (0.214 g) in toluene/DMF (4 mL/0.4 mL) under N$_2$. The mixture was heated at 80° C. for 24 h, cooled, filtered and the solvent was evaporated. The residue was taken up with EtOAc, washed with water, dried (MgSO$_4$) and evaporated. The crude product was purified by flash column chromatography (silica gel; eluent:toluene/EtOAc 10:1) to yield 45 mg of N-(2,6-dichlorobenzoyl)-4-(2-methoxyphenyl)-D-phenylalanine methyl ester. ESMS: m/z 458 (MH$^+$).

4) The product obtained above (90 mg) was hydrolyzed with LiOH in a similar manner as described for the preparation of Example 1 to give 25 mg of the title compound. ESMS: m/z 444 (MH$^+$). mp. 195° C.

Example 6

N-(2,6-Dichlorobenzoyl)-3-[2-methoxyphenyl)-DL-phenylalanine

By following the same procedure as Example 5, the title compound was obtained. ESMS: m/z 444 (MH$^+$). mp. 104° C.

Example 7

N-(2,6-Dichlorobenzoyl)-4-(2,6-dimethoxyphenyl)-L-phenylalanine methyl ester (7A) and N-(2,6-Dichlorobenzoyl)-4-(2,6-dimethoxyphenyl)-L-phenylalanine (7B)

1) 1,3-Dimethoxybenzene (4 g) was dissolved in freshly distilled THF (10 mL). This solution was cooled to –78° C. and n-BuLi (24 mL, 1.6 M solution in hexanes) was added dropwise to the cold solution. The mixture was stirred at –78° C. for 1 h, then warmed to room temperature and stirred for 1 h. The resulting mixture was cooled again to –78° C. and (MeO)$_3$B (6.7 mL) was added. The mixture was allowed to warm to room temperature and stirred overnight. Water (10 mL) was added, and the mixture was stirred for 0.5 h, acidified to pH 4 with acetic acid and extracted with EtOAc. The extract was dried (MgSO$_4$) and evaporated to give 2,6-dimethoxybenzeneboronic acid, which was used without further purification.

2) The product obtained above (0.3 g) and K$_2$CO$_3$ (0.5 g) were suspended in DME (10 mL). To the mixture was added N-(2,6-dichlorobenzoyl)-4-bromo-L-phenylalanine methyl ester (0.3 g), Pd(Ph$_3$P)$_4$ (0.3 g), water (0.4 mL) and the mixture was heated at 80° C. for 6 h. After cooling, EtOAc and water were added to the mixture. The EtOAc phase was dried (MgSO$_4$) and evaporated. The residue was purified by flash column chromatography (silica gel; eluent: EtOAc/hexanes 1:2) to give 0.2 g of N-(2,6-dichlorobenzoyl)-4-(2,6-dimethoxyphenyl)-L-phenylalanine methyl ester (7A)

3) The product obtained above (0.1 g) was dissolved in dry THF (5 mL). To the solution was added a solution of LiOH (monohydrate, 12 mg) in 0.5 mL of water and a few drops of MeOH. The mixture was stirred at room temperature for 2 h, and evaporated. The residue was dissolved in water and acidified with 10% citric acid. The separated solid was collected by filtration and dried to give 80 mg of N-(2,6-dichlorobenzoyl)-4-[2,6-dimethoxyphenyl)-L-phenylalanine. $^1$H NMR (300 MHz. DMSO-d$_6$): δ2.9 (dd, 1H), 3.2 (dd, 1H), 3.7 (s, 6H), 4.72 (m, 1H), 6.7 (d, 2H), 7.1–7.5 (m, 8H), 9.1 (d, 1H). ESMS: m/z 474 (MH$^+$) 472 ([M–H]$^-$).

Example 8

N-(2,6-Dichlorobenzoyl)-4-(2-methoxyphenyl)-L-phenylalanine

1) HCl gas was bubbled into an ethanol (35 mL) solution of N-(tert-butoxycarbonyl)-4-bromo-L-phenylalanine (5 g)

and the mixture was left overnight at room temperature. The separated solid was collected by filtration, washed with ether and air-dried to give 3.46 g of the HCl salt of 4-bromo-L-phenylalanine ethyl ester. ESMS: m/z 274 (MH$^+$).

2) DIEA (6.1 mL) was added to a suspension of the HCl salt obtained above (3.2 g) in CH$_2$Cl$_2$ (40 mL) at 0° C. To the mixture was added a solution of 2,6-dichlorobenzoyl chloride (2.0 mL) in CH$_2$Cl$_2$ (5 mL) and the mixture was stirred overnight at room temperature. The solvent was removed and the residue was partitioned between 1N HCl and EtOAc. The organic layer was separated, washed with brine and evaporated. The product was purified by flash column chromatography (silica gel; eluent: hexanes/EtOAc 4:1) to yield 3.9 g of N-(2,6-dichlorobenzoyl)-4-bromo-L-phenylalanine ethyl ester. ESMS: m/z 446 (MH$^+$).

3) Pd(PPh$_3$)$_4$ (1.61 g) was added to a suspension of 2-methoxybenzene boronic acid (1.5 g), K$_2$CO$_3$ (2.83 g) and the product obtained above (3.65 g) in DME (50 mL) under Ar. The mixture was heated at 80° C. for 24 h, cooled, filtered and the solvent was evaporated. The residue was taken up in EtOAc and the EtOAc solution was washed with water, dried and evaporated. The residue was purified by flash column chromatography (silica gel; eluent: hexanes/EtOAc 4:1) to yield 2.1 g of N-(2,6-dichlorobenzoyl)-4-(2-methoxyphenyl)-L-phenylalanine ethyl ester. ESMS: m/z 472 (MH$^+$).

4) A solution of LiOH (monohydrate, 82 mg) in 1 mL of H$_2$O was added to a solution of the product obtained above (0.4 g) in THF/MeOH (5 mL/1 mL) and the mixture was stirred for 1.5 h. The solvent was removed and the residue was dissolved in water. The solution was acidified to pH 2 with 1N HCl and the separated solid was collected by filtration, washed with water and air-dried to give the title compound.

The following compounds (Example 9 to 14) were prepared by a procedure similar to the Example 7.

Example 9

N-(2,6-Dichlorobenzoyl)-4-(2,4-dimethoxyphenyl)-L-phenylalanine

ESMS: m/z 474 (MH$^+$), 472 ([M–H]$^-$).

Example 10

N-(2,6-Dichlorobenzoyl)-4-(2,3,6-trimethoxyphenyl)-L-phenylalanine

ESMS: m/z 504 (MH$^+$), 502 ([M–H]$^-$).

Example 11

N-(2,6-Dichlorobenzoyl)-4-(2,4,6-trimethoxyphenyl)-L-phenylalanine

ESMS: m/z 504 (MH$^+$), 502 ([M–H]$^-$)

Example 12

N-(2,6-Dichlorobenzoyl)-4-(4-chloro-2,6-dimethoxyphenyl)-L-phenylalanine

ESMS: m/z 509 (MH$^+$), 507 ([M–H]$^-$ ).

Example 13

N-(2,6-Dichlorobenzoyl)-4-(2,6-diethoxyphenyl)-L-phenylalanine

ESMS: m/z 502 (MH$^+$), 500 ([M–H]$^-$).

Example 14

N-(2,6-Dichlorobenzoyl)-4-(2-ethoxy-6-methoxyphenyl)-L-phenylalanine

ESMS: m/z 488 (MH$^+$), 486 ([M–H]$^-$)

Example 15

N-(2,6-Dichlorobenzoyl)-4-[2-[N-(tert-butyl)sulfamoyl]phenyl]-L-phenylalanine methyl ester 2-[N-(tert-Butyl)sulfamoyl]benzeneboronic acid (0.4 g) was dissolved in DME (10 mL). To this solution was added K$_2$CO$_3$ (0.1 g), N-(2,6-dichlorobenzoyl)-4-bromo-L-phenylalanine methyl ester (0.1 g), Pd(Ph$_3$P)$_4$ (0.1 g) and water (0.2 mL). The mixture was heated at 80° C. overnight. After cooling, EtOAc and water were added to the mixture. The EtOAc phase was dried (MgSO$_4$), filtered and evaporated. The residue was purified by flash column chromatography (silica gel; eluent: EtOAc/hexanes 1:2) to give 100 mg of the title compound. ESMS: m/z 585 ([M+Na]$^+$).

Example 16

N-(2,6-Dichlorobenzoyl)-4-[2-[N-(tert-butyl)sulfamoyl]phenyl]-L-phenylalanine

N-(2,6-Dichlorobenzoyl)-4-[2-[N-(tert-butyl)sulfamoyl]phenyl]-L-phenylalanine methyl ester (75 mg) was dissolved in THF (5 mL) and to this solution was added a solution of LiOH (monohydrate, 10 mg) in water (0.4 mL). Few drops of MeOH were added and the mixture was stirred at room temperature overnight. The mixture was evaporated, water was added to the residue and the mixture was acidified with 10% citric acid. The separated solid was collected by filtration, washed with water and dried to give 60 mg of the title compound. ESMS: m/z 549 (MH$^+$), 547 ((M–H]$^-$).

Example 17

N-(2,6-Dichlorobenzoyl)-4-(2-sulfamoylphenyl)-L-phenylalanine

1) N-(2,6-Dichlorobenzoyl)-4-[2-[N-(tert-butyl)sulfamoylphenyl]-L-phenylalanine methyl ester (130 mg) was dissolved in TFA (2 mL), to this solution was added anisole (20 $\mu$M) and the mixture was stirred at room temperature for 6 h. TFA was removed under reduced pressure to give 100 mg of N-(2,6-dichlorobenzoyl)-4-(2-sulfamoylphenyl)-L-phenylalanine methyl ester. ESMS: m/z 507 (MH$^+$)

2) The product obtained above (100 mg) was hydrolyzed in a similar manner as described in Example 16 to give 80 mg of the title compound. ESMS: m/z 493 (MH$^+$), 491 ([M–H]$^-$).

Example 18

N-(2,6-Dichlorobenzoyl)-4-[2-(N-benzoylsulfamoyl)phenyl]-L-phenylalanine

1) N-(2,6-Dichlorobenzoyl)-4-(2-sulfamoylphenyl)-L-phenylalanine methyl ester (100 mg) was dissolved in anhydrous pyridine (5 mL). To this solution was added benzoyl chloride (50 $\mu$L) and the mixture was stirred for 12 h at room temperature under N$_2$. EtOAc and satd. NaHCO$_3$ were added to the mixture and the EtOAc phase was washed with 1 N HCl, dried (MgSO$_4$) and evaporated. The residue was purified by flash column chromatography (silica gel;

eluent: EtOAc/hexanes 1:2) to give N-(2,6-dichlorobenzoyl)-4-[2-(N-benzoylsulfamoyl)phenyl]-L-phenylalanine methyl ester.

2) The product obtained above was hydrolyzed in a similar manner as described in Example 16 to give 80 mg of the title compound. ESMS: m/z 595 ([M−H]⁻)

Example 19

N-(2,6-Dichlorobenzoyl)-4-[2-(N-acetylsulfamoyl)phenyl]-L-phenylalanine

The title compound was prepared by a procedure similar to Example 18 by replacing benzoyl chloride with AcCl. ESMS: m/z 533 ([M−H]⁻).

The following compounds (Examples 20 and 21) were prepared by a similar procedure and deprotection method as outlined in Examples 15 and 16, respectively.

Example 20

N-(2,6-Dichlorobenzoyl)-4-[2-(N-methylsulfamoyl)phenyl]-L-phenylalanine

ESMS: m/z 505 ([M−H]⁻).

Example 21

N-(2,6-Dichlorobenzoyl)-4-[2-(N,N-dimethylsulfamoyl)phenyl]-L-phenylalanine

ESMS: m/z 519 ([M−H]⁻).

Example 22

N-(2,6-Dichlorobenzoyl)-4-[2-(tert butoxycarbonylamino)phenyl]-L-phenylalanine 1) 2-(tert-Butoxycarbonylamino)benzeneboronic acid (0.3 g) was coupled with N-(2,6-dichlorobenzoyl)-4-bromo-L-phenylalanine methyl ester (270 mg) by a similar procedure as described in Examples 15 to give 250 mg of N-(2,6-dichlorobenzoyl)-4-[2-(tert-butoxycarbonylamino)phenyl]-L-phenylalanine methyl ester. ESMS: m/z 543 (MH⁺).

2) The product obtained above (40 mg) was hydrolyzed in a similar manner as described in Example 16 to give 35 mg of the title compound. ESMS: m/z 529 (MH⁺), 527 ([M−H]⁻).

Example 23

N-(2,6-Dichlorobenzoyl)-4-(2-aminophenyl)-L-phenylalanine

1) N-(2,6-Dichlorobenzoyl)-4-[2-(tert-butoxycarbonylamino)phenyl]-L-phenylalanine methyl ester (90 mg) was treated with TFA (1 mL) for 2 h at room temperature. Excess TFA was removed in vacuo to give N-(2,6-dichlorobenzoyl)-4-(2-aminophenyl)-L-phenylalanine methyl ester TFA salt.

2) The resulting TFA salt was hydrolyzed in a similar manner as described in Example 16 to give 57 mg of the title compound. ESMS: m/z 429 (MH⁺)

Example 24

N-(2,6-Dichlorobenzoyl)-4-[2-(methanesulfonylamino)phenyl]-L-phenylalanine

1) N-(2,6-Dichlorobenzoyl)-4-(2-aminophenyl)-L-phenylalanine methyl ester TFA salt (90 mg) was dissolved in dry CH₂Cl₂ (5 mL). To this solution was added Et₃N (85 μL) and MsCl (30 μL). The mixture was stirred at room temperature for 3 h and diluted with water. The organic phase was dried (MgSO₄) and evaporated to give N-(2,6-dichlorobenzoyl)-4-[2-(methanesulfonylamino)phenyl]-L-phenylalanine methyl ester.

2) The product obtained above was hydrolyzed in a similar manner as described in Example 16 to give 70 mg of the title compound: ESMS: m/z 507 (MH⁺).

Example 25

N-(2,6-Dichlorobenzoyl)-4-[2-(acetylamino)]phenyl]-L-phenylalanine

1) N-(2,6-Dichlorobenzoyl)-4-(2-aminophenyl)-L-phenylalanine methyl ester TFA salt (90 mg) was dissolved in dry THF (5 mL). Ac₂O (60 μL) and DIEA (160 μL) were added and the mixture was stirred at room temperature for 12 h. EtOAc was added and the resulting mixture was extracted with water. The organic phase was dried (MgSO₄) and evaporated to give N-(2,6-dichlorobenzoyl)-4-[2-(acetylamino)]phenyl]-L-phenylalanine methyl ester.

2) The product obtained above was hydrolyzed in a similar manner as described in Example 16 to give 60 mg of the title compound; ESMS: m/z 471 (MH⁺).

Example 26

N-(2,6-Dichlorobenzoyl)-4-[2-(methoxycarbonylamino)phenyl]-L-phenylalanine

1) N-(2,6-Dichlorobenzoyl)-4-(2-aminophenyl)-L-phenylalanine methyl ester TFA salt (90 mg) was dissolved in THF (5 mL) and to this solution was added DIEA (160 μL) and ClCOOMe (20 μL). The mixture was stirred at room temperature for 12 h. After usual work-up as shown in Example 25, N-(2,6-dichlorobenzoyl)-4-[2-(methoxycarbonylamino)phenyl]-L-phenylalanine methyl ester was obtained.

2) The product obtained above was hydrolyzed in a similar manner as described in Example 16 to give 70 mg of the title compound; ESMS: m/z 487 (MH⁺)

Example 27

N-(2,6-Dichlorobenzoyl)-4-[2-(N,N-dimethylamino)phenyl]-L-phenylalanine

1) N-(2,6-Dichlorobenzoyl)-4-(2-aminophenyl)-L-phenylalanine methyl ester TFA salt (90 mg) was dissolved in EtOH (5 mL). To this solution was added formalin (96 μL), 1 N HCl (234 μL) and NaCNBH₃ (36 mg). The mixture was stirred for 0.5 h at room temperature, then a 1:1 mixture of EtOH (0.5 mL) and 1N HCl (0.5 mL) was added and the mixture was stirred overnight. Additional 1N HCl was added and the mixture was stirred for 0.5 h. The mixture was neutralized with NaHCO₃ and extracted with EtOAc. The combined extracts were dried (MgSO₄) and evaporated to give N-(2,6-dichlorobenzoyl)-4-[2-(N,N-dimethylamino)phenyl]-L-phenylalanine methyl ester.

2) The product obtained above was hydrolyzed in a similar manner as described in Example 16 to give 70 mg of the title compound. ESMS: m/z 457 (MH⁺)

Example 28

N-(2,6-Dichlorobenzoyl)-4-(2-ureidophenyl)-L-phenylalanine

1) N-(2,6-Dichlorobenzoyl)-4-(2-aminophenyl)-L-phenylalanine methyl ester TFA salt (90 mg) was dissolved in dry THF (5 mL). To this solution was added chlorosulfonyl isocyanate (22 μL) and the mixture was stirred at room temperature for 2 h. The mixture was neutralized with NaHCO$_3$ and extracted with EtOAc. The combined organic extracts were dried (MgSO$_4$) and evaporated.

2) The residue was hydrolyzed in a similar manner as described in Example 16 to give, after HPLC purification (60% MeCN, 0.1% CF$_3$COOH, 40% H$_2$O), 30 mg (34%) of the title compound; ESMS: m/z 472 (MH$^+$).

Example 29

N-(2,6-Dichlorobenzoyl)-4-[2-(N,N-dimethylamino)-6-methoxyphenyl]-L-phenylalanine 1) 2-Methoxy-6-(N,N-dimethylamino)benzene boronic acid was coupled with N-(2,6-dichlorobenzoyl)-4-bromo-L-phenylalanine methyl ester to give N-(2,6-dichlorobenzoyl)-4-[2-(N,N-dimethylamino)-6-methoxyphenyl]-L-phenylalanine methyl ester. The preparation of the boronic acid and the coupling reaction was carried out in a similar manner as described in Example 7.

2) The product obtained above was hydrolyzed in a similar manner as described in Example 7 to give the title compound; ESMS: m/z 487 (MH$^+$).

Example 30

N-(2,6-Dichlorobenzoyl)-4-(2-hydroxyphenyl)-L-phenylalanine

1) BBr$_3$ (1 mL, 1M in CH$_2$Cl$_2$) was added to a CH$_2$Cl$_2$ (10 mL) solution of N-(2,6-dichlorobenzoyl)-4-(2-methoxyphenyl)-L-phenylalanine methyl ester (0.215 g) at 0°0 C. with stirring and the solution was slowly warmed to room temperature. The mixture was stirred for 3 h and quenched with EtOH. The solvent was removed and the residue was taken up in EtOAc. The solution was washed with satd. NaHCO$_3$ followed by brine, dried (MgSO$_4$) and evaporated. The residue was purified by flash column chromatography (silica gel; eluent: hexanes/EtOAc 2:1) to yield 0.105 g of N-(2,6-dichlorobenzoyl)-4-(2-hydroxyphenyl)-L-phenylalanine methyl ester. ESMS: m/z 444 (MH$^+$).

2) To a solution of the product obtained above (0.03 g) in THF/MeOH (2 mL/0.2 mL) was added a solution of LiOH (monohydrate, 4 mg) in 0.2 mL of water and the mixture was stirred for 3 h at room temperature. The solvent was removed and the residue was dissolved in water. The mixture was acidified to pH 2 with 1N HCl and the precipitated solid was collected by filtration, washed with water and air dried to give 0.025 g of the title compound. ESMS: m/z 430 (MH$^+$).

Example 31

N-(2,6-Dichlorobenzoyl)-4-(2-hydroxy-6-methoxyphenyl)-L-phenylalanine

1) N-(2,6-Dichlorobenzoyl)-4-(2,6-dimethoxyphenyl)-L-phenylalanine, ethyl ester (0.16 g, prepared in a fashion similar to that of the methyl ester described in Example 8) was dissolved in anhydrous CH$_2$Cl$_2$ (8 mL). The solution was cooled to −78° C. and BBr$_3$ (0.56 mL, 1 M solution in CH$_2$Cl$_2$) was added. The mixture was allowed to warm to 0° C., and stirred at that temperature for 2 h. The mixture was subsequently warmed to room temperature and quenched with satd. NaHCO$_3$ (5 mL). The mixture was stirred for 1 h, and diluted with CH$_2$Cl$_2$. The organic phase was dried (MgSO$_4$) and concentrated. The residue was purified by flash column chromatography (silica gel; eluent: EtOAc/hexanes 1:2) to give 40 mg of N-(2,6-dichlorobenzoyl)-4-(2-hydroxy-6-methoxyphenyl)-L-phenylalanine ethyl ester. ESMS: m/z 488 (MH$^+$).

2) The product obtained above (0.04 g) was hydrolyzed in a similar manner as described in Example 1 to give 35 mg of the title compound. ESMS: m/z 460 (MH$^+$).

Example 32

N-(2,6-Dichlorobenzoyl)-4-[2-(carboxymethoxy)phenyl]-L-phenylalanine

1) To a solution of the product obtained in Example 30-1) (0.1 g) in DMF (2 mL) under N$_2$ was added Cs$_2$CO$_3$ (0.11 g) and the mixture was stirred for 30 min. A solution of BrCH$_2$CO$_2$Me (61 mL) in 1 mL of DMF was added and the mixture was heated at 50° C. for 6 h. DMF was removed and the residue was partitioned between EtOAc and water. The EtOAc layer was washed with brine, dried (MgSO$_4$) and evaporated. The residue was purified by flash column chromatography (silica gel; eluent: hexanes/EtOAc 1:1) to give 0.86 mg of N-(2,6-dichlorobenzoyl)-4-[2-(methoxycarbonylmethoxy)-phenyl]-L-phenylalanine methyl ester. ESMS: m/z 516 (MH$^+$).

2) The product obtained above (0.86 g) was hydrolyzed in a similar manner as described in Example 1 to give 0.6 g of the title compound. ESMS: m/z 488 (MH$^+$).

Example 33

N-(2,6-Dichlorobenzoyl)-4-[2-(cyanomethoxy)phenyl]-L-phenylalanine methyl ester

The title compound was prepared in a similar manner as described for Example 32 starting from N-(2,6-dichlorobenzoyl)-4-(2-hydroxyphenyl)-L-phenylalanine methyl ester and bromoacetonitrile. ESMS: m/z 483 (MH$^+$)

The following compounds were obtained in an analogous manner starting from N-(2,6-dichlorobenzoyl)-4-(2-hydroxyphenyl)-L-phenylalanine methyl ester and reacting with requisite halides.

TABLE 1

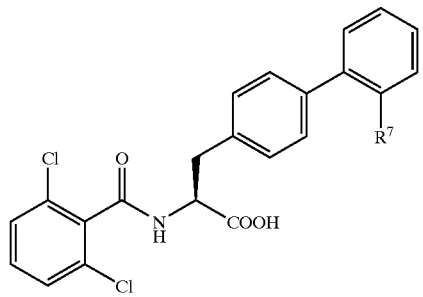

| Examples | R$^7$ | m/z (MH$^+$) |
|---|---|---|
| 34 | —O(CH$_2$)$_3$CH$_3$ | 486 |
| 35 | —OCH$_2$CH(Me)$_2$ | 486 |
| 36 | —O(CH$_2$)$_3$CO$_2$H | 516 |
| 37 | —O(CH$_2$)$_3$OH | 488 |

TABLE 1-continued

[Structure: 2,6-dichlorobenzoyl-NH-CH(COOH)-CH2-(4-phenyl)-biphenyl with R7 on the ortho position of the second phenyl ring]

| Examples | R7 | m/z (MH+) |
|---|---|---|
| 38 | —O-CH2-(2-pyridyl) | 521 |
| 39 | —CH2CH2-(4-pyridyl) | 521 |
| 40 | —O-CH2-(3-pyridyl) | 521 |
| 41 | —O-CH2-(3,5-dimethylisoxazol-4-yl) | 539 |
| 42 | —O-CH2-(2-methylthiazol-5-yl) | 541 |
| 43 | —O-CH2-CH2-(1-methylpyrrolidin-2-yl) | 541 |
| 44 | —O-CH2-(1-methylpiperidin-3-yl) | 541 |

Example 45

N-(2,6-Dichlorobenzoyl)-4-(2-formylphenyl)-L-phenylalanine

1) N-(2,6-Dichlorobenzoyl)-4-(2-formylphenyl)-L-phenylalanine methyl ester was synthesized by following the sequences similar to Example 1 but replacing 2-methoxybenzeneboronic acid with 2-formylbenzeneboronic acid. ESMS: m/z 456 (MH+).

2) The product obtained above (50.4 mg) was dissolved in a mixture of THF (1.33 mL) and MeOR (220 μL). 1M LiOH (220 μL) was added and the resulting mixture was stirred at room temperature under N2 for 2 h. Water was then added and the mixture was acidified (approximately pH 2) with 1N HCl, extracted with EtOAc, dried (MgSO4) and evaporated. The residue was purified by flash column chromatography (silica gel; eluent: CHCl3 then CHCl3/MeOH 10:1) to give the title compound (46.8 mg). ESMS: m/z 442 (MH+).

Example 46

N-(2,6-Dichlorobenzoyl)-4-[2-[(phenylamino)methyl]phenyl]-L-phenylalanine

1) N-(2,6-Dichlorobenzoyl)-4-(2-formylphenyl)-L-phenylalanine methyl ester (49.1 mg) was dissolved in a mixture of anhydrous MeOH (1 mL) and anhydrous THF (0.5 mL). Aniline (58.8 μL), HCl (53.8 μL of 4M in dioxane) and 3 Å molecular sieves were then added and the mixture was stirred under N2 at room temperature for 1 h. NaCNBH3 (4.06 mg) was added and the mixture was stirred for an additional 72 h. The pH of the mixture was brought to approximately 2 with 1N HCl to quench the reaction. The mixture was diluted with water and neutralized with 1M KOH. This was then extracted with CH2Cl2 and the combined organic extracts were dried (K2CO3) and evaporated. The residue was purified by preparative TLC (silica gel) using CH2Cl2 as eluent to give N-(2,6-dichlorobenzoyl)-4-[2-[(phenylamino)methyl]phenyl]-L-phenylalanine methyl ester (21.2 mg). ESMS: m/z 533 (MH+).

2) The product obtained above (21.2 mg) was hydrolyzed in a similar manner as described for Example 1. The mixture was acidified to pH 4–5 with AcOH, extracted with EtOAc (5×20 mL), dried (MgSO4) and evaporated. The residue was purified by silica gel column using CHCl3/MeOH (10:1) as an eluent to give the title compound. ESMS: m/z 519 (MH+).

The following compounds (Examples 47 and 48) were prepared in a similar manner as described in Example 46.

Example 47

N-(2,6-Dichlorobenzoyl)-4-[2-(aminomethyl)phenyl]-L-phenylalanine

ESMS: m/z 443 (MH+).

Example 48

N-(2,6-Dichlorobenzoyl)-4-[2-[(benzylamino)methyl]phenyl]-L-phenylalanine

ESMS: m/z 533 (MH+)

Example 49

N-(2,6-Dichlorobenzoyl)-4-[2-(2-carboxyethenyl)phenyl]-L-phenylalanine

1) N-(2,6-Dichlorobenzoyl)-4-(2-formylphenyl)-L-phenylalanine methyl ester (51.7 mg) and (triphenylphosphoranylidene)acetic acid methyl ester (75.8 mg) were dissolved in anhydrous toluene (1 mL) and stirred at 80° C. under N2 for 18 h. The mixture was allowed to cool and purified by preparative TLC (silica gel) using hexanes/EtOAc (2:1) as eluent to give N-(2,6-dichlorobenzoyl)-4-[2-[2-(methoxycarbonyl)ethenyl]phenyl]-L-phenylalanine methyl ester (48.0 mg). ESMS: m/z 512 (MH+).

2) The product obtained above (26.4 mg) was hydrolyzed with 5 eq. of LiOH H2O in a similar manner as described in Example 1 to give the title compound as a mixture of trans and cis isomers (4:1) (22.0 mg). ESMS: m/z 484 (MH+).

Example 50

N-(2,6-Dichlorobenzoyl)-4-[2-(hydroxymethyl)phenyl]-L-phenylalanine

1) NaBH4 (21 mg) was added to a solution of N-(2,6-dichlorobenzoyl)-4-(2-formylphenyl)-L-phenylalanine methyl ester (0.23 g) in MeOH (5 mL) and the mixture was stirred at room temperature for 3 h. The reaction was quenched with acetone and the mixture was evaporated. The residue was partitioned between EtOAc and water. The EtOAc layer was dried (MgSO$_4$) and evaporated to yield N-(2,6-dichlorobenzoyl)-4-[2-(hydroxymethyl)phenyl]-L-phenylalanine methyl ester (0.24 g). ESMS: m/z 480 ([M+Na]$^+$).

2) The product obtained above was hydrolyzed in a similar manner as described for Example 1 to give the title compound (0.2g). ESMS: m/z 450 ([M+Li]$^+$).

Example 51

N-(2,6-Dichlorobenzoyl)-4-[2-(methoxymethyl) phenyl]-L-phenylalanine.

1) A mixture of N-(2,6-dichlorobenzoyl)-4-[2-(hydroxymethyl)phenyl]-L-phenylalanine methyl ester (0.15 g), CBr$_4$ (0.22 g) and PPh$_3$ (0.173 g) in CH$_2$Cl$_2$ (5 mL) was stirred at room temperature for 18 h. The solvent was evaporated and the residue was purified by flash column chromatography (silica gel; eluent: CH$_2$Cl$_2$/EtOAc 9:1 to 8:1) to yield 0.12 g of N-(2,6-dichlorobenzoyl)-4-[2-(bromomethyl)phenyl]-L-phenylalanine methyl ester. ESMS: m/z 522 (MH$^+$).

2) A mixture of the product obtained above (0.04 g) and NaOMe (0.04 g) in DMF (3 mL) was stirred at room temperature for 18 h. DMF was removed and the residue was partitioned between EtOAc and water. The aqueous layer was separated, adjusted to pH 4 with 1N HCl and extracted with EtOAc. The EtOAc layer was washed with brine, dried (MgSO$_4$) and evaporated. The residue was purified by HPLC (60% MeCN, 0.1% CF$_3$COOH, 40% H$_2$O) to give 9.4 mg of the title compound. ESMS: m/z 480 ([M+Na]$^+$).

Example 52

N-(2,6-Dichlorobenzoyl)-4-(2-carboxyphenyl)-L-phenylalanine

1) N-(2,6-Dichlorobenzoyl)-4-(2-formylphenyl)-L-phenylalanine methyl ester (104 mg) was dissolved in acetone (700 μL) by warming up to about 40° C. A warm (40° C.) solution of KMnO$_4$ (61.2 mg) in a mixture of acetone (900 μL) and water (130 μL) was then added over a 1 h period and the resulting mixture was stirred at that temperature for an additional 2 h. The mixture was filtered through Celite and washed with acetone. The filtrate was taken up with water and acidified to approximately pH 2 with 1N HCl, and extracted with EtOAc. The combined extracts were dried (MgSO$_4$) and evaporated. The residue was purified through a silica gel column using toluene then a gradient of toluene/EtOAc (20:1 to 3:1) as an eluent to give N-(2,6-dichlorobenzoyl)-4-(2-carboxyphenyl)-L-phenylalanine methyl ester (85.0 mg). ESMS: m/z 472 (MH$^+$).

2) The product obtained above was hydrolyzed in a similar manner as described for Example 1 to give the title compound (34.1 mg). ESMS: m/z 458 (MH$^-$).

Example 53

N-(2,6-Dichlorobenzoyl)-4-[2-(N-benzylcarbamoyl) phenyl]-L-phenylalanine

1) N-(2,6-Dichlorobenzoyl)-4-(2-carboxyphenyl)-L-phenylalanine methyl ester (51.9 mg) was dissolved in anhydrous DMF (1 mL) and EDC (25.3 mg), HOBT (20.2 mg), DIEA (28.7 μL) and benzylamine (14.4 μL) were added. The resulting mixture was stirred at room temperature under N$_2$ for 20 h, diluted with EtOAc and washed with 1N HCl, satd. NaHCO$_3$, water and brine. The organic layer was dried (MgSO$_4$) and evaporated. The residue was purified through a silica gel column using hexanes/EtOAc (1:1 to 1:2) as an eluent to give N-(2,6-dichlorobenzoyl)-4-(2-(N-benzylcarbamoyl)phenyl]-L-phenylalanine methyl ester (48.9 mg). ESMS: m/z 561 (MH$^+$).

2) The product obtained above was hydrolyzed in a similar manner as described for Example 1 to give the title compound (34.2 mg). ESMS: m/z 547 (MH$^+$).

The following compounds (Example 54–59) were prepared in an analogous manner as described in Example 53.

Example 54

N-(2,6-Dichlorobenzoyl)-4-[2-(N-methylcarbamoyl) phenyl]-L-phenylalanine

ESMS: m/z 471 (MH$^+$).

Example 55

N-(2,6-Dichlorobenzoyl)-4-[2-(N-n-butylcarbamoyl) phenyl]-L-phenylalanine

ESMS: m/z 513 (MH$^+$).

Example 56

N-(2,6-Dichlorobenzoyl)-4-[2-[N-(2-hydroxyethyl) carbamoyl]phenyl]-L-phenylalanine ESMS: m/z 501 (MH$^+$).

Example 57

N-(2,6-Dichlorobenzoyl)-4-[2-[N-(3-hydroxypropyl) carbamoyl]phenyl]-L-phenylalanine ESMS: m/z 515 (MH$^+$).

Example 58

N-(2,6-Dichlorobenzoyl)-4-[2-(N,N-dimethyl carbamoyl)phenyl]-L-phenylalanine

ESMS: m/z 485 (MH$^+$).

Example 59

N-(2,6-Dichlorobenzoyl)-4-[2-[N-(2-morpholinoethyl)carbamoyl]phenyl]-L-phenylalanine ESMS: m/z 570 (MH$^+$).

Example 60

N-(2,6-Dichlorobenzoyl)-4-[2-(carbamoyl)phenyl)]-L-phenylalanine

1) N-(2,6-dichlorobenzoyl)-4-(2-carboxyphenyl)-L-phenylalanine methyl ester (52.6 mg) was dissolved in anhydrous THF (1 mL), carbonyldiimidazole (36.1 mg) was added and the mixture was stirred at room temperature under N$_2$ for 2 h. Ammonium hydroxide (29% aqueous solution, 135 μL) was added and the mixture was stirred for an additional 22 h. The mixture was then extracted with EtOAc.

The extract was washed with 1N HCl, sat. NaHCO$_3$ and brine, dried (MgSO$_4$) and evaporated. The residue was purified through a silica gel column using toluene/EtOAc (1:1) as an eluent to give N-(2,6-dichlorobenzoyl)-4-(2-carbamoylphenyl)-L-phenylalanine methyl ester (48.1 mg. ESMS: m/z 471 (MH$^+$).

2) The product obtained above was hydrolyzed with 3 eq. of LiOH in a similar manner as described in Example 1 to give the title compound (41.6 mg). ESMS: m/z 457 (MH$^+$).

Example 61

N-(2,6-Dichlorobenzoyl)-4-[2-[(N-methanesulfonyl) carbamoyl]phenyl]-L-phenylalanine 1) N-(2,6-Dichlorobenzoyl)-4-(2-carboxyphenyl)-L-phenylalanine methyl ester (57.0 mg) was dissolved in anhydrous THF (1 mL), carbonyldiimidazole (23.5 mg) was added and the mixture was stirred at room temperature under N$_2$ for 2 h. Methanesulfonamide (17.2 mg) and DBU (27 μL) were added and the mixture was stirred for an additional 18 h. The mixture was then heated to 40° C., stirred for 7 h at the same temperature, cooled to room temperature, diluted with EtOAc, washed with 1N HCl and then brine, dried (MgSO$_4$) and evaporated. The residue was purified by preparative TLC (silica gel) using CH$_2$Cl$_2$/MeOH (100:1 to 10:1) as an eluent to give N-(2,6-dichlorobenzoyl)-4-[2-[N-(methanesulfonyl)carbamoyl]phenyl]-L-phenylalanine methyl ester (37.0 mg). ESMS: m/z 549 (MH$^+$).

2) The product obtained above was hydrolyzed with 3 eq. of LiOH in a similar manner as described in Example 1 to give the title compound (36 mg). ESMS: m/z 535 (MH$^+$).

Example 62

N-(2-Chloro-4-nitrobenzoyl)-4-(2-methoxyphenyl)-L-phenylalanine

1) N-(2-Chloro-4-nitrobenzoyl)-4-(2-methoxyphenyl)-L-phenylalanine methyl ester was prepared in a similar fashion to that described in Example 1-1), 2), 3) and 4) but replacing 2,6-dichlorobenzoyl chloride with 2-chloro-4-nitrobenzoyl chloride.

2) The methyl ester obtained above was then hydrolyzed in a similar manner as described for Example 1-5) to yield the title compound. ESMS: m/z 455 (MH$^+$).

Example 63

N-(4-Amino-2-chlorobenzoyl)-4-(2-methoxyphenyl)-L-phenylalanine

1) Ra—Ni (0.4 mL of 50% dispersion in water) was added to a solution of N-(2-chloro-4-nitrobenzoyl)-4-(2-methoxyphenyl)-L-phenylalanine methyl ester (1.04 g) in anhydrous MeOH (50 mL) and the mixture was stirred at room temperature under H$_2$ atmosphere for 3.5 h. The mixture was then filtered over Celite and washed with MeOH. The filtrate was evaporated and the residue was purified by flash column chromatography (silica gel; eluent: CH$_2$Cl$_2$/MeOH 100:1 to 20:1) to give N-(4-amino-2-chlorobenzoyl)-4-(2-methoxyphenyl)-L-phenylalanine methyl ester (887 mg). ESMS: m/z 439 (MH$^+$). The product obtained above was also prepared via the coupling of 4-(2-methoxyphenyl)-L-phenylalanine methyl ester hydrochloride with 4-amino-2-chlorobenzoic acid using EDC and HOBT in an analogous manner as described in Example 2.

2) The product obtained above (57.0 mg) was hydrolyzed with LiOH in THF/MeOH mixture in a similar manner as described in Example 1-5). The solvent was removed, and the residue was dissolved in water. The mixture was acidified to approximately pH 5 with 10% citric acid, extracted with EtOAc, dried (MgSO$_4$) and evaporated. The residue was purified through a silica gel column using CHCl$_3$/MeOH (10:1) as an eluent to give the title compound (53.9 mg). ESMS: m/z 425 (MH$^+$).

Example 64

N-[2-Chloro-4-(methanesulfonylamino)benzoyl]-4-(2-methoxyphenyl)-L-phenylalanine 1) MeSO$_2$Cl (24 μL) was added to a solution of N-(4-amino-2-chlorobenzoyl)-4-(2-methoxyphenyl)-L-phenylalanine methyl ester (56.0 mg) in anhydrous CH$_2$Cl$_2$ (1 mL) containing DIEA (66.6 μL). The resulting mixture was stirred at room temperature under N$_2$ for 3 h and diluted with CH$_2$Cl$_2$, washed with 1N HCl, water, dried (MgSO$_4$) and evaporated. The residue was purified through a silica gel column using CH$_2$Cl$_2$ as an eluent to give N-[2-chloro-4-(N,N-dimethanesulfonylamino)benzoyl]-4-(2-methoxyphenyl)-L-phenylalanine methyl ester (59.4 mg). ESMS: m/z 595 (MH$^+$).

2) The product obtained above was hydrolyzed with 3 eq. of LiOH in a similar manner as described in Example 1-5) to give the title compound(43.4 mg). ESMS: m/z 503 (MH$^+$).

The following compounds (Examples 65–68) were prepared in an analogous manner as described in Example 64.

Example 65

N-[2-Chloro-4-(trifluoromethanesulfonylamino) benzoyl]-4-(2-methoxyphenyl)-L-phenylalanine ESMS: m/z 557 (MH$^+$). MeSO$_2$Cl was replaced by CF$_3$SO$_2$Cl.

Example 66

N-[2-Chloro-4-(ethoxycarbonylamino)benzoyl]-4-(2-methoxyphenyl)-L-phenylalanine

ESMS: m/z 497 (MH$^+$). MeSO$_2$Cl was replaced by EtO-COCl.

Example 67

N-[2-Chloro-4-(acetylamino)benzoyl]-4-(2-methoxyphenyl)-L-phenylalanine

ESMS: m/z 467 (MH$^+$). MeSO$_2$Cl was replaced by AcCl.

Example 68

N-[2-Chloro-4-(benzenesulfonylamino)benzoyl]-4-(2-methoxyphenyl)-L-phenylalanine ESMS: m/z 565 (MH$^+$). MeSO$_2$Cl was replaced by PhSO$_2$Cl.

Example 69

N-(2-Chloro-4-ureidobenzoyl)-4-(2-methoxyphenyl)-L-phenylalanine

1) Chlorosulfonylisocyanate (16.4 μL) was added to a solution of N-(4-amino-2-chlorobenzoyl)-4-(2-methoxyphenyl)-L-phenylalanine methyl ester (55.2 mg) in anhydrous MeCN (1 mL) and the mixture was stirred at room temperature under $N_2$ for 1 h. Satd. $NaHCO_3$ (40 mL) was added slowly and the mixture was extracted with EtOAc. The extracts were combined, dried ($MgSO_4$) and evaporated. The residue was purified by preparative TLC (silica gel) using $CHCl_3$/MeOH as an eluent.

2) The product obtained above was hydrolyzed with LiOH in a similar manner as described in Example 64 to yield the title compound (24 mg). ESMS: m/z 468 ($MH^+$).

Example 70

N-[2-Chloro-4-(3-methylthioureido)benzoyl]-4-(2-methoxyphenyl)-L-phenylalanine

1) Methylisothiocyanate (43 μL) was added to a solution of N-(4-amino-2-chlorobenzoyl)-4-(2-methoxyphenyl)-L-phenylalanine methyl ester (55.1 mg) in anhydrous DMF (1 mL) containing DIEA (22 μL) and DMAP (catalitic amount). The resulting mixture was then heated at 90° C. under $N_2$ for 1 d. After cooling, the mixture was diluted with EtOAc, washed sequentially with 1N HCl, satd. $NaHCO_3$ and water, dried ($MgSO_4$) and evaporated. The residue was purified by preparative TLC (silica gel) using $CH_2Cl_2$/MeOH (15:1) as an eluent to give N-[2-chloro-4-(3-methylthioureido)benzoyl]-4-(2-methoxyphenyl)-L-phenylalanine methyl ester (22.7 mg). ESMS: m/z 512 ($MH^+$).

2) The product obtained above was hydrolyzed in a similar manner as described in Example 64 to the title compound (22.0 mg). ESMS: m/z 498 ($MH^+$).

Example 71

3-Acetyl-N-(2,6-dichlorobenzoyl)-4-(2-methoxyphenyl)-L-phenylalanine 1) 3-Acetyl-L-tyrosine ethyl ester was prepared by bubbling HCl gas into a solution of 3-acetyl-L-tyrosine (5 g) in ethanol (30 mL). Di-tert-butyl dicarbonate (5 g) was added to a solution of 3-acetyl-L-tyrosine ethyl ester (5 g) in THF (50 mL) and DIEA (10 mL) and the mixture was stirred overnight at room temperature. THF was removed and the residue was partitioned between water and $CH_2Cl_2$. The organic layer was separated, dried ($MgSO_4$) and evaporated. The residue was purified by flash column chromatography (silica gel; eluent: hexanes/EtOAc, 4:1) to yield N-(tert-butoxycarbonyl)-3-acetyl-L-tyrosine ethyl ester (4.3 g). ESMS: m/z 352 ($MH^+$).

2) Anhydrous pyridine (1.1 mL, 12.82 mmol) was added with stirring to a solution of the product obtained above (1.5 g) in $CH_2Cl_2$ (15 mL) at 0° C. Triflic anhydride (1.1 mL) was added dropwise and the mixture was warmed slowly to room temperature and allowed to stir for 24 h. The mixture was diluted with $CH_2Cl_2$, washed sequentially with 1 N HCl, brine, satd $NaHCO_3$ and brine, dried ($MgSO_4$) and evaporated to give N-(tert-butoxycarbonyl)-3-acetyl-O-(trifluoromethanesulfonyl)-L-tyrosine ethyl ester (2.5 g). ESMS: m/z 506 ([M+Na]+).

3) A solution of the product obtained above (0.3 g) in toluene (3 mL) was added with stirring to a solution of 2methoxybenzeneboronic acid (0.13 g) $K_2CO_3$ (0.25 g) in toluene/DMF (4/1 mL) under $N_2$. $Pd(PPh_3)_4$ (0.14 g) was added and the mixture was heated at 85° C. for 48 h. The mixture was cooled, filtered and the solvent was evaporated. The residue was dissolved in EtOAc, washed with water, dried ($MgSO_4$) and evaporated. The residue was purified by flash column chromatography (silica gel; eluent: hexanes/EtOAc, 2.5:1) to yield 0.18 g of 3-acetyl N-(tert-butoxycarbonyl)-4-(2-methoxyphenyl)-L-phenylalanine ethyl ester. ESMS: m/z 442 ($MH^+$).

4) A solution of the product obtained above (0.18 g) in $TFA/CH_2Cl_2$ (8 mL, 50% v/v) was stirred at room temperature for 1 h. The solution was evaporated and dried under high vacuum to give a TFA salt of 3-acetyl-4-(2-methoxyphenyl)-L-phenylalanine ethyl ester.

5) To an ice-cold solution of the TFA salt obtained above in $CH_2Cl_2$ (2 mL) was added DIEA (213 μL) followed by a solution of 2,6-dichlorobenzoyl chloride (65 mL) in $CH_2Cl_2$ (7 mL). The mixture was warmed to room temperature and allowed to stir for 24 h. After the usual work-up as described in Example 1-4) the crude material was purified by flash column chromatography (silica gel; eluent: hexanes/EtOAc, 3:1) to yield 0.142 g of 3-acetyl-N-(2,6-dichlorobenzoyl)-4-(2-methoxyphenyl)-L-phenylalanine ethyl ester. ESMS: m/z 514 ($MH^+$).

6) The product obtained above (0.05 g) was hydrolyzed with LiOH in a similar procedure as described in Example 1-5) to yield 46.5 mg of the title compound. mp. 87–89° C.; ESMS: m/z 486 ($MH^+$).

Example 72

3-Acetyl-N-(2,6-dichlorobenzoyl)-4-phenyl-L-phenylalanine

By substituting 2-methoxybenzeneboronic acid with benzeneboronic acid, the title compound was obtained as a solid in a similar manner as described in Example 71. mp. 109–111° C.; MS: m/z 456 ($MH^+$).

Example 73

N-(2,6-Dichlorobenzoyl)-3-(1-hydroxyethyl)-4-(2-methoxyphenyl)-L-phenylalanine

1) $NaBH_4$ (12 mg) was added to a solution of 3-acety-1N-(2,6-dichlorobenzoyl)-4-(2-methoxyphenyl)-L-phenylalanine ethyl ester (0.1 g) in MeOH (3 mL) and the mixture was stirred at room temperature for 2 h. The mixture was quenched with 1 N HCl and extracted with $CH_2Cl_2$. The extract was washed successively with 1 N HCl and brine, dried and evaporated. The residue was purified by a flash column chromatography (silica gel; eluent: hexanes/EtOAc 3:1) to yield 45 mg of N-(2,6-dichlorobenzoyl)-3-(1-hydroxyethyl)-4-(2-methoxyphenyl)-L-phenylalanine ethyl ester. ESMS: m/z 516 ($MH^+$).

2) The product obtained above (0.040 g) was hydrolyzed with LiOH in a similar manner as described in Example 1-5) to yield 28 mg of the title compound. MS: m/z 488 ($MH^+$).

Example 74

N-(2,6-Dichlorobenzoyl)-3-(1-hydroxyethyl)-4-phenyl-L-phenylalanine

The title compound was prepared from 3-acetyl-N-(2,6-dichlorobenzoyl)-4-phenyl-L-phenylalanine ethyl ester in a similar fashion as described in Example 73. mp. 115–117° C. MS: m/z 458 ($MH^+$).

Example 75

N-(2,6-Dichlorobenzoyl)-3-methoxy-4-(2-methoxyphenyl)-L-phenylalanine 1) 3,4-Dihydroxy-L-phenylalanine methyl ester was prepared by bubbling HCl into a solution of 3,4-dihydroxy-L- phenylalanine (10 g) in methanol (100 mL). Di-tert-butyl dicarbonate (12.1 g) was added to a solution of the ester in THF (250 mL) and DIEA (35.4 mL) and the mixture was warmed for 5 minutes and stirred for 1 h at room temperature. THF was removed and the residue was partitioned between water and ethyl acetate. The organic layer was washed with 1N HCl, brine, dried (MgSO$_4$) and evaporated. The residue was purified by flash column chromatography (silica gel; eluent: hexanes/EtOAc, 1:1) to yield the desired N-(tert-butoxycarbonyl)-3,4-dihydroxy-L-phenylalanine methyl ester (13.4 g). ESMS: m/z 312 (MH$^+$).

2) 2,6-Dichlorobenzyl chloride (1.73 g) was added to a suspension of N-(tert-butoxycarbonyl)-3,4-dihydroxy-L-phenylalanine methyl ester (2.5 g), K$_2$CO$_3$ (2.22 g), and n-Bu$_4$NI (0.297 g) in DMF (15 mL) at room temperature. The mixture was stirred overnight at room temperature, diluted with water and extracted with ether. The extract was dried (MgSO$_4$) and evaporated. The residue was purified by column chromatography (silica gel; eluent: hexanes/CH$_2$Cl$_2$/EtOAc, 5:5:1) to yield N-(tert-butoxycarbonyl)-3,4-bis(2,6-dichlorobenzyloxy)-L-phenylalanine methyl ester (2.0 g), ESMS: m/z 630 (MH$^+$), N-(tert-butoxycarbonyl)-3-(2,6-dichlorobenzyloxy)-4-hydroxy-L-phenylalanine methyl ester (0.39 g), ESMS: m/z 470 (MH$^+$), and N-(tert-butoxycarbonyl)-4-(2,6-dichlorobenzyloxy)-3-hydroxy-L-phenylalanine methyl ester (0.45 g), ESMS: m/z 470 (MH$^+$), respectively.

3) To a suspension of N-(tert-butoxycarbonyl)-4-(2,6-dichlorobenzyloxy)-3-hydroxy-L-phenylalanine methyl ester (0.45 g), K$_2$CO$_3$ (0.199 g), and n-Bu$_4$NI (0.035 g) in DMF (4.0 mL) was added CH$_3$I (0.072 mL) and the mixture was stirred overnight at room temperature. DMF was removed and the residue was partitioned between water and EtOAc. The organic layer was separated and the aqueous solution was extracted with EtOAc. The combined extract was dried (MgSO$_4$) and evaporated. The residue was purified by preparative TLC (silica gel; eluent: hexanes/CH$_2$Cl$_2$/EtOAc, 3:3:1) to yield 0.396 g of N-(tert-butoxycarbonyl)-4-(2,6-dichlorobenzyloxy)-3-methoxy-L-phenylalanine methyl ester. ESMS: m/z 484 (MH$^+$).

4) Hydrogen gas was bubbled to a suspension of the product obtained above (0.39 g), and 10% Pd on activated carbon (0.05 g) in methanol (10 mL) overnight at room temperature. The catalyst was filtered over Celite and the filtrate was evaporated. The residue was purified by preparative TLC (silica gel; eluent: CH$_2$Cl$_2$/MeOH, 10:1) to yield 0.21 g of N-(tert-butoxycarbonyl)-4-hydroxy-3-methoxy-L-phenylalanine methyl ester. ESMS: m/z 348 ([M+Na]$^+$).

5) Anhydrous pyridine (0.15 mL) was added with stirring to a solution of the product obtained above (0.2 g) in CH$_2$Cl$_2$ (3.0 mL) at 0° C. Triflic anhydride (0.16 mL) was added dropwise and the mixture was warmed slowly to room temperature and allowed to stir for 3 hours at room temperature. The mixture was diluted with CH$_2$Cl$_2$ and washed sequentially with 1N HCl, brine, saturated NaHCO$_3$ and brine. The organic layer was dried (MgSO$_4$), and evaporated to give N-(tert-butoxycarbonyl)-3-methoxy-4-trifluoromethanesulfonyloxy-L-phenylalanine methyl ester (0.28 g). ESMS: m/z 457 ([M+Na]$^+$).

6) A solution of the product obtained above (0.28 g) in DME (2.0 mL) was added to a solution of 2-methoxybenzene boronic acid (0.112 g), K$_2$CO$_3$ (0.21 g) in DME (2.0 mL) under N$_2$. Pd(PPh$_3$)$_4$ (0.12 g) was added and the mixture was heated at 65° C. for 48 h, cooled, filtered and the solvent was evaporated. The residue was extracted with EtOAc and the extract was washed with water, dried and evaporated. The residue was purified by preparative TLC (silica gel; eluent: hexanes/EtOAc, 3:1) to yield 0.02 g of N-(tert-butoxycarbonyl)-3-methoxy-4-(2-methoxyphenyl)-L-phenylalanine methyl ester. ESMS: m/z 438 ([M+Na]$^+$).

7) A mixture of the product obtained above (0.055 g) in TFA/CH$_2$Cl$_2$ (1 mL, 50% v/v) was stirred at room temperature for 1 h, evaporated and dried under high vacuum. To an ice-cold solution of the residue in CH$_2$Cl$_2$ (2 mL) was added DIEA (0.069 mL) followed by a solution of 2,6-dichlorobenzoyl chloride (0.02 mL) in CH$_2$Cl$_2$ (1 mL). The mixture was warmed to room temperature and allowed to stir for overnight. After the usual work-up in a similar manner as shown in Example 1, the crude material was purified by preparative TLC (silica gel; eluent: hexanes/EtOAc, 2:1) to yield 0.04 g of N-(2,6-dichlorobenzoyl)-3-methoxy-4-(2-methoxyphenyl)-L-phenylalanine methyl ester. ESMS: m/z 488 (MH$^+$).

8) The product obtained above (0.04 g) was hydrolyzed with LiOH in a similar procedure as described in Example 1-5) to yield 17.8 mg of the title compound. mp. 100–102° C. ESMS: m/z 474 (MH$^+$).

The following compounds were prepared from the corresponding materials in a similar manner as described in one of above Examples.

TABLE 2

| Example | chemical structure | m/z (MH$^+$) |
|---|---|---|
| 76 | 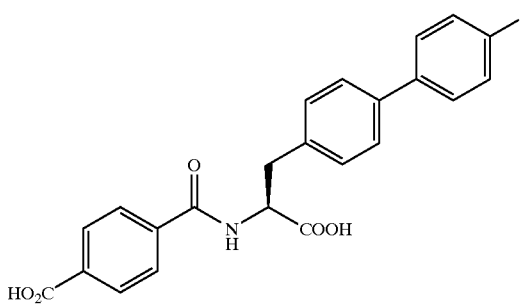 | 419 |

TABLE 2-continued

| Example | chemical structure | m/z (MH+) |
|---|---|---|
| 77 | 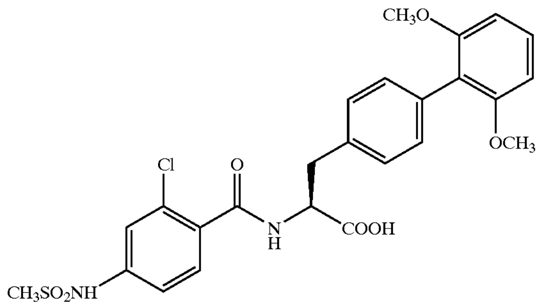 | 533 |
| 78 | 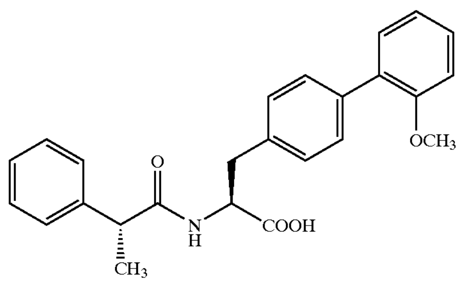 | 403 |
| 79 | 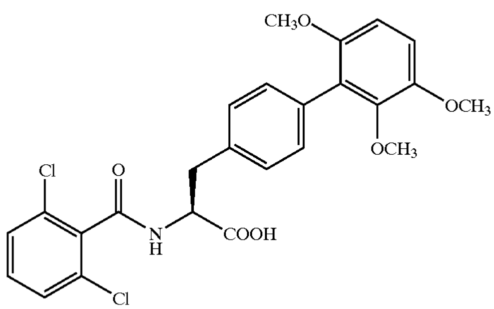 | 518 |
| 80 | 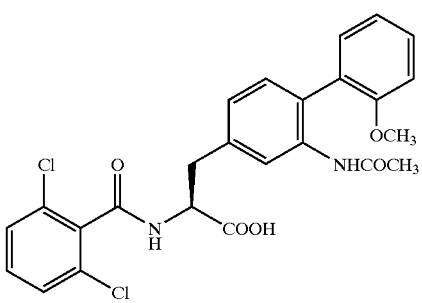 | 501 |
| 81 | 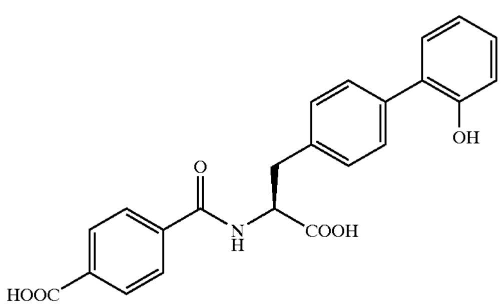 | 405 (M+) |

TABLE 3

| Example | A (R¹, R², R³) | m/z (MH⁺) |
|---|---|---|
| 82 | phenyl | 375 |
| 83 | cyclohexenyl-Cl | 410 |
| 84 | 2,4-dichlorophenyl | 444 |
| 85 | 2,3,5-trichlorophenyl | 479 |
| 86 | 2,6-F, 3-Cl phenyl | 428 |
| 87 | 2,6-difluorophenyl | 411 |
| 88 | 2-CF₃ phenyl | 444 |
| 89 | 2,3-dimethylphenyl | 402 |
| 90 | 2-Cl-3-Me pyridyl | 411 |
| 91 | 4-HO₂C phenyl | 419 |
| 92 | 3-Me-4-CF₃ pyridyl | 444 |
| 93 | 2-Cl-5-Me pyridyl | 411 |
| 94 | 2-Me-5-Me-6-Cl piperidyl | 425 |
| 95 | phenyl-C(O)Me | 403 (M⁺) |
| 96 | 2-Br phenyl | 454 |

TABLE 3-continued
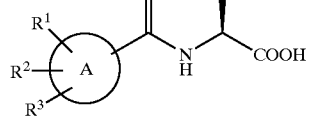
| Example | 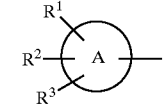 | m/z (MH+) |
|---|---|---|
| 97 | 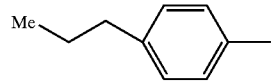 | 417 (M+) |
| 98 |  | 435 (M+) |
| 99 | 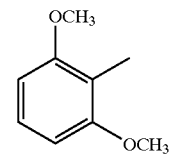 | 405 (M+) |
| 99 | 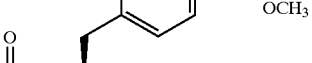 | 458 |
| 101 | 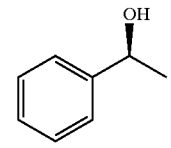 | 420 (M+) |
| 102 |  | 432 |
| 103 | 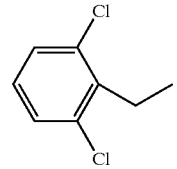 | 377 (M+) |
| 104 | 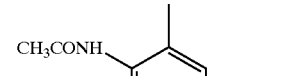 | 433 |
TABLE 3-continued
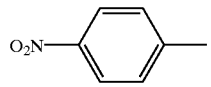
| Example |  | m/z (MH+) |
|---|---|---|
| 105 | 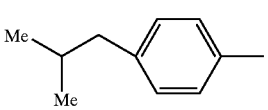 | 433 |
| 106 |  | 563 |
| 107 | 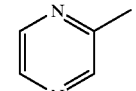 | 563 |
TABLE 4
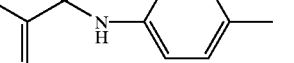
| Example | 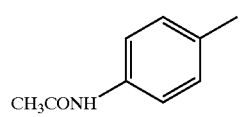 | m/z (MH+) |
|---|---|---|
| 108 | 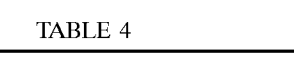 | 399 |

TABLE 4-continued
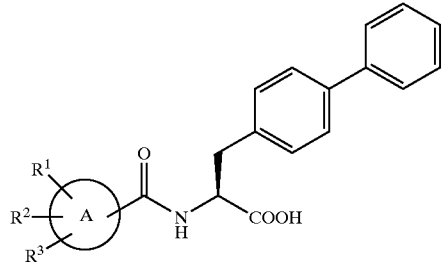
| Example | 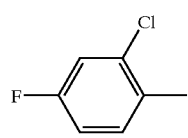 | m/z (MH+) |
|---|---|---|
| 109 | 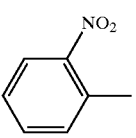 | 398 |
| 110 | 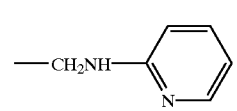 | 390 (M+) |
TABLE 5
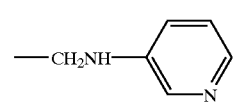
| Example | R⁸ | R⁴ | m/z (MH+) |
|---|---|---|---|
| 111 | —H | —COOH | 414 |
| 112 | —Me | —COOH | 428 |
| 113 | —CF₃ | —COOH | 481 |
| 114 | —CH₂NHCH₂Ph | —COOMe | 547 |
| 115 | 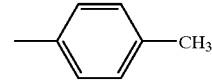 | COOMe | 534 |
| 116 | 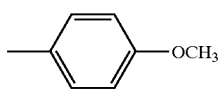 | COOMe | 534 |
TABLE 6
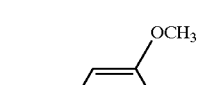
| Example | R⁶ | m/z (MH+) |
|---|---|---|
| 117 | 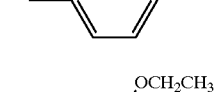 | 428 |
| 118 | 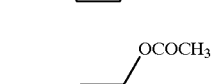 | 444 |
| 119 | 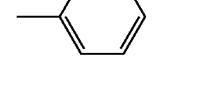 | 444 |
| 120 | 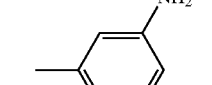 | 458 |
| 121 | 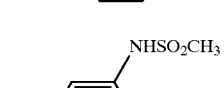 | 456 |
| 122 | 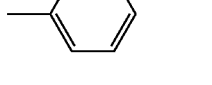 | 429 |
| 123 |  | 507 |
| 124 |  | 471 |
| 125 |  | 487 |

TABLE 6-continued

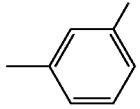

| Example | R⁶ | m/z (MH⁺) |
|---|---|---|
| 126 | NHCO(CH₂)₄CH₃ (3-methylphenyl) | 527 |

TABLE 7

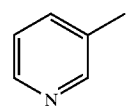

| Example | R⁶ | R⁴ | m/z (MH⁺) |
|---|---|---|---|
| 127 | 3-methylpyridine | COOMe | 429 |
| 128 | 3-methylthiophene | COOH | 420 |
| 129 | 3-methylpyridine | COOH | 415 |
| 130 | 2-methylbenzofuran | COOH | 454 |

TABLE 8

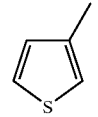

| Example | R⁹ | R¹⁰ | m/z (MH⁺) |
|---|---|---|---|
| 131 | OH | H (CH(OH)CH₃ on R⁹ position: —CH(OH)CH₃) | 518 |
| 132 | H | —CH₂CH₂N(CH₂CH₃)₂ | 559 |
| 133 | H | —CH₂CH₂N(morpholine) | 573 |
| 134 | H | —CH₂CH₂N(thiomorpholine) | 589 |

Example 135

N-(2,6-Dichlorobenzoyl)-4-(2,6-difluorophenyl)-L-phenylalanine

1) N-(2,6-Dichlorobenzoyl)-O-(trifluoromethesulfonyl)-L-tyrosine methyl ester was prepared in a similar method as described in Example 5-1) and 2)

2) To a mixture of the product obtained above (3.00 g), hexamethylditin (1.96 g) and anhydrous LiCl (0.76 g) in dioxane (30 mL) under N₂ was added Pd(PPh₃)₄ (0.34 g) and the mixture was heated at 98° C. for 3 hours. The mixture was cooled, diluted with EtOAc, filtered through Celite and evaporated. The residue was purified by column chromatography (silica gel; eluent: EtOAc/hexane 1/3) to yield 2.46 g of N-(2,6-dichlorobenzoyl)-4-trimethylstannio-L-phenylalanine methyl ester. ESMS: m/z 516 (MH⁺) and 514 (M−H)⁻.

3) To a mixture of the product obtained above (0.17 g) and 1-bromo-2,6-difluorobenzene (95 mg) in toluene (2 mL) under N₂ was added Pd(PPh₃)₄ (0.02 g) and the mixture was heated at 110° C. for 2 hours. The mixture was evaporated. The residue was purified by column chromatography (silica gel; eluent: EtOAc/hexane 1/3) to yield 58 mg of N-(2,6-dichlorobenzoyl)-4-(2,6-difluorophenyl)-L-phenylalanine methyl ester. ESMS: m/z 464 (MH⁺), 486 (M⁺+Na) and 562 (M−H)⁻.

4) The product obtained above (0.058 g) was hydrolyzed with LiOH as described in Example 1-5) to yield the title compound (0.04 g). ESMS: m/z 450 (MH$^+$), 472 (M$^+$+Na) and 448 (M–H)$^-$.

The following compounds (Example 136–140) were prepared in a similar procedure as described in Example 135 but replacing 1-bromo-2,6-difluorobenzene with the requisite bromobenzenes.

TABLE 9

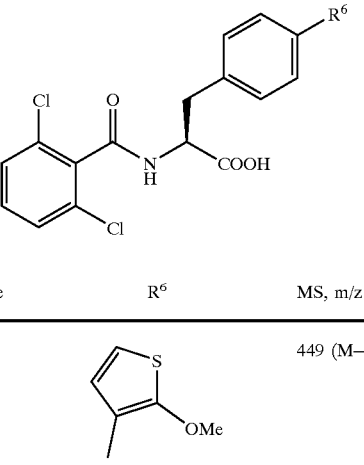

| Example | R$^6$ | MS, m/z |
|---|---|---|
| 136 | 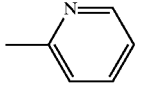 | 449 (M—H)$^-$ |
| 137 | 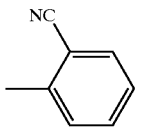 | 415 (MH$^+$) |
| 138 | 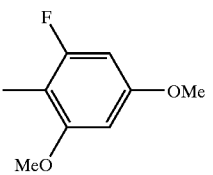 | 439 (MH$^+$) |
| 139 | 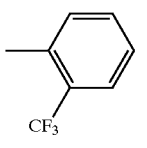 | 492 (MH$^+$) |
| 140 | 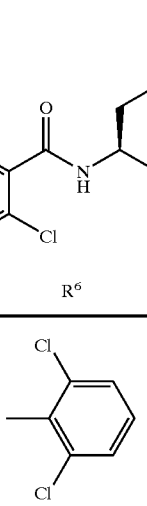 | 498 (MH$^+$) |

TABLE 10

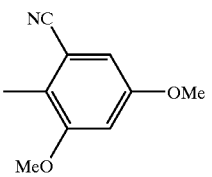

| Example | R$^6$ | MS: m/z | mp: °C. |
|---|---|---|---|
| 141 | 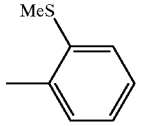 | 484 (MH$^+$) | |
| 142 | 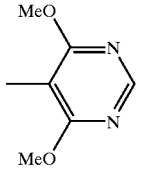 | 499 (MH$^+$) | |
| 143 | 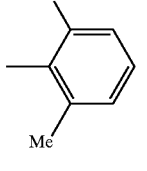 | 460 (MH$^+$) | |
| 144 | 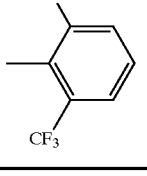 | 476 (MH$^+$) | |
| 145 | Me, Me | 442 (MH$^+$) | 200–201 |
| 146 | CF$_3$, CF$_3$ | 550 (MH$^+$) | 259–260 |

The following compounds (Example 141–146) were prepared in a similar method as described in Example 5 but replacing 2-methoxybenzeneboronic acid with the requisite benzeneboronic acids.

The following compounds (Example 147–149) were prepared in a similar method as described in Example 7 but replacing 1,3-dimethoxybenzene with the requisite benzenes.

TABLE 11

(Structure: 2,6-dichlorobenzoyl-NH-CH(COOH)-CH2-C6H4-R6)

| Example | R6 | MS: m/z | mp: ° C. |
|---|---|---|---|
| 147 | 3,5-di(MeO)-2,6-di(Me)-4-OMe-phenyl | 532(MH+) | 114–115 |
| 148 | 3,5-di(MeO)-2-Me-4-Me-phenyl (see structure) | 488(MH+) | 233–234 |
| 149 | 2,6-di(MeO)-4-n-Pr-phenyl (see structure) | 516(MH+) | 238–239 (dec.) |

Example 150

N-(2,6-Dichlorobenzoyl)-4-(2-cyano-6-carbamoylphenyl)-L-phenylalanine

1) To a mixture of 2,6-dicyanobenzene boronic acid (0.516 g) and anhydrous $K_2CO_3$ (0.52 g) in DME/$H_2O$ (10 mL/0.5 mL) under $N_2$ was added N-(2,6-dichlorobenzoyl)-O-(trifluoromethanesulfonyl)-L-tyrosine methyl ester (0.5 g), The catalyst Pd(PPh$_3$)$_4$ (0.1 g) was added and the mixture was heated at 80° C. for 5 h. The mixture was cooled, diluted with EtOAc and washed successively with water and brine. The organic layer was dried (MgSO$_4$), evaporated, and the residue was purified by column chromatography (silica gel; eluent: EtOAc/hexane 3/1)) to yield 325 mg of N-(2,6-dichlorobenzoyl)-4-(2-cyano-6-carbamoyl-phenyl)-L-phenylalanine methyl ester. ESMS: m/z 496 (MH+), 494 (M−H)−.

2) The product obtained above (150 mg) was hydrolyzed with LiOH as described in Example 1-5) to yield the title compound (0.06 g). MS(m/z) 465 (MH+)

Example 151

N-(2,6-Dichlorobenzoyl)-4-(2,6-dicyanophenyl)-L-phenylalanine

1) To a mixture of 2,6-dicyanobenzene boronic acid (0.516 g) and anhydrous $K_2CO_3$ (0.2 g) in toluene (10 mL) under $N_2$ was added N-(2,6-dichlorobenzoyl)-O-(trifluoromethanesulfonyl)-L-tyrosine methyl ester (0.5 g). Pd(PPh$_3$)$_4$ (0.1 g) was added and the mixture was heated at 90° C. for 8 h. The mixture was cooled, diluted with EtOAc and washed successively with water and brine. The organic layer was dried (MgSO$_4$) and evaporated, and the residue was purified by column chromatography (silica gel; eluent: EtOAc/hexane 1/1) to yield 58 mg of N-(2,6-dichlorobenzoyl)-4-(2,6-dicyanophenyl)-L-phenylalanine methyl ester.

2) The product obtained above was hydrolyzed in a similar procedure as described in Example 1-5) to yield the title compound. MS(m/z) 482 (MH+)

Example 152

N-(2,6-Dichlorobenzoyl)-4-[2-(methylsulfonyl)phenyl]-L-phenyl-alanine (152B), and N-(2,6-dichloro-benzoyl)-4-[2-(methylsulfinyl)phenyl]-L-phenylalanine (152A and 152C)

1) N-(2,6-Dichlorobenzoyl)-4-[2-(methylthio)phenyl]-L-phenyl-alanine methyl ester (0.35 g) was dissolved in $CH_2Cl_2$ (5 mL). mCPBA (50–60%, 0.255 g) was added at 0° C. and the mixture was stirred at 0° C. for 2 h. The mixture was washed successively with aqueous NaHCO$_3$, water and brine, dried (MgSO$_4$), filtered and evaporated. The residue was purified by column chromatography (silica gel; eluent: EtOAc/hexane 1/3) to yield 0.125 g of N-(2,6-dichlorobenzoyl)-4-[2-(methylsulfonyl)phenyl]-L-phenylalanine methyl ester (ESMS (m/z): 506 (MH+), 528 (M++Na), 504 (M+−1)) and 0.227 mg of N-(2,6-dichloro-benzoyl)-4-[2-(methylsulfinyl)phenyl]-L-phenylalanine methyl ester (a mixture of two diastereomers) (ESMS (m/z): 490 (MH+), 512 (M++Na), 488 (M−H)−.

2) N-(2,6-dichlorobenzoyl)-4-[2-(methylsulfonyl)phenyl]-L-phenylalanine methyl ester was hydrolyzed with LiOH as described in Example 1-5) to yield N-(2,6-dichlorobenzoyl)-4-[2-(methylsulfonyl)phenyl]-L-phenylalanine (152B). ESMS: m/z 492 (MH+), 514 (M++Na), 491 (M−H)−.

3) N-(2,6-dichlorobenzoyl)-4-[2-(methylsulfinyl)phenyl]-L-phenylalanine methyl ester (a mixture of two diastereomers) was hydrolyzed with LiOH as described for in Example 1-5) to yield N-(2,6-dichlorobenzoyl)-4-[2-(methylsulfinyl)phenyl]-L-phenylalanine (a mixture of two diastereomers). The mixture was taken up in $CH_2Cl_2$ and the solid was collected by filtration, washed with $CH_2Cl_2$, and dried to yield one diastereomer of N-(2,6-dichlorobenzoyl)-4-[2-(methylsulfinyl)phenyl]-L-phenylalanine (80 mg) (152A). ESMS: m/z 476 (MH+), 498 (M++Na), 474 (M−H)−. $^1$H-NMR (DMSO-d$_6$): δ2.41 (s, 3H), 2.97 (m, 1H), 3.2 (dd, 1H), 4.72 (m, 1H), 7.32 (m, 3H), 7.4 (m, 5H), 7.6–7.7 (m, 2H), 8.0 (d, 1H), 9.15 (d, 1H). The filtrate was evaporated and the residue was crystallized from EtOAc/hexane to afford the other diastereomer of N-(2,6-dichloro-benzoyl)-4-[2-(methylsulfinyl)phenyl]-L-phenylalanine (44 mg) (152C). ESMS: m/z 476 (MH+), 498 (M++Na), 474 (M−H)−. ¯H-NMR (DMSO-d$_6$): δ2.43 (s, 3H), 2.98 (m, 1H), 3.22 (m, 1H), 4.74 (m, 1H), 7.32 (m, 3H), 7.4 (m, 5H), 7.6–7.7 (m, 2H), 8.0 (d, 1H), 9.15 (d, 1H).

Example 153

N-(2,6-Dichlorobenzoyl)-4-(2,6-dimethoxy-3-fluorophenyl)-L-phenylalanine (153A) and N-(2,6-dichlorobenzoyl)-4-(2,6-dimethoxy-3,5-difluorophenyl)-L-phenylalanine (153B)

1) N-(2,6-Dichlorobenzoyl)-4-(2,6-dimethoxyphenyl)-L-phenylalanine methyl ester (232 mg) was dissolved in anhydrous MeCN (10 mL) under N₂ and 3,5-dichloro-1-fluoropyridinium triflate (85%, 353 mg) was added and the mixture was refluxed for 1 day. More 3,5-dichloro-1-fluoropyridinium triflate (175 mg) was added and the mixture was refluxed for another day. The mixture was then concentrated, and the residue was taken up with water and extracted with $CH_2Cl_2$. The extract was washed with sat. $NaHCO_3$, water, dried ($MgSO_4$), filtered and evaporated. The residue was purified by preparative TLC (silica gel; eluent: hexane/AcOEt 5:1 to 2:1) to give N-(2,6-dichlorobenzoyl)-4-(2,6-dimethoxy-3-fluorophenyl)-L-phenylalanine methyl ester(109 mg) and N-(2,6-dichlorobenzoyl)-4-(2,6-dimethoxy-3,5-difluorophenyl)-L-phenylalanine methyl ester (37 mg).

2) The two products obtained above were separately hydrolyzed in a similar method as described in Example 1-5) to give N-(2,6-dichlorobenzoyl)-4-(2,6-dimethoxy-3-fluorophenyl)-L-phenylalanine (mp 228–229° C.; MS m/z 492 (MH⁺)) (153A) and N-(2,6-dichlorobenzoyl)-4-(2,6-dimethoxy-3,5-difluorophenyl)-L-phenylalanine (mp 201–202° C.; MS m/z 510 (MH⁺)) (153B).

Example 154

N-(2,6-Dichlorobenzoyl)-4-(2,3-methylenedioxy-5-fluoro-6-methoxyphenyl)-L-phenylalanine The title compound was prepared in a similar manner as described in Example 153. mp 198–199° C.

Example 155

N-(2,6-Dichlorobenzoyl)-4-[4-(N-allyl-N-tert-butoxycarbonylamino)-2,6-dimethoxyphenyl]-L-phenylalanine 1) 4-(N-Allyl-N-tert-butoxycarbonylamino)-2,6-dimethoxybenzeneboronic acid and N-(2,6-dichlorobenzoyl)-O-(trifluoromethanesulfonyl)-L-tyrosine methyl ester were coupled by a similar method as described in Example 7-2) to give N-(2,6-dichlorobenzoyl)-4-[4-(N-allyl-N-tert-butoxycarbonylamino)-2,6-dimethoxyphenyl]-L-phenylalanine methyl ester.

2) The product obtained above was hydrolyzed in a similar method as described in Example 1-5) to give the title compound; mp 138–139° C.; MS m/z 629 (MH⁺).

Example 156

N-(2,6-Dichlorobenzoyl)-4-(4-allylamino-2,6-dimethoxyphenyl)-L-phenylalanine

1) N-(2,6-Dichlorobenzoyl)-4-[4-[(N-allyl-N-tert-butoxycarbonylamino)-2,6-dimethoxyphenyl]-L-phenylalanine methyl ester (1.25 g) was dissolved in $CH_2Cl_2$ (10 mL) and TFA (10 mL) was added and the mixture was stirred under N₂ at room temperature for 1.5 h. The mixture was evaporated and the residue was taken up with $CH_2Cl_2$, washed with sat. $NaHCO_3$, dried ($MgSO_4$), filtered and evaporated. The residue was purified by column chromatography (silica gel; eluent: hexane/AcOEt 5:1 to 1:1) to give N-(2,6-dichlorobenzoyl)-4-(4-allylamino-2,6-dimethoxyphenyl)-L-phenylalanine methyl ester (938 mg).

2) The product obtained above was hydrolyzed in a similar method as described in Example 1-5) to give the title compound. mp 262–263° C. (dec.); MS m/z 529 (MH⁺).

Example 157

N-(2,6-Dichlorobenzoyl)-4-(4-amino-2,6-dimethoxyphenyl)-L-phenylalanine

1) N-(2,6-Dichlorobenzoyl)-4-(4-allylamino-2,6-dimethoxyphenyl)-L-phenylalanine methyl ester (0.93 g) was dissolved in MeCN/water (40 mL of 84:16) under N₂. Wilkinson's catalyst (79 mg) was added and the mixture was brought to boiling. After 2 h, more catalyst (170 mg) was added and the reaction continued for another 6 h. The solvent was evaporated and the residual water coevaporated with MeCN. The residue was purified by preparative TLC (silica gel; eluent: hexane/AcOEt 2:1 to 1:2) to give N-(2,6-dichlorobenzoyl)-4-(4-amino-2,6-dimethoxyphenyl)-L-phenylalanine methyl ester(708 mg).

2) The product obtained above was hydrolyzed in a similar method as described in Example 1-5) to give the title compound. mp 221–222° C.; MS m/z 489 (MH⁺).

Example 158

N-(2,6-Dichlorobenzoyl)-4-(4-methoxycarbonylamino-2,6-dimethoxyphenyl)-L-phenylalanine The title compound was obtained in a similar procedure as described in Example 64 by reacting N-(2,6-dichlorobenzoyl)-4-(4-amino-2,6-dimethoxyphenyl)-L-phenylalanine methyl ester with MeCOCl instead of $MeSO_2Cl$. mp 235–236° C.; MS m/z 548 (MH⁺)

Example 159

N-(2,6-Dichlorobenzoyl)-4-(4-acetylamino-2,6-dimethoxyphenyl)-L-phenylalanine

The title compound was obtained in a similar procedure as described in Example 64 by reacting N-(2,6-dichlorobenzoyl)-4-(4-amino-2,6-dimethoxyphenyl)-L-phenylalanine methyl ester with MeCOCl instead of $MeSO_2Cl$. mp 243–244° C.; MS m/z 531 (MH⁺).

Example 160

N-(2,6-Dichlorobenzoyl)-4-[4-(3-methylureido)-2,6-dimethoxyphenyl]-L-phenylalanine The title compound was obtained in a similar procedure as described in Example 70 by reacting N-(2,6-dichlorobenzoyl)-4-(4-amino-2,6-dimethoxyphenyl)-L-phenylalanine methyl ester with MeNCO instead of MeNCO. mp 206–207° C.; MS m/z 547 (MH⁺).

Example 161

N-(2,6-Dichlorobenzoyl)-4-[4-[3-(2-methylphenyl)ureido]-2,6-dimethoxyphenyl]-L-phenylalanine The title compound was obtained in a similar procedure as described in Example 70 by reacting N-(2,6-dichlorobenzoyl)-4-(4-amino-2,6-dimethoxyphenyl)-L-phenylalanine methyl ester with 2-methylphenyl isocyanate instead of MeNCS. mp 194–195° C.; MS m/z 622 (MH⁺).

Example 162

N-(2,6-Dichlorobenzoyl)-4-[2,6-dimethoxy-4-(3-methylthioureido)phenyl]-L-phenylalanine The title compound was prepared in a similar manner as described in Example 70 starting from N-(2,6-dichlorobenzoyl)-4-(2,6-dimethoxy-4-aminophenyl)-L-phenylalanine methyl ester. MS m/z 562 (MH⁺), mp. 197–198° C.

Example 163

N-(2,6-Dichlorobenzoyl)-4-[2,6-dimethoxy-4-[(methylsulfonyl)amino]phenyl]-L-phenylalanine The title compound was prepared in a similar manner as described in Example 64 starting from N-(2,6- dichlorobenzoyl)-4-(2,6-dimethoxy-4-aminophenyl)-L-phenylalanine methyl ester. MS m/z 567 (MH⁺), mp. 154–155° C.

Example 164

N-(2,6-Dichlorobenzoyl)-4-[2,6-dimethoxy-4-(dimethylamino)phenyl]-L-phenylalanine The title compound was prepared in a similar manner as described in Example 27 starting from N-(2,6-dichlorobenzoyl)-4-(2,6-dimethoxy-4-aminophenyl)-L-phenylalanine methyl ester. MS m/z 517 (MH⁺)

Example 165

N-(2,6-Dichlorobenzoyl)-4-(4-methylcarbamoyl-2,6-dimethoxyphenyl)-L-phenylalanine 1) 4-(1,3-Dioxolan-2-yl)-2,6-dimethoxybenzeneboronic acid was reacted with N-(2,6-dichlorobenzoyl)-O-(trifluoromethanesulfonyl)-L-tyrosine methyl ester in a similar manner as described in Example 7-2) to give N-(2,6-dichlorobenzoyl)-4-[4-(1,3-dioxolan-2-yl)-2,6-dimethoxyphenyl]-L-phenylalanine methyl ester.

2) The product obtained above was dissolved in THF (60 mL), and 5% HCl (30 mL) was added to the solution. The mixture was stirred under $N_2$ at room temperature for 3 h. The mixture was evaporated, and water (50 mL) was added to the residue. The mixture was extracted with $CH_2Cl_2$, dried ($MgSO_4$), filtered and evaporated. The residue was purified by column chromatography (silica gel; eluent: hexane/AcOEt 2:1to 1:1) to give N-(2,6-dichlorobenzoyl)-4-(4-formyl-2,6-dimethoxphenyl)-L-phenylalanine methyl ester (2.06 g).

The product obtained above was oxidized by a similar as described in Example 52-1) to give N-(2,6-dichlorobenzoyl)-4-(4-carboxy-2,6-dimethoxyphenyl)-L-phenylalanine methyl ester.

4) The product obtained above was reacted with methylamine in a similar procedure as described in Example 53to yield the title compound. MS m/z: 531 (MH⁺); mp 251–252° C.

The following compounds (Example 166-171) were prepared in similar method as described in Example 53, using N-(2,6-dichlorobenzoyl)-4-(4-carboxy-2,6-dimethoxyphenyl) -L-phenylalanine methyl ester and an appropriate amine.

TABLE 12

| Example | R¹¹ | m/z MH⁺ | mp: ° C. |
|---|---|---|---|
| 166 | —CONMe₂ | 545 | 219–221 |
| 167 | —CONHBn | 607 | 153–154 |

TABLE 12-continued

| Example | R¹¹ | m/z MH⁺ | mp: ° C. |
|---|---|---|---|
| 168 | —CONH-i-Pr | 559 | 261–262 |
| 169 | —CONH(CH₂)₃OH | 575 | 222–223 |
| 170 | —CO—N(piperazinyl)N—Me | 614 | 234–235 |
| 171 | —CONH-CH₂CH₂-morpholinyl | 630 | 268–269 |

Example 172

N-(2,6-Dichlorobenzoyl)-4-(4-carboxy-2,6-dimethoxyphenyl)-L-phenylalanine

The title compound was prepared by hydrolyzing N-(2,6-dichlorobenzoyl)-4-(4-carboxy-2,6-dimethoxyphenyl)-L-phenylalanine methyl ester in a similar procedure as described in Example 1-5). MS m/z: 517 (MH⁺); mp 277–278° C.

Example 173

N-(2,6-Dichlorobenzoyl)-4-[4-(methanesulfonylamino)carbonyl-2,6-dimethoxyphenyl]-L-phenylalanine The title compound was obtained in a similar procedure as described in Example 61, using N-(2,6-dichlorobenzoyl)-4-(4-carboxy-2,6-dimethoxyphenyl)-L-phenylalanine methyl ester. MS m/z: 595 (MH⁺); mp 277–278° C.

Example 174

N-(2,6-Dichlorobenzoyl)-4-(2,6-dimethoxy-3-methoxymethoxyphenyl)-L-phenylalanine 1) 2,6-Dimethoxy-3-methoxymethoxybenzeneboronic acid and N-(2,6-dichlorobenzoyl)-O-(trifluoromethanesulfonyl)-L-tyrosine methyl ester were coupled by a similar method as described in Example 7-2) to give N-(2,6-dichlorobenzoyl)-4(2,6-dimethoxy-3-methoxymethoxyphenyl)-L-phenylalanine methyl ester.

2) The product obtained above was hydrolyzed according to the procedure described in Example 7-3) to give the title compound. mp. 156–157° C.; MS m/z 534 (MH⁺).

Example 175

N-(2,6-Dichlorobenzoyl)-4-(2,6-dimethoxy-3-hydroxyphenyl)-L-phenylalanine

1) N-(2,6-Dichlorobenzoyl)-4-(2,6-dimethoxy-3methoxymethoxyphenyl)-L-phenylalanine methyl ester (165 mg) was dissolved in MeOH (5 mL) and HCl in dioxane (4 M, 1 mL) was added to the mixture. The mixture was stirred at room temperature for 3 h. The mixture was evaporated and the residue was taken up with water (40 mL) and extracted with $CH_2Cl_2$. The extract was dried ($MgSO_4$), filtered and evaporated. The residue was purified by preparative TLC (silica gel; eluent: hexane and AcOEt 3:1 to 1:1) to give N-(2,6-dichlorobenzoyl)-4-(2,6-dimethoxy-3-hydroxyphenyl)-L-phenylalanine methyl ester (145 mg).

2) The product obtained above was hydrolyzed in a similar procedure as described in Example 1-5) to give the title compound. mp. 164–165° C.; MS m/z 490 ($MH^+$).

Example 176

N-[2-Chloro-4-(tert-butoxycarbonyl)benzoyl]-4-(2-methoxyphenyl)-L-phenylalanine 1) 2-Chloro-4-(tert-butoxycarbonyl)benzoic acid was coupled with 4-(2-methoxyphenyl)-L-phenylalanine methyl ester (free amine from Example 1-3)) using a similar procedure as described in Example 2-1) to give N-[2-chloro-4-(tert-butoxycarbonyl)benzoyl]-4-(2-methoxyphenyl)-L-phenylalanine methyl ester (0.332 g).

3) The product obtained above (19.8 mg) was hydrolyzed in a similar method as described in Example 1-5) to give the title compound (17.5 mg). MS (m/z): 508 (M–H)$^-$.

Example 177

N-[2-Chloro-4-carboxybenzoyl]-4-(2-methoxyphenyl)-L-phenylalanine

1) N-[2-Chloro-4-(tert-butoxycarbonyl)benzoyl]-4-(2-methoxyphenyl)-L-phenylalanine methyl ester (305 mg) was dissolved in anhydrous $CH_2Cl_2$ (2 mL) under $N_2$ and TFA (2 mL) was added. The mixture was stirred at room temperature for 2 h to give N-[2-chloro-4-carboxybenzoyl]-4-(2-methoxyphenyl)-L-phenylalanine methyl ester (315 mg).

2) The product obtained above (48.6 mg) was then hydrolyzed in a similar procedure as described in Example 1-5) to give N-[2-chloro-4-carboxybenzoyl]-4-(2-methoxyphenyl)-L-phenylalanine (42.9 mg). MS (m/z): 452 (M–H)$^-$.

Example 178

N-[2-Chloro-4-carbamoylbenzoyl]-4-(2-methoxyphenyl)-L-phenylalanine

The title compound was prepared from N-[2-chloro-4-carboxybenzoyl]-4-(2-methoxyphenyl)-L-phenylalanine methyl ester using a similar procedure as described in Example 60. MS (m/z): 451 (M–H)$^-$.

Example 179

N-[2-Chloro-4-[N-(methanesulfonyl)carbamoyl]-benzoyl]-4-(2-methoxyphenyl)-L-phenylalanine The title compound was prepared from N-[2-chloro-4-carboxybenzoyl]-4-(2-methoxyphenyl)-L-phenylalanine methyl ester using a similar procedure as described in Example 61. MS (m/z): 529 (M–H)$^-$.

Example 180

N-[2-Chloro-5-[(trifluoromethanesulfonyl)amino]-benzoyl]-4-(2-methoxyphenyl)-L-phenylalanine The title compound was prepared in similar procedures as described in Examples 62, 63, 64 and 65, but replacing 2-chloro-4-nitrobenzoyl chloride with 2-chloro-5-nitrobenzoyl chloride in the coupling step of Example 62. MS (m/z): 555 (M–H)$^-$

Example 181

N-[2-Chloro-3-[(trifluoromethanesulfonyl)amino]-benzoyl]-4-(2-methoxyphenyl)-L-phenylalanine The title compound was obtained in similar procedures as described in Examples 62, 63, 64 and 65, but replacing 2-chloro-4-nitrobenzoyl chloride with 2-chloro-3-nitrobenzoyl chloride in the coupling step of Example 62. MS (m/z): 555 (M–H)$^-$

Example 182

N-[2,6-Dichloro-4-[(trifluoromethanesulfonyl)amino]benzoyl]-4-(2-methoxyphenyl)-L-phenylalanine The title compound was obtained by successively carrying out similar procedures as described in Examples 62, 63, 64 and 65, except for the use of 2,6-dichloro-4-nitrobenzoic acid (U.S. Pat. No. 3,423,475) in the coupling step of Example 62. MS (m/z): 589 (M–H)$^-$

Example 183

N-[2-Chloro-4-[(trifluoromethanesulfonyl)amino]-benzoyl]-4-(2,6-dimethoxyphenyl)-L-phenylalanine The title compound was obtained by successively carrying out similar procedures as described in Examples 62, 63, 64 and 65, but replacing 4-(2-methoxyphenyl)-L-phenylalanine methyl ester with 4-(2,6-dimethoxyphenyl)-L-phenylalanine methyl ester. MS (m/z): 585 (M–H)$^-$

Example 184

N-[2,6-Dichloro-4-[(trifluoromethanesulfonyl)amino]benzoyl]-4-(2,6-dimethoxyphenyl)-L-phenylalanine The title compound was obtained by successively carrying out similar procedures as described in Examples 62, 63, 64 and 65, but replacing 2,6-dichlorobenzoyl chloride with 2,6-dichloro-4-nitrobenzoyl chloride and replacing 4-(2-methoxyphenyl)-L-phenylalanine methyl ester with 4-(2,6-dimethoxyphenyl)-L-phenylalanine methyl ester. MS (m/z): 619 (M–H)$^-$

Example 185

N-[2-Chloro-6[(trifluoromethanesulfonyl)amino]-benzoyl]-4-(2-methoxyphenyl)-L-phenylalanine The title compound was obtained in similar procedures as described in Examples 62, 63, 64 and 65, except for the use of 2-amino-6-chlorobenzoic acid in the coupling step of Example 62. MS (m/z): 555 (M–H)$^-$

Example 186

N-[2-Chloro-3-[(trifluoromethanesulfonyl)amino]-benzoyl]-4-(2-methoxyphenyl)-D-phenylalanine The title compound was obtained in similar procedures as described in Examples 62, 63, 64 and 65, but starting from 4-(2-methoxyphenyl)-D-phenylalanine methyl ester. MS (m/z): 555 (M–H)$^-$ The following compounds (Examples 187–193) were prepared in similar procedures as described in Examples 62, 63, 64 and 65, but replacing MeSO$_2$Cl with a requisite arylsulfonyl chloride.

Example 187

N-[2-Chloro-4-[[(4-trifluoromethylphenyl)sulfonyl]amino]benzoyl]-4-(2-methoxyphenyl)-L-phenylalanine ESMS m/Z 655 (M$^+$+Na), 633 (MH$^+$), 631 (M–H)$^-$.

Example 188

N-[2-Chloro-4-(tosylamino)benzoyl]-4-(2-methoxyphenyl)-L-phenylalanine

ESMS m/z 601 (M$^+$+Na), 579 (MH$^+$), 577 (M–H)$^-$.

Example 189

N-[2-Chloro-4-[[(4-fluorophenyl)sulfonyl]amino]benzoyl]-4-(2-methoxyphenyl)-L-phenylalanine; ESMS m/z 605 (M$^+$+Na), 583 (MH$^+$), 581 (M–H)$^-$.

Example 190

N-[2-Chloro-4-[[(4-methoxyphenyl)sulfonyl]amino]benzoyl]-4-(2-methoxyphenyl)-L-phenylalanine ESMS m/z 617 (M$^+$+Na), 595 (MH$^+$), 593 (M–H)$^-$.

Example 191

N-[2-Chloro-4-[(2-thienylsulfonyl)amino]benzoyl]-4-(2-methoxyphenyl)-L-phenylalanine ESMS m/Z 593 (M$^+$+Na), 571 (MH$^+$), 569 (M–H)$^-$.

Example 192

N-[2-Chloro-4-[[(2-methylphenyl)sulfonyl]amino]benzoyl]-4-(2-methoxyphenyl)-L-phenylalanine ESMS n/z 601 (M$^+$+Na), 579 (MH$^+$), 577 (M–H)$^-$.

Example 193

N-[2,6-Dichloro-4-[(2-thienylsulfonyl)amino]benzoyl]-4-(2,6-dimethoxyphenyl)-L-phenylalanine; mp. 141–142° C. ESMS m/Z 635 (MH$^+$).

Example 194

N-[4-(3-Benzylthioureido)-2-chlorobenzoyl]-4-(2-methoxyphenyl)-L-phenylalanine

1) A solution of N-(4-amino-2-chlorobenzoyl)-4-(2-methoxyphenyl)-L-phenylalanine (57 mg) in DMF (1.5 mL) was added to a solution of 1,1'-thiocarbonyldiimidazole (28 mg) in DMF (1 mL) under N$_2$ at 0° C. over a 2.5 h period. The mixture was then allowed to warm up slowly to room temperature and stirred for an additional 2 h. Benzylamine (21 µL) was then added and the resulting mixture stirred for 2 h at 80° C. The mixture was concentrated, and the residue was taken up with CH$_2$Cl$_2$ and washed with 1N HCl and water. The organic layer was dried (MgSO$_4$), filtered and evaporated. The residue was purified by preparative TLC (silica gel; eluent: CH$_2$Cl$_2$/MeOH/Et$_3$N 100:1:1) to give a solid. The solid was taken up with CH$_2$Cl$_2$ and washed with 1N HCl, dried and evaporated to give N-[4-(3-benzylthioureido)-2-chlorobenzoyl]-4-(2-methoxyphenyl)-L-phenylalanine methyl ester (42 mg).

2) The product obtained above was hydrolyzed in a similar procedure as described in Example 1-5) to give the title compound (26.9 mg). ESMS m/z 572 (M$^+$–1).

The following compounds (Example 195-198) were prepared in a similar manner as described in Example 70 replacing methyl isothiocyanate with appropriate isothiocyanate.

TABLE 13

| Example | R$^{12}$ | R$^{13}$ | R$^{14}$ | MS: m/z | mp: ° C. |
|---|---|---|---|---|---|
| 195 | i-Pr | H | H | 524 (M-H)$^-$ | |
| 196 | Et | H | H | 510 (M-H)$^-$ | 155–156 |
| 197 | Ph | H | H | 558 (M-H)$^-$ | 145–146 |
| 198 | Me | Cl | —OMe | 546 (M-OH)$^+$ | 189–190 |

The following compounds (Examples 199–204) were prepared in a similar manner as described in Examples 64, 69 or 70.

TABLE 14

| Example | R$^{15}$ | m/z MH$^+$ | mp, ° C. |
|---|---|---|---|
| 199 | Ac | 531 | 227–229 |
| 200 | EtOCO | 561 | 185–187 |
| 201 | MeOCO | 547 | 147–149 |
| 202 | 2-MeC$_6$H$_4$NHCO | 622 | 182–184 |
| 203 | MeNHCO | 546 | 110–112 |
| 204 | H$_2$NCO | 532 | 220–221 |

Example 205

N-(4-Ureido-2,6-dichlorobenzoyl)-4-(3-carbamoyl-2,6-dimethoxyphenyl)-L-phenylalanine The title compound was obtained using a similar procedure as described in Example 69. ESMS m/z 575 (MH$^+$). mp. 217–219° C.

Example 206

N-(4-Amino-2,6-dichlorobenzoyl)-4-(2,6-dimethoxphenyl)-L-phenylalanine

The title compound was prepared in a similar manner as described in Example 63. ESMS m/z 489 (MH⁺). mp. 221–222° C. (dec).

The following compounds (Examples 207–208) were prepared in a similar method as described in Example 2.

TABLE 15

| Example | R¹ | m/z MH⁺ | mp, ° C. |
|---------|-----|---------|----------|
| 207 | Br | 554 | 184–185 |
| 208 | OH | 490 | 252–253 |

The following compounds (Example 209-212) were prepared in a similar manner as described in Example 1 and 2 but replacing 2,6-dichlorobenzoyl chloride and (S)-2-phenylpropionic acid with requisite benzoyl chlorides and benzoic acids.

TABLE 16

| Example | R¹ | R² | m/z MH⁺ | mp ° C. |
|---------|------|-----|---------|---------|
| 209 | OH | Cl | 426 | |
| 210 | H₂NSO₂ | H | 455 | |
| 211 | MeSO₂ | Cl | 488 | |
| 212 | Br | Cl | 490 | 62–63 |

Example 213

N-[2-(2,6-Dichlorophenyl)propionyl]-4-(2-methoxyphenyl)-L-phenylalanine 1) (2,6-Dichlorophenyl)acetic acid (2.55 g) was dissolved in anhydrous MeOH (60 mL) and HCl (gas) was passed through the mixture and the resulting solution was stirred at room temperature for 18 h. The solvent was then evaporated to give (2,6-dichlorophenyl)acetic acid methyl ester (2.7 g).

2) LDA (2 M in heptane/THF/ethyl benzene) was added to THF (10 mL) and the mixture was cooled to −78° C. under N₂. The product obtained above (1.1 g) was added dropwise and the mixture was stirred at −78° C. for 30 min. MeI (0.467 mL) was added and the mixture was allowed to warm up to room temperature and stirred overnight. The mixture was concentrated. The residue was taken up with AcOEt (75 mL), washed successively with 1 N HCl, water and brine. The mixture was dried (MgSO₄), filtered and evaporated to give 2-(2,6-dichlorophenyl)propionic acid methyl ester (1.11 g).

3) The product obtained above was dissolved in THF/MeOH/toluene (65 mL, 11:1:1) and 1 M KOH (9.18 mL) was added. The mixture was stirred at room temperature for 6 h, heated to 50° C. and stirred overnight. EtOH (5 mL) was added and the mixture was stirred at 60° C. for 6 h and refluxed overnight. The mixture was concentrated and taken up with water (60 mL), acidified with 1 N HCl to pH<2. The product was collected by filtration to give 2-(2,6-dichlorophenyl)propionic acid (0.84 g).

4) The product obtained above was coupled with 4-(2-methoxyphenyl)-L-phenylalanine methyl ester by a similar procedure as described in Example 2 and hydrolyzed with LiOH to give the title compound. ESMS m/z 472 (MH⁺). mp. 109–110° C.

The following compounds (Examples 214–217) were prepared in a similar procedure as described in Example 4.

Example 214

N-(2,6-Dichlorobenzoyl)-4-(2-formyl-3-thienyl)-L-phenylalanine

ESMS m/z 470 (M⁺+Na), 448 (MH⁺), 446 (M−H)⁻.

Example 215

N-(2,6-Dichlorobenzoyl)-4-(5-acetyl-2-thienyl)-L-phenylalanine mp. 194–195° C. ESMS m/z 484 (M⁺+Na), 462 (MH⁺), 460 (M−H)⁻.

Example 216

N-(2,6-Dichlorobenzoyl)-4-[(3,5-dimethyl-4-isoxazolyl)-2,6-dimethoxyphenyl]-L-phenylalanine ESMS m/z 433 (MH⁺); mp. 118.7° C.

Example 217

N-(2,6-Dichlorobenzoyl)-4-(4-pyridyl)-L-phenylalanine

ESMS m/z 415 (MH⁺).

Example 218

N-(2,6-Dichlorobenzoyl)-4-(2-hydroxymethyl-3-thienyl)-L-phenylalanine

The title compound was prepared by NaBH₄ reduction of N-(2,6-Dichlorobenzoyl)-4-(2-formyl-3-thienyl)-L-phenylalanine methyl ester followed by hydrolysis as described in Example 50. ESMS m/z 472 (M⁺+Na), 448 (M−H)⁻.

Example 219

N-(2,6-Dichlorobenzoyl)-4-(2-cyano-3-thienyl)-L-phenylalanine

1) A mixture of N-(2,6-dichlorobenzoyl)-O-(trifluoromethane sulfonyl)-L-tyrosine methyl ester (361 mg), trimethyl(2-cyano-3-thienyl)tin (393 mg), Pd(PPh$_3$)$_4$ (42 mg) and LiCl (93 mg) in dioxane (8 mL) was stirred at 100° C. under N$_2$ for 38 h. The mixture was diluted with AcOEt and treated with 10% NH$_4$Cl aqueous solution (6 mL). After stirring at room temperature for 1 h, the mixture was filtered through Celite and washed with AcOEt. The combined organic layers were washed successively with water and brine, dried (MgSO$_4$) and evaporated under reduced pressure. The residue was purified by silica gel chromatography to afford N-(2,6-dichlorobenzoyl)-4-(2-cyano-3-thienyl)-L-phenylalanine methyl ester (126 mg). ESMS m/z 481 (M$^+$+Na), 459 (MH$^+$), 457 (M–H)$^-$.

2) The product obtained above was hydrolyzed with LiOH as described in Example 1-5) to afford N-(2,6-dichlorobenzoyl)-4-(2-cyano-3-thienyl)-L-phenylalanine (110 mg); ESMS m/z 467 (M$^+$+Na), 445 (MH$^+$), 443 (M–H)$^-$.

The following compounds (Example 220-226) were prepared in a similar manner as described in Example 32.

Example 220

N-(2,6-Dichlorobenzoyl)-4-[2,6-dimethoxy-4-(3-thienylmethoxy)phenyl]-L-phenylalanine ESMS m/z 584 (M–H)$^-$.

Example 221

N-(2,6-Dichlorobenzoyl)-4-[2,6-dimethoxy-4-[(2,6-dichlorophenyl)methoxy]phenyl]-L-phenylalanine ESMS m/z 672 (M$^+$+Na), 648 (M–H)$^-$.

Example 222

N-(2,6-Dichlorobenzoyl)-4-[2,6-dimethoxy-4-(2-hydroxyethoxy)phenyl]-L-phenylalanine ESMS m/z 556 (M$^+$+Na), 534 (MH$^+$), 532 (M–H)$^-$.

Example 223

N-(2,6-Dichlorobenzoyl)-4-[2,6-dimethoxy-4-[2-(N,N-dimethylamino)ethoxy]phenyl]-L-phenylalanine ESMS m/z 561 (MH$^+$).

Example 224

N-(2,6-Dichlorobenzoyl)-4-(3-i-propoxyphenyl)-L-phenylalanine

ESMS m/z 494 (M$^+$+Na), 472 (MH$^+$), 470 (M–H)$^-$.

Example 225

N-(2,6-Dichlorobenzoyl)-4-(2-i-propoxyphenyl)-L-phenylalanine

ESMS m/z 494 (M$^+$+Na), 472 (MH$^+$), 470 (M–H)$^-$.

Example 226

N-(2,6-Dichlorobenzoyl)-4-(2-i-propyloxy-6-methoxyphenyl)-L-phenylalanine

ESMS m/z 524 (M$^+$+Na), 500 (M–H)$^-$.

Example 227

N-(2,6-Dichlorobenzoyl)-4-[6-methoxy-2-(2-hydroxyethoxy)phenyl]-L-phenylalanine 1) 6-Methoxy-2-methoxymethoxybenzeneboronic acid (1.92 g) was coupled with N-(2,6-dichlorobenzoyl)-O-(trifluoromethanesulfonyl)-L-tyrosine ethyl ester in a similar procedure as described in Example 5-3) to afford N-(2,6-dichlorobenzoyl)-4-(6-methoxy-2-methoxymethoxyphenyl)-L-phenylalanine ethyl ester (0.942 mg). ESMS m/Z 532 (MH$^+$), 530 (M–H)$^-$.

2) To a solution of N-(2,6-dichlorobenzoyl)-4-(6-methoxy-2-methoxymethoxyphenyl)-L-phenylalanine ethyl ester (938 mg) in EtOH (25 mL) was added HCl (4 N in dioxane, 5 mL), and then the mixture was stirred under N$_2$ for 4 h at room temperature. The mixture was diluted with AcOEt, washed with H$_2$O and brine, dried (MgSO$_4$) and evaporated. The residue was purified by column chromatography (silica gel; eluent: AcOEt/hexane 1:2) to afford N-(2,6-dichlorobenzoyl)-4-(6-methoxy-2-hydoxyphenyl)-L-phenylalanine ethyl ester (795 mg). ESMS m/Z 488 (MH$^+$), 486 (M–H)$^-$.

3) A mixture of the product obtained above(256 mg), 2-bromoethyl acetate (271 mg) and K$_2$CO$_3$ (217 mg) in DMF (5 mL) was stirred at 60° C. under N$_2$ for 15 h. The mixture was diluted with AcOEt, washed with H$_2$O and brine, dried (MgSO$_4$) and evaporated. The residue was purified by column chromatography (silica gel; eluent: AcOEt/hexane 1:5-1:3) to afford N-(2,6-dichlorobenzoyl)-4-[6-methoxy-2-(2-acetoxyethoxy)phenyl]-L-phenylalanine ethyl ester (203 mg).

ESMS m/Z 574 (MH$^+$), 572 (M–H)$^-$.

4) The product obtained above (196 mg) was hydrolyzed with LiOH (29mg) as described in Example 1-5). The crude material was crystallized from CH$_2$Cl$_2$/AcOEt/hexane to afford the title compound (145 mg). mp 158–159° C.; ESMS m/Z 526 (M$^+$+Na), 504 (MH$^+$), 502 (M–H)$^-$.

Example 228

N-(2,6-Dichlorobenzoyl)-4-[6-methoxy-2-(2-fluoroethoxy)phenyl]-L-phenylalanine

The title compound was prepared in a similar method as described in Example 227 but replacing 2-bromoethylacetate with 2-fluoroethyl bromide. mp 206–207° C.; ESMS m/Z 506 (MH$^+$).

The following compounds (Examples 229–232) were prepared in a similar procedure as described in Example 227 using requisite benzeneboronic acid.

TABLE 17

| Example | R$^{16}$ | R$^{17}$ | m/z (MH$^+$) | mp (° C.) |
|---|---|---|---|---|
| 229 | —OCH$_2$CH$_2$OH | —OCH$_2$CH$_2$OH | 534 | 124–125 |
| 230 | —OCH$_2$CF$_3$ | —OCH$_2$CF$_3$ | 610 | 93–94 |
| 231 | —OCH$_2$CN | —OCH$_2$CN | 524 | 175–176 |
| 232 | —OCH$_2$CH$_2$N(CH$_3$)$_2$ | —OH | 517 | 168–169 |

The following compounds (Examples 233–241) were obtained in a similar manner as described in Example 228 using requisite benzeneboronic acid.

Example 233

N-(2,6-Dichlorobenzoyl)-4-[2,3-methylenedioxy-6-(2-methoxyethoxy)phenyl]-L-phenylalanine mp 167–168° C.

ESMS m/Z 532 (MH$^+$).

Example 234

N-(2,6-Dichlorobenzoyl)-4-[2,3-methylenedioxy-6 [2-(N,N-dimethylamino)ethoxy]phenyl]-L-phenylalanine ESMS m/z 545 (MH$^+$), 543 (M–H)$^-$.

Example 235

N-(2,6-Dichlorobenzoyl)-4-[2,3-methylenedioxy-6-(methoxymethoxy)phenyl]-L-phenylalanine ESMS m/z 518 (MH$^+$), 516 (M–H)$^-$.

Example 236

N-(2,6-Dichlorobenzoyl)-4-(2,3-methylenedioxy-6-hydroxyphenyl)-L-phenylalanine

ESMS m/z 474 (MH$^+$).

Example 237

N-(2,6-Dichlorobenzoyl)-4-(2,3-methylenedioxy-6-ethoxyphenyl)-L-phenylalanine

ESMS m/z 502 (MH$^+$).

Example 238

N-(2,6-Dichlorobenzoyl)-4-[2,3-methylenedioxy-6-(2-hydroxyethoxy)phenyl]-L-phenylalanine ESMS m/z 518 (MH$^+$), 516 (M–H)$^-$.

Example 239

N-(2,6-Dichlorobenzoyl)-4-[2,3-methylenedioxy-6-(cyanomethoxy)phenyl]-L-phenylalanine ESMS m/z 513 (MH$^+$).

Example 240

N-(2,6-Dichlorobenzoyl)-4-(2,3-methylenedioxy-6-methoxyphenyl)-L-phenylalanine

ESMS m/z 488 (MH$^+$).

Example 241

N-(2,6-Dichlorobenzoyl)-4-(2,3-ethylenedioxy-6-methoxyphenyl)-L-phenylalanine

ESMS m/z 502(MH$^+$). mp. 218° C.

Example 242

N-(2,6-Dichlorobenzoyl)-4-[2,6-dimethoxy-4-[(methylamino)methyl]phenyl]-L-phenylalanine (TR-14454)

1) A mixture of 2,6-dimethoxy-4-[(t-butyldiphenylsilyloxy)methyl]benzeneboronic acid (5.2 g), N-(2,6-dichlorobenzoyl)-4-bromo-L-phenylalanine ethyl ester (1.71 g), Pd(PPh$_3$)$_4$ (0.44 g) and K$_2$CO$_3$ (1.59 g) in DME/H$_2$O (20 mL/0.5 mL) was heated at 80° C. for 24 h under N$_2$. The mixture was worked up and purified in a similar procedure as described in Example 8-3) to yield 2.9 g of N-(2,6-dichlorobenzoyl)-4-[2,6-dimethoxy-4-[(t-butyldiphenylsilyloxy)methyl]phenyl]-L-phenylalanine ethyl ester. ESMS: m/z 770 (MH$^+$).

2) To an ice-cold solution of the product obtained above (2.9 g) in THF (10 mL) was added tetrabutylammonium fluoride (4.45 mL, 1 M in THF) under N$_2$ and the mixture was stirred for 2 h. THF was evaporated and the residue was purified by preparative TLC (eluent: hexane-hexane/EtOAc 50%) to yield 1.86 g of N-(2,6-dichlorobenzoyl)-4-[2,6-dimethoxy-4-(hydroxymethyl)phenyl]-L-phenylalanine ethyl ester. ESMS: m/z 532 (MH$^+$).

3) A mixture of the product obtained above (1.8 g), CBr$_4$ (2.25 g), Ph$_3$P (1.78 g) in CH$_2$Cl$_2$ (20 mL) was stirred at 0° C. overnight. The solvent was evaporated and the residue was purified by column chromatography (silica gel; eluent: hexane-hexane/EtOAc 10%) to give 0.9 g of N-(2,6-dichlorobenzoyl)-4-[2,6-dimethoxy-4-(bromomethyl)phenyl]-L-phenylalanine ethyl ester. ESMS: m/z 596 (MH$^+$).

4) A mixture of the product obtained above (0.15 g) and MeNH$_2$ (2M THF, 0.8 mL) in CH$_2$Cl$_2$ (3 mL) was stirred at room temperature for 4 h. The crude mixture was purified by preparative TLC (silica gel; eluent: CH$_2$Cl$_2$/EtOH 9.5/5 with few drops of NH$_4$OH) to yield 45 mg of N-(2,6-dichlorobenzoyl)-4-[2,6-dimethoxy-4-[(methylamino)methyl]phenyl]-L-phenylalanine ethyl ester. ESMS: 545 (MH$^+$).

5) The product obtained above (0.093 g) was hydrolyzed with LiOH (2N, 0.175 mL) as described in Example 1-5) to give 75 mg of the title compound; mp. 274° C. ESMS: 517 m/z (MH$^+$).

The following compounds (Examples 243–252) were prepared in an analogous manner as described in Example 242 by replacing MeNH$_2$ with the requisite amines.

TABLE 18

| Example | R$^4$ | R$^{18}$ | Physical properties |
|---|---|---|---|
| 243 | —COOH | pyrrolidin-1-ylmethyl | MS: m/z 557 (MH$^+$) |
| 244 | —COOH | 1,4-dioxa-8-azaspiro[4.5]dec-8-ylmethyl | MS: m/z 629 (MH$^+$) |

TABLE 18-continued

[Structure: 2,6-dichlorobenzamide linked to phenylalanine derivative with biphenyl bearing 2,6-dimethoxy groups and CH2-R18 substituent; R4 on alpha carbon]

| Example | R4 | R18 | Physical properties |
|---|---|---|---|
| 245 | —COOH | 2,6-dimethyl-morpholin-4-yl (—N(CHMe-CH2)2O) | MS: m/z 601 (MH+) |
| 246 | —COOH | —NH(CH2)2OH | MS: m/z 547 (MH+) |
| 247 | —COOH | —N(Me)CH2CH2N(Me)2 | MS: m/z 588 (MH+) |
| 248 | —COOH | 4-methylpiperazin-1-yl | MS: m/z 586 (MH+) |
| 249 | —COOEt | 4-methylpiperazin-1-yl | MS: 614 (MH+) mp. 148–150.5° C. 2HCl salt: mp. 235° C. (dec.) |
| 250 | —COOH | 4-(2-hydroxyethyl)piperazin-1-yl | MS: m/z 616 (MH+) |
| 251 | —COOH | 4-acetylpiperazin-1-yl | MS: m/z 614 (MH+) |
| 252 | —COOH | 4-(2-methyl...)piperazinyl (—N(CH2CH2)2N-CH2CH2Me) | MS: m/z 614 (MH+) |

Example 253

N-(2,6-dichlorobenzoyl)-4-[2,6-dimethoxy-4-(thiomorpholinomethyl)phenyl]-L-phenylalanine 1) A mixture of 2,6-dimethoxy-4-(thiomorpholinomethyl) benzeneboronic acid (1.1 g), N-(2,6-dichlorobenzoyl)-4bromo-L-phenylalanine ethyl ester (0.71 g), Pd(PPh3)4 (1.0 g) and K2CO3 (1.00 g) in DME/H2O (10 mL/0.5 mL) was heated at 80° C. for 6 h under N2. The mixture was worked up and purified according to the procedure described in Example 8-3) to yield 0.15 g of N-(2,6-dichlorobenzoyl)-4-[2,6-dimethoxy-4-(thiomorpholinomethyl)phenyl]-L-phenylalanine ethyl ester. mp. 86–89° C. ESMS: m/z 616 (MH+). HCl salt: mp. 204–205° C.

2) The product obtained above (0.15 g) was hydrolyzed with LiOH as described in Example 1-5) to give 120 mg of the title compound. ESMS: m/z 588 (MH+).

The following compounds (Example 254–261) were prepared in a similar manner as described in Example 242 or 253 from requisite starting materials.

Example 254

N-(2,6-Dichlorobenzoyl)-4-[2,6-dimethoxy-4-[(diethylamino)methyl]phenyl]-L-phenylalanine ESMS: m/z 559 (MH+)

Example 255

N-(2,6-Dichlorobenzoyl)-4-[2,6-dimethoxy-4-[(N,N-dimethylamino)methyl]phenyl]-L-phenylalanine ESMS: m/z 531 (MH+)

Example 256

N-(2,6-Dichlorobenzoyl)-4-[2,6-dimethoxy-4 (piperidinomethyl)phenyl]-L-phenylalanine ESMS: m/z 571 (MH+)

Example 257

N-(2,6-Dichlorobenzoyl)-4-[2,6-dimethoxy-4-(morpholinomethyl)phenyl]-L-phenylalanine ESMS: m/z 573 (MH+)

Example 258

N-(2,6-Dichlorobenzoyl)-4-[2,6-dimethoxy-4-[(4-benzyl-1-piperazinyl)methyl]phenyl]-L-phenylalanine ESMS: m/z 662 (MH+)

Example 259

N-(2,6-Dichlorobenzoyl)-4-[2,6-dimethoxy-4-[(N,N-dimethylamino)methyl]phenyl]-L-phenylalanine ethyl ester hydrochloride ESMS: m/z 560 (MH+); mp. 146.5° C.

Example 260

N-(2,6-Dichlorobenzoyl)-4-[2,6-dimethoxy-4-(piperidinomethyl)phenyl]-L-phenylalanine ethyl ester hydrochloride ESMS: m/z 600 (MH+); mp. 205.5° C.

Example 261

N-(2,6-Dichlorobenzoyl)-4-[2,6-dimethoxy-4-(morpholinomethyl)phenyl]-L-phenylalanine ethyl ester hydrochloride ESMS: m/z 601 (MH+); mp. 177.5° C.

Example 262

N-(2,6-Dichlorobenzoyl)-4-[2,6-dimethoxy-4-[(1-piperazinyl)methyl]phenyl]-L-phenylalanine 1) N-(2,6-Dichlorobenzoyl)-4-[2,6-dimethoxy-4-[(4-tert-butoxycarbonyl-1-piperazinyl)methyl]phenyl]-L- phenylalanine ethyl ester was obtained in a similar method as described in Example 253 by replacing 2,6-dimethoxy-4-(thiomorpholinomethyl)benzeneboronic acid with 2,6-dimethoxy-4-[(4-tert-butoxycarbonyl-1-piperazinyl)methyl] benzeneboronic acid.

2) A solution of the product obtained above (0.09 g) in $CH_2Cl_2$/TFA (5/3 mL) was stirred at room temperature for 3 h. The mixture was evaporated and the residue was partitioned between EtOAc and satd. $NaHCO_3$. The EtOAc layer was washed with water, dried and evaporated to yield 70 mg of N-(2,6-dichlorobenzoyl)-4-[2,6-dimethoxy-4-[(1-piperazinyl)methyl]phenyl]-L-phenylalanine ethyl ester. ESMS: m/z 600 ($MH^+$).

3) The product obtained above was hydrolyzed in a similar method as described in Example 1-5) to give 50 mg the title compound. ESMS: m/z 572 ($MH^+$).

Example 263

N-(2,6-Dichlorobenzoyl)-4-[2,6-dimethoxy-4-(thiomorpholinomethyl)phenyl]-L-phenylalanine S-oxide (263B) and N-(2,6-dichlorobenzoyl)-4-[2,6-dimethoxy-4-(thiomorpholinomethyl)phenyl]-L-phenylalanine S,S-dioxide (263A)

1) To a solution of N-(2,6-dichlorobenzoyl)-4-[2,6-dimethoxy-4-(thiomorpholinomethyl)phenyl]-L-phenylalanine ethyl ester (0.1 g) in $CH_2Cl_2$ (3 mL) at $-10°$ C. under $N_2$ was added mCPBA (40 mg) and the mixture was stirred for 2 h. The mixture was diluted with $CH_2Cl_2$, washed with satd. $NaHCO_3$ and brine, dried, evaporated and purified by a preparative TLC to give N-(2,6-dichlorobenzoyl)-4-[2,6-dimethoxy-4-(thiomorpholinomethyl)phenyl]-L-phenylalanine ethyl ester S-oxide (49 mg; ESMS: M/Z 633 ($MH^+$)) and N-(2,6-dichlorobenzoyl)-4-[2,6-dimethoxy-4-(thiomorpholinomethyl)phenyl]-L-phenylalanine ethyl ester S,S-dioxide (10 mg; ESMS: m/z 649 ($MH^+$)).

2) The two products obtained above were separately hydrolyzed in a similar method as described in Example 1-5) to give N-(2,6-dichlorobenzoyl)-4-[2,6-dimethoxy-4-(thiomorpholinomethyl)phenyl]-L-phenylalanine S-oxide (17 mg; mp. 162.8° C. ESMS: m/z 605 ($MH^+$)) and N-(2,6-dichlorobenzoyl)-4-[2,6-dimethoxy-4-(thiomorpholinomethyl)phenyl]-L-phenylalanine S,S-dioxide(7 mg; mp. 230° C. (dec.) ESMS: m/z 621 ($MH^+$)).

Example 264

N-(2,6-Dichlorobenzoyl)-4-[2,6-dimethoxy-4-[2-(4-methyl-1-piperazinyl)ethyl]phenyl]-L-phenylalanine 1) 2,6-Dimethoxy-4-(2-hydroxyethyl)benzeneboronic acid was coupled with N-(2,6-dichlorobenzoyl)-4-bromo-L-phenylalanine ethyl ester according to the procedure described in Example 8-3) to yield 1.3 g of N-(2,6-dichlorobenzoyl)-4-[2,6-dimethoxy-4-(2-hydroxyethyl) phenyl]-L-phenylalanine ethyl ester. ESMS: m/z 546 ($MH^+$).

2) The product obtained above (1.25 g) was dissolved in $CH_2Cl_2$ and $Ph_3P$ (907 mg) was added, then the solution was cooled to 0° C. $CBr_4$ (1.14 g) was added to the mixture and the mixture was stirred at 0° C. for 2 h. The mixture was partitioned between $H_2O$/EtOAc (20 mL each). The organic layer was separated and the aqueous layer was extracted with EtOAc (3×20 mL). The combined organic layers were dried ($MgSO_4$) and evaporated. The residue was purified by column chromatography (silica gel; eluent: EtOAc/hexane 3/7) to give N-(2,6-dichlorobenzoyl)-4-[2,6-dimethoxy-4-(2-bromoethyl)phenyl]-L-phenylalanine ethyl ester. (1.1 g). ESMS: m/z 610 ($MH^+$).

3) The product obtained above (200 mg) was dissolved in $CH_2Cl_2$ (3 mL) and the N-methylpiperazine (0.11 mL) was added. The mixture was stirred at room temperature for 40 h and evaporated. The residue was purified by column chromatography (silica gel; eluent: $CH_2Cl_2$/EtOH 96/4) to give N-(2,6-dichlorobenzoyl)-4-[2,6-dimethoxy-4-[2-(4-methyl-1-piperazinyl)ethyl]phenyl]-L-phenylalanine ethyl ester (113 mg). ESMS: m/z 628 ($MH^+$).

4) The product obtained above was hydrolyzed with LiOH as described in Example 1-5) to give N-(2,6-dichlorobenzoyl)-4-[2,6-dimethoxy-4-[2-(4-methyl-1-piperazinyl)ethyl]phenyl]-L-phenylalanine. mp. 178.9° C. ESMS: m/z 600 ($MH^+$).

Example 265

N-(2,6-Dichlorobenzoyl)-4-[2,6-dimethoxy-4-(2-piperidinoethyl)phenyl]-L-phenylalanine The title compound was synthesized in a similar manner as described in Example 264 replacing N-methylpiperazine by piperidine. mp. 194.9° C. ESMS m/z: 585 ($MH^+$).

Example 266

N-(2,6-Dichlorothiobenzoyl)-4-(2,6-dimethoxyphenyl)-L-phenylalanine

1) A mixture of N-(2,6-dichlorobenzoyl)-4-(2,6-dimethoxyphenyl)-L-phenylalanine methyl ester (0.25 g) and Lawesson's reagent (2,4-bis(4-methoxyphenyl)-1,3-dithia-2,4-diphosphetane-2,4-disufide; 0.21 g) in xylene (10 mL) was refluxed overnight. The mixture was cooled to about 50° C. and water (15 mL) was added and refluxed for 2 h. The mixture was stirred at room temperature overnight and evaporated. The residue was partitioned between EtOAc and water. The EtOAc layer was washed with water, dried and evaporated to yield 0.25 g of N-(2,6-dichlorothiobenzoyl)-4-(2,6-dimethoxyphenyl)-L-phenylalanine methyl ester. ESMS: m/z 504 ($MH^+$).

2) The product obtained above was hydrolyzed with LiOH as described in Example 1-5). The crude product was purified by column chromatography (silica gel; eluent $CH_2Cl_2$/MeOH 95:5 to $CH_2Cl_2$/MeOH/AcOH 95:5:0.1) to give 25 mg of the title compound. mp. 180.4° C. ESMS: m/z 490 ($MH^+$).

Example 267

N-(2,6-Dichlorobenzoyl)-4-(2,6-dimethoxyphenyl)-L-phenylalanine N-(methylsulfonyl)amide 1) To a solution of N-(2,6-dichlorobenzoyl)-4-(2,6-dimethoxyphenyl)-L-phenylalanine (0.1 g) in THF (5 mL) at 0° C. under $N_2$ was added oxalyl chloride (0.055 mL) followed by a drop of DMF. The solution was stirred at 0° C. for 2 h followed by stirring at room temperature for 2 h. THF was evaporated and fresh THF (5 mL) was added and the solution was evaporated again. This process was repeated one more time and the residue was dried under vacuum to yield N(2,6-dichlorobenzoyl)-4-(2,6-dimethoxyphenyl)-L-phenylalanyl chloride.

2) To a solution of the product obtained above in THF (10 mL) was added $MeSO_2NH_2$ (0.0292 g) followed by DBU (0.035 mL). The mixture was stirred at room temperature for 4 h and heated under reflux for 2 h. The mixture was evaporated and the residue was purified by column chromatography (silica gel; eluent: $CH_2Cl_2$ to $CH_2Cl_2$/MeOH 3%) and recrystallization from $CH_2Cl_2/Et_2O$ to give 25 mg of the title compound. ESMS: m/z 551 (MH$^+$).

Example 268

N-(2,6-dichlorobenzoyl)-4-(2,6-dimethoxyphenyl)-L-phenylalanine N-hydroxyamide $NaHCO_3$ (0.21 g) was added to a solution of $NH_2OH$ HCl (0.14 g) in THF/water (5 mL each) at 0° C. and the mixture was stirred for ½ h. A solution of N-(2,6-dichlorobenzoyl)-4-(2,6-dimethoxyphenyl)-L-phenylalanyl chloride (0.1 g) in THF (5 mL) was added to the mixture at 0° C. and the mixture was stirred overnight at room temperature. The mixture was partitioned between EtOAc and water. The EtOAc layer was washed successively with 1 N HCl and brine, dried and evaporated. The residue was purified by preparative TLC (silica gel; eluent: $CH_2Cl_2$/MeOH 8%) to yield 27 mg of the title compound. ESMS: m/z 489 (MH$^+$).

Example 269

N-(2,6-Dichlorobenzoyl)-4-(2-methoxyphenyl)-L-phenylalanine N-hydroxyamide

1) To a solution of N-(2,6-dichlorobenzoyl)-4-(2-methoxyphenyl)-L-phenylalanine (0.098 g) and tert-butylhydroxylamine (0.047 g) in $CH_2Cl_2$ (5 mL) was added BOP reagent (0.17 g) followed by DIEA (0.1 mL) and the mixture was stirred overnight at room temperature. The mixture was evaporated and the residue was dissolved in EtOAc (30 mL). The EtOAc solution was successively washed with 1 N HCl, satd. $NaHCO_3$, satd. LiCl, dried ($MgSO_4$), and concentrated. The residue was purified by preparative TLC (silica gel; eluent: hexane/EtOAc/$CH_2Cl_2$ 6/1/1) and recrystallization from $CH_2Cl_2$/hexane to give 74 mg of N-(2,6-dichlorobenzoyl)-4-(2-methoxyphenyl)-L-phenylalanine N-(tert-butyl)-N-hydroxyamide. ESMS: m/z 515 (MH$^+$).

2) A solution of the product obtained above (0.030 g) in $CH_2Cl_2$/TFA (3 mL each) was stirred for 72 h at room temperature. The mixture was evaporated and the residue was purified by column chromatography (silica gel; eluent: $CH_2Cl_2$ to $CH_2Cl_2$/MeOH 5%) to give 10 mg of the title compound. ESMS: m/z 459 (MH$^+$).

Example 270

(1S)-N-(2,6-Dichlorobenzoyl)-2-[4-(2,6-dimethoxyphenyl)phenyl]-1-(1H-tetrazol-5-yl)ethylamine The title compound was prepared by following the procedure described in the J. Med. Chem., 41, 1513–1518, 1998.

1) A solution of N-(2,6-dichlorobenzoyl)-4-(2,6-dimethoxyphenyl)-L-phenylalanine (0.17 g), HOBT (0.0.08 g), DIEA (0.19 mL) and 2-cyanoethylamine (0.03 mL) in DMF (5 mL) was stirred at room temperature under $N_2$. EDC (0.14 g) was added after 10 min and the mixture was stirred at room temperature under $N_2$. The mixture was diluted with water and extracted with EtOAc. The extract was washed successively with water, 1 N HCl, satd. $NaHCO_3$ and brine, dried and evaporated to give 0.17 g of N-(2,6-dichlorobenzoyl)-4-(2,6-dimethoxyphenyl)-L-phenylalanine N-(2-cyanoethyl) amide. ESMS : m/z 526 (MH$^+$).

2) $Ph_3P$ (0.21 g) was added to a solution of the product obtained above (0.17 g) in MeCN (10 mL). The mixture was cooled to 0° C., and DIAD (0.16 mL) and $TMSN_3$ (0.11 mL) was added. The mixture was allowed to warm to room temperature, heated to 40° C. for 1 h, cooled to room temperature and stirred overnight. The mixture was partitioned between EtOAc and water. The organic layer was washed with satd. $NaHCO_3$ followed by brine, dried ($MgSO_4$), filtered and evaporated. The residue was purified by column chromatography (silica gel; eluent: EtOAc/hexane 1/1) to yield 0.076 mg of (1S)-N-(2,6-dichlorobenzoyl)-2-[4-(2,6-dimethoxyphenyl)phenyl]-1-[1-(2-cyanoethyl)-1H-tetrazol-5-yl]ethylamine. ESMS: m/z 551 (MH$^+$).

3) To a solution of the product obtained above (0.073 g) in $CHCl_3$ (5 mL) was added DBU (0.059 mL) and the mixture was stirred for 48 h at room temperature under $N_2$. The mixture was diluted with EtOAc, washed with 1N HCl and brine, dried and evaporated to yield 0.067 g of the title compound. ESMS: m/z 498 (MH$^+$).

The following compounds (Example 271–274) were prepared in a similar procedure as described in Example 270-1).

Example 271

N-(2,6-Dichlorobenzoyl)-4-(2,6-dimethoxyphenyl)-L-phenylalanine 2-(dimethylamino)ethyl ester ESMS: m/z 582 (MH$^+$).

Example 272

N-(2,6-Dichlorobenzoyl)-4-(2,6-dimethoxyphenyl)-L-phenylalanine 2-pyridylmethyl ester ESMS: m/z 582 (MH$^+$).

Example 273

N-(2,6-Dichlorobenzoyl)-4-(2,6-dimethoxyphenyl)-L-phenylalanine 3-pyridylmethyl ester ESMS: m/z 582 (MH$^+$).

Example 274

N-(2,6-Dichlorobenzoyl)-4-(2,6-dimethoxyphenyl)-L-phenylalanine 4-pyridylmethyl ester ESMS: m/z 582 (MH$^+$).

Example 275

N-(2,6-Dichlorobenzoyl)-4-(2,6-dimethoxyphenyl)-L-phenylalanine i-propyl ester

HCl gas was bubbled into a solution of N-(2,6-dichlorobenzoyl)-4-(2,6-dimethoxyphenyl)-L-phenylalanine (0.15 g) in THF/2-propanol (2/5 mL) for 15 min and the solution was stirred overnight at room temperature. The mixture was saturated with HCl gas, allowed to stand overnight at room temperature, and evaporated. The residue was partitioned between EtOAc and water. The EtOAc layer was washed with water, dried, evaporated and the residue was purified by column chromatography (eluent: EtOAc/hexane 1/1) and triturated with hexane/$Et_2O$ (5/0.5) to give 0.1 g of the title compound. ESMS: m/z 516 (MH$^+$).

Example 276

N-(2,6-Dichlorobenzoyl)-4-(2,6-dimethoxyphenyl)-L-phenylalanine cyclohexyl ester The title compound was prepared in an analogous manner to Example 275 by replacing 2-propanol with cyclohexanol. ESMS: m/z 556 (MH$^+$).

The following compounds (Examples 277–286) were prepared in a similar method as described in Example 1 or Example 2, replacing 2,6-dichlorobenzoic acid or 2,6-benzoyl chloride with an appropriate substituted benzoic acid or acid chloride thereof.

TABLE 19

[Structure: MeO- and OMe-substituted biphenyl linked to CH2-CH(NH-C(O)-A(R1,R2,R3))-COOH]

| Example | $R^2\text{-}A(R^1)(R^3)$ | m/z MH⁺ |
|---|---|---|
| 277 | 2-Cl, 3-Me phenyl | 455 |
| 278 | 2,6-diBr phenyl | 564 (M-H)⁻ |
| 279 | 2,4,6-triF, 3-Me phenyl | 460 |
| 280 | 2-i-Pr phenyl | 448 |
| 281 | 3,5-diMe phenyl | 420 |
| 282 | 3-CN, 5-Me phenyl | 431 |
| 283 | 3-MeO, 5-Me phenyl | 438 |

TABLE 19-continued

[Structure: MeO- and OMe-substituted biphenyl linked to CH2-CH(NH-C(O)-A(R1,R2,R3))-COOH]

| Example | $R^2\text{-}A(R^1)(R^3)$ | m/z MH⁺ |
|---|---|---|
| 284 | 3-O2N phenyl | 451 |
| 285 | 3-Cl, 4-Me, i-PrO phenyl | 498 |
| 286 | 3-Cl, 4-Me, n-PrO phenyl | 498 |

The following compounds (Examples 287–290) were prepared in an analogous manner as described in Example 2 by replacing (S)-2-phenylpropionic acid with properly substituted 2-chlorobenzoic acids.

TABLE 20

[Structure: 2-Cl, 4-R1 benzoyl-NH-CH(COOH)-CH2-phenyl-phenyl-OMe]

| Example | $R^1$ | m/z |
|---|---|---|
| 287 | N-pyrrolyl | 475 (MH⁺) |

TABLE 20-continued

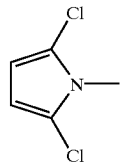

| Example | R¹ | m/z |
|---|---|---|
| 288 | 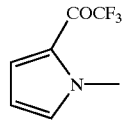 | 543 (MH⁺) |
| 289 | 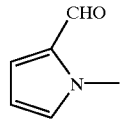 | 569 (M-H)⁻ |
| 290 | 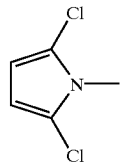 | 501 (M-H)⁻ |

Example 291

N-[2-Chloro-4-(2-hydroxymethyl-1-pyrrolyl)benzoyl]-4-(2-methoxyphenyl)-L-phenylalanine The title compound was obtained from N-[2-chloro-4-(2-formyl-1-pyrrolyl)benzoyl]-4-(2-methoxyphenyl)-L-phenylalanine methyl ester by reduction with NaBH₄ followed by saponification with LiOH as described in Example 50. MS m/z: 503 (M–H)⁻.

The following compounds (Example 292–293) were prepared in a similar method as described in Example 2.

TABLE 21

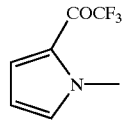

| Example | R¹ | m/z |
|---|---|---|
| 292 | 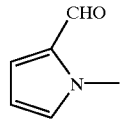 | 510 |
| 293 | | 493 |

Example 294

N-(2,6-Dichlorobenzoyl)-3-[5-(2,6-dimethoxyphenyl)-2-thienyl]-L-alanine

1) N-(9-Fluorenylmethoxycarbonyl)-3-(5-bromo-2-thienyl)-L-alanine (813 mg) was dissolved in EtOH (15 mL) and HCl (gas) was bubbled through the solution for 5 min at 0° C. The mixture was warmed to 50° C. and stirred for 1 h. After cooling to room temperature the solvent was evaporated. The residue was purified by column chromatography (silica gel; eluent: hexane to hexane/EtOAc 1:1) provided N-(9-fluorenylmethoxycarbonyl)-3-(5-bromo-2-thienyl)-L-alanine ethyl ester (767 mg): ESMS: m/z 500 MH⁺.

2) Piperidine (1 mL) was added to a solution of the product obtained above (758 mg) in CH₂Cl₂ (10 mL). The mixture was warmed to 45° C., stirred for 2 h, and evaporated. The residue was dissolved in CH₂Cl₂ (10 mL) and Et₃ᵤN (1.1 mL). To this solution 2,6-dichlorobenzoyl chloride (240 µL) was added and the mixture was stirred at room temperature overnight. 1 N HCl (20 mL) was added and the mixture was extracted with EtOAc. The extract was dried (Na₂SO₄), filtered and evaporated. The residue was purified by column chromatography (silica gel; eluent: hexane to hexane/EtOAc 1:1) to give N-(2,6-dichlorobenzoyl)-3-(5-bromo-2-thienyl)-L-alanine ethyl ester (650 mg): ESMS: m/z 450 (MH⁺).

3) The title compound was prepared from the product obtained above by following procedures described in Example 7-2) and 3). ESMS: m/z 480 (MH⁺). mp. 134° C. (dec.)

Example 295

N-(2,6-Dichlorobenzoyl)-4-(2,6-dimethoxyphenyl)-L-homophenylalanine

The title compound was prepared in a similar manner as described in Example 5. ESMS: m/z 488 (MH⁺). mp. 105–107° C.

Example 296

N-(2,6-Dichlorobenzoyl)-3-ethyl-4-(2-methoxyphenyl)-L-phenylalanine

1) To a solution of N-(2,6-dichlorobenzoyl)-3-(1-hydroxyethyl)-4-(2-methoxyphenyl)-L-phenylalanine ethyl ester (0.08 g) in $CH_3CN$ (3 mL) at 0° C. was added $Et_3SiH$ (0.075 mL) followed by $BF_3.Et_2O$ (0.0197 mL). The mixture was warmed to room temperature and stirred for 1 h. The reaction was quenched with $CH_3OH/H_2O$ and the mixture was extracted with $CH_2Cl_2$. The organic layer was dried ($MgSO_4$), filtered and evaporated. The residue was purified by preparative TLC (silica gel; eluent: EtOAc/hexane 1/2) to give 39 mg of N-(2,6-dichlorobenzoyl)-3-ethyl-4-(2-methoxyphenyl)-L-phenylalanine ethyl ester. ESMS: m/z 500 ($MH^+$).

2) The product obtained above was hydrolyzed with LiOH as described in Example 1-5) to give 30 mg of the title compound. mp. 105–107° C. ESMS: m/z 472 ($MH^+$).

Example 297

N-(2,6-Dichlorobenzoyl)-4-(2,6-dimethoxyphenyl)-3-acetylamino-L-phenylalanine 1) N-(2,6-Dichlorobenzoyl)-4-(2,6-dimethoxyphenyl)-3-nitro-L-phenylalanine ethyl ester was prepared in a similar manner as described in Example 1 by replacing N-(tert-butoxycarbonyl)-L-tyrosine ethyl ester with N-tert-butoxycarbonyl-3-nitro-L-tyrosine ethyl ester.

2) The product obtained above (1.07 g) was dissolved in MeOH (15 mL) under $N_2$. Raney-Ni (100 mg) was added and $H_2$ gas was bubbled through the mixture for 15 min. Stirring under $H_2$ was continued for 6 h. The mixture was filtered through Celite and washed with MeOH. The filtrate was evaporated. The residue was purified by column chromatography (silica gel; eluent: hexane to hexane/EtOAc 1:1) to give N-(2,6-dichlorobenzoyl)-4-(2,6-dimethoxyphenyl)-3-amino-L-phenylalanine ethyl ester (845 mg): ESMS: m/z 503 $MH^+$.

3) The product obtained above (119 mg) was dissolved in $CH_2Cl_2$ (1 mL) and pyridine (57 µL). To this solution was added acetic anhydride (45 µL) and the mixture was stirred at room temperature for 18 h. The mixture was evaporated and the residue was purified by column chromatography (silica gel; eluent: hexane to EtOAc) to give N-(2,6-dichlorobenzoyl)-4-(2,6-dimethoxyphenyl)-3-acetylamino-L-phenylalanine ethyl ester (127 mg): ESMS: m/z 545 ($MH^+$).

4) The product obtained above (126 mg) was hydrolyzed with LiOH as described in Example 1-5) to give the title compound (98 mg): mp. 142–144° C.; ESMS: m/z 531 ($MH^+$).

The following compounds (Examples 298–300) were prepared in a similar method as described in Example 297.

TABLE 22

| Example | $R^5$ | m/z $MH^+$ | mp, ° C. |
|---|---|---|---|
| 298 | $CH_3SO_2NH$ | 567 | 118–120 |
| 299 | EtOCONH | 561 | 216–217 |

Example 300

N-(2,6-dichlorobenzoyl)-3-(2-oxo-1-pyrrolidinyl)-4-(2,6-dimethoxyphenyl)-L-phenylalaine 1) To a solution of N-(2,6-dichlorobenzoyl)-3-nitro-4-(2,6-dimethoxyphenyl)-L-phenylalanine methyl ester (1.07 g) in MeOH (15 mL) was added Raney-Ni (100 mg) and $H_2$ gas was bubbled through the mixture for 15 min. The mixture was filtered through Celite and the filtrate was evaporated under reduced pressure. The residue was purified by column chromatography (silica gel; eluent: hexane to hexane/EtOAc 1:1) to give N-(2,6-dichlorobenzoyl)-3-amino-4-(2,6-dimethoxyphenyl)-L-phenylalanine methyl ester (845 mg). ESMS: m/z 503 ($MH^+$).

2) To a solution of the product obtained above (122 mg) in $CH_2Cl_2$ (1 mL) and pyridine (78 µL) was added 4-chlorobutyryl chloride (54 µL). The mixture was stirred at room temperature for 12 hours and concentrated under reduced pressure. The residue was purified by column chromatography (silica gel; eluent: hexane to EtOAc) to give N-(2,6-dichlorobenzoyl)-3-(4-chlorobutyrylamino)-4-(2,6-dimethoxyphenyl)-L-phenylalanine methyl ester (56 mg). ESMS: m/z 607 ($MH^+$).

3) To a solution of the product obtained above (56 mg) in DMF (1 mL) was added NaH (11 mg. 60% in oil), and the mixture was stirred at room temperature for 30 min. 1N HCl was added to the mixture and the mixture was extracted with EtOAc. The extract was dried ($Na_2SO_4$) and evaporated. The residue was purified by column chromatography (silica gel; eluent: $CH_2Cl_2$ to MeOH/$CH_2Cl_2$ 10%) to give the title compound (23 mg). ESMS: m/z 557 ($MH^+$).

The following compounds (Examples 301–302) were prepared in a similar manner as described in Example 2 by replacing 2-phenylpropionic acid with the requisite benzoic acid and replacing 4-(2-methoxyphenyl)-L-phenylalanine methyl ester hydrochloride with 4-(2,6-dimethoxyphenyl)-L-phenylalanine methyl ester hydrochloride.

Example 301

N-(2,6-Dichloro-4-phenylbenzoyl)-4-(2,6-dimethoxyphenyl)-L-phenylalanine

ESMS: m/z 550 ($MH^+$); mp. 215° C.

Example 302

N-[2,6-Dichloro-4-(1-methyl-2-pyrrolyl)benzoyl]-4-(2,6-dimethoxyphenyl)-L-phenylalanine ESMS: m/z 553 ($MH^+$) mp. 199° C.

Example 303

N-[4-(2-Pyrrolyl)-2,6-dichlorobenzoyl]-4-(2,6-dimethoxyphenyl)-L-phenylalanine

1) N-(4-Bromo-2,6-dichlorobenzoyl)-4-(2,6-dimethoxyphenyl)-L-phenylalanine methyl ester (0.410 g) was coupled with 1-tert-butoxycarbonyl-2-pyrroleboronic acid (0.930 g) in THF (10 mL) as described in Example 7-2) to give 0.435 g of N-[4-(1-tert-butoxycarbonyl-2-pyrrolyl)-2,6-dichlorobenzoyl]-4-(2,6-dimethoxyphenyl)-L-phenylalanine methyl ester. ESMS: m/z 653 (MH$^+$).

2) The compound obtained above was treated with TFA as described in Example 1-3) to give N-[4-(2-pyrrolyl)-2,6-dichlorobenzoyl]-4-(2,6-dimethoxyphenyl)-L-phenylalanine methyl ester (0.198 g). ESMS: m/z 553 (MH$^+$).

3) The product obtained above (0.170 g) was hydrolyzed with LiOH as described in Example 1-5) to yield the title compound (0.127 g). ESMS: m/z 539 (MH$^+$). mp. 250° C.

Example 304

N-[4-(5-Pyrazolyl)-2,6-dichlorobenzoyl]-4-(2,6-dimethoxyphenyl)-L-phenylalanine

1) N-(4-Bromo-2,6-dichlorobenzoyl)-4-(2,6-dimethoxyphenyl)-L-phenylalanine methyl ester (0.240 g) was coupled with 1-[[2-(trimethylsilyl)ethoxy]methyl]-5-pyrazoleboronic acid (0.343 g) in THF (10 mL) as described in Example 7-2) to give N-[4-[1-[[2-(trimethylsilyl)ethoxy]methyl]-5-pyrazolyl]-2,6-dichlorobenzoyl]-4-(2,6-dimethoxyphenyl)-L-phenylalanine methyl ester (0.277 g). ESMS: m/z 684 (MH$^+$) and 682 (M−H)$^-$.

2) To a solution of the product obtained above (0.277 g) in MeOH (10 mL) was added conc. HCl (0.20 mL) and a second aliquot of conc. HCl (0.20 mL) after 3 h. After stirring overnight at room temperature, the mixture was concentrated. The residue was dissolved in EtOAc, washed with NaHCO$_3$ and brine, dried (Na$_2$SO$_4$), filtered, and concentrated. The residue was purified by preparative TLC (silica gel; eluent: hexane to hexane/EtOAc 1:1) to yield N-[4-(5-pyrazolyl)-2,6-dichlorobenzoyl]-4-(2,6-dimethoxyphenyl)-L-phenylalanine methyl ester (0.148 g). ESMS: m/z 554 (MH$^+$).

3) The product obtained above was hydrolyzed in a similar manner as described in Example 1-5) to give the title compound (0.133 g). ESMS: m/z 540 (MH$^+$) and 652 (M$^-$+TFA). mp. 156° C.

Example 305

N-[3-(3,5-Dimethyl-4-isoxazolyl)-2,6-dichlorobenzoyl]-4-(2,6-dimethoxyphenyl)-L-phenylalanine The title compound was prepared in a similar manner as described in Example 303 starting from N-(3-bromo-2,6-dichlorobenzoyl)-4-(2,6-dimethoxyphenyl)-L-phenylalanine methyl ester. MS m/z: 569 (MH$^+$) mp. 144.8° C.

Example 306

N-[4-(1,3-thiazol-2-yl)-2,6-dichlorobenzoyl]4-(2,6-dimethoxyphenyl)-L-phenylalanine 1) To a solution of N-(4-bromo-2,6-dichlorobenzoyl)-4-(2,6-dimethoxyphenyl)-L-phenylalanine methyl ester (0.240 g) in toluene (10 mL) was added 2-tributylstannio-1,3-thiazole (0.52 g) and Pd(PPh$_3$)$_4$ (0.11 g) and the solution was heated to 80° C. under N$_2$ for 24 h. It was worked up and purified in a similar manner as described in Example 135-3) to yield 30 mg of N-[4-(1,3-thiazol-2-yl)-2,6-dichlorobenzoyl]-4-(2,6-dimethoxyphenyl)-L-phenylalanine methyl ester. ESMS: m/z 571 (MH$^+$).

2) The product obtained above was hydrolyzed in a similar method as described in Example 1-5) to yield the title compound (22.7 mg) ESMS: m/z 557 (MH$^+$). mp. 141.9° C.

Example 307

N-[4-(1,3-Thiazol-4-yl)-2,6-dichlorobenzoyl]-4-(2,6-dimethoxyphenyl)-L-phenylalanine The title compound was prepared in a manner analogous to Example 306 by replacing 2-tributylstannio-1,3-thiazole with 4-tributylstannio-1,3-thiazole. ESMS: m/z 557 (MH$^+$) and 555 (M$^-$−H). mp. 186.5° C.

Example 308

N-[4-(2-Pyrazinyl)-2,6-dichlorobenzoyl]-4-(2,6-dimethoxyphenyl)-L-phenylalanine

The title compound was prepared in a manner analogous to Example 306 by replacing 2-tributylstannio-1,3-thiazole with 2-tributylstanniopyrazine. ESMS: m/z 552 (MH$^-$). mp. 145.7° C.

The following compounds (Examples 309–318) were prepared in a similar method as described in Example 303.

TABLE 23

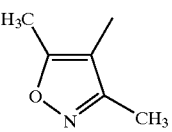

| Example | R$^1$ | m/z (MH$^+$) |
|---|---|---|
| 309 | 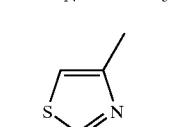 | 569 |
| 310 | 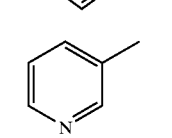 | 558 |
| 311 |  | 551 |

TABLE 23-continued

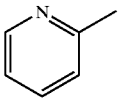

| Example | R¹ | m/z (MH⁺) |
|---|---|---|
| 312 | 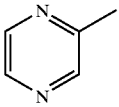 | 551 |
| 313 | 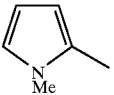 | 552 |
| 314 | 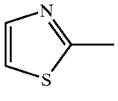 | 553 |
| 315 | 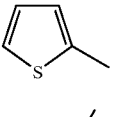 | 557 |
| 316 | 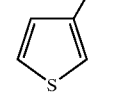 | 556 |
| 317 | 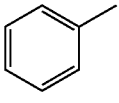 | 557 |
| 318 |  | 550 |

Example 319

N-(2,6-Dichlorobenzoyl)-4-[2,6-dimethoxy-3-(morpholinomethyl)phenyl]-L-phenylalanine 1) 2,6-Dimethoxy-3-(hydroxymethyl)benzeneboronic acid was coupled with N-(2,6-dichlorobenzoyl)-4-bromo-L-phenylalanine ethyl ester in a similar method as described in Example 7-2) to give N-(2,6-dichlorobenzoyl)-4-[2,6-dimethoxy-3-(hydroxymethyl)phenyl]-L-phenylalanine ethyl ester.

2) Thionyl chloride (100 mL) was added to an ice-cold solution of the product obtained above (0.212 mg) in $CH_2Cl_2$ (5 mL) under $N_2$. The mixture was stirred for 1 hour at room temperature and evaporated. The residue was dissolved in $CH_2Cl_2$, evaporated, and dried under vacuum to give N-(2,6-dichlorobenzoyl)-4-[2,6-dimethoxy-3-(chloromethyl)phenyl]-L-phenylalanine ethyl ester as a crude product (0.22 g).

3) A solution of the product obtained above (0.22 g) in DMF (5 mL) was added to an ice-cold solution of morpholine (41 mg) in DMF (1 mL) containing $Et_3N$ (0.111 mL) under $N_2$. The mixture was stirred for 14 hours at room temperature and then partitioned between EtOAc and water. The EtOAc layer was separated and washed successively with satd. $NaHCO_3$, water and brine, dried and evaporated. The residue was purified by column chromatography (silica gel; eluent: EtOAc) to give 0.186 g of N-(2,6-dichlorobenzoyl)-4-[2,6-dimethoxy-3-(morpholinomethyl)phenyl]-L-phenylalanine ethyl ester. ESMS: m/z 601 (MH⁺).

4) The product obtained above was hydrolyzed in a similar method as described in Example 1-5) to give the title compound. ESMS: m/z 573 (MH⁺). mp. 241–242° C.

Example 320

N-(2,6-Dichloro-4-fluorobenzoyl)-4-(2,6-dimethoxyphenyl)-L-phenylalanine

The title compound was prepared in a similar method as described in Example 2. MS m/z 492 (MH⁺), mp.206–207° C.

Example 321

N-(2,6-Dichlorobenzoyl)-4-[2,6-dimethoxy-4-(trifluoromethyl)phenyl]-L-phenylalanine The title compound was prepared in a similar method as described in Example 2.
MS m/z 542 (MH⁺), mp. 231–232° C.

Example 322

N-(2,6-Dichlorobenzoyl)-4-(2,6-dimethoxy-3-bromophenyl)-L-phenylalanine

1) N-(2,6-Dichlorobenzoyl)-4-(2,6-dimethoxyphenyl)-L-phenylalanine methyl ester (1.01 g) was dissolved in $CH_2Cl_2$ (40 mL) under $N_2$ and tetrabutylammonium tribromide (1.21 g) was added and the mixture was stirred at room temperature overnight. More tetrabutylammonium tribromide (0.55 g) was added and the mixture was stirred for 1 day. The mixture was then washed with water (25 mL) and the organic layer was dried ($MgSO_4$), filtered and evaporated. The residue was purified by flash column chromatography (silica gel; eluent: hexane and AcOEt) to give N-(2,6-dichlorobenzoyl)-4-(2,6-dimethoxy-3-bromophenyl)-L-phenylalanine methyl ester (1.17 g).

2) The product obtained above was hydrolyzed in a similar manner as describe in Example 1-5) to give the title compound. MS m/z 555 (MH⁺), mp. 205–206° C.

Example 323

N-(2,6-Dichlorobenzoyl)-4-(2,6-dimethoxy-3-aminophenyl)-L-phenylalanine

1) N-(2,6-Dichlorobenzoyl)-4-(2,6-dimethoxyphenyl)-L-phenylalanine methyl ester (1.59 g) was dissolved in THF (4 mL) under $N_2$ then 70% $HNO_3$ (4 mL) was added and the mixture was stirred at 50° C. overnight. The mixture was diluted with AcOEt (150 mL) and washed with water (100 mL). The organic layer was dried ($MgSO_4$), filtered and evaporated. The residue was dissolved in anhydrous MeOH (100 mL) and dry HCl gas was bubbled through the mixture at 0° C. for a few minutes. The mixture was stirred at room temperature overnight, concentrated, taken up with AcOEt and washed with 1N HCl, satd. NaHCO$_3$ and brine. The organic layer was dried (MgSO$_4$), filtered and evaporated. The crude product was purified by flash column chromatography (silica gel; eluent: hexanes and AcOEt) to give N-(2,6-dichlorobenzoyl)-4-(2,6-dimethoxy-3-nitrophenyl)-L-phenylalanine methyl ester (1.1 g).

2) The product obtained above was dissolved in EtOH (40 mL), and Na$_2$S$_2$O$_4$ (2.6 g) in water (5 mL) was added. The mixture was refluxed for 2 hours and concentrated. The residue was taken up with AcOEt and washed with brine. The organic layer was dried (MgSO$_4$), filtered and evaporated. The residue was purified by preparative TLC (silica gel; eluent: hexanes and AcOEt) to give N-(2,6-dichlorobenzoyl)-4-(2,6-dimethoxy-3-aminophenyl)-L-phenylalanine methyl ester (0.31 g).

3) The product obtained above was hydrolyzed in a similar method as described in Example 1-5) to give the title compound. MS m/z 542 (MH$^+$), mp. 231–232° C.

Example 324

N-(2,6-Dichlorobenzoyl)-4-[2,6-dimethoxy-3-(methylureido)phenyl]-L-phenylalanine The title compound was obtained in a similar procedure as described in Example 70 by reacting N-(2,6-dichlorobenzoyl)-4-(2,6-dimethoxy-3-aminophenyl)-L-phenylalanine methyl ester with MeNCO instead of MeNCS. MS m/z 546 (MH$^+$), mp. 236–237° C.

Example 325

N-(2,6-Dichlorobenzoyl)-4-[2,6-dimethoxy-3-(acetylamino)phenyl]-L-phenylalanine

The title compound was obtained in a similar procedure as describe in Example 67 by reacting N-(2,6-dichlorobenzoyl)-4-(2,6-dimethoxy-3-aminophenyl)-L-phenylalanine methyl ester with acetyl chloride. MS m/z 531 (MH$^+$), mp. 244–245° C.

Example 326

N-(2,6-Dichlorobenzoyl)-4-(2,6-dimethoxy-3-carbamoylphenyl)-L-phenylalanine

1) N-(2,6-Dichlorobenzoyl)-4-(2,6-dimethoxyphenyl)-L-phenylalanine methyl ester (150 mg) was dissolved in MeCN (6 mL) under N$_2$ and chlorosulfonyl isocyanate (45 μL) was added, and the mixture was stirred at room temperature for 2.5 h. The mixture was concentrated and 1N HCl (8 mL) was added. The mixture was stirred at room temperature overnight, extracted with AcOEt, dried (MgSO$_4$), filtered and evaporated. The crude product was purified by preparative TLC (silica gel; eluent: AcOEt) to give N-(2,6-dichlorobenzoyl)-4-(2,6-dimethoxy-3-carbamoylphenyl)-L-phenylalanine methyl ester (156 mg).

2) The product obtained above was hydrolyzed in a similar method as described in Example 1-5) to give the title compound. MS m/z 517 (MH$^+$), mp. 227–228° C.

The following compounds (Examples 327–328) were made from 7-bromo-2,3-dihydrobenzo[b]furan and 8-bromo-3,4-dihydro-2H-benzopyran respectively (Kerrigan, F., Martin, C., Thomas, G. H., Tet. Lett. 1998, 39, 2219–2222), in a similar procedure as described in Example 7.

TABLE 24

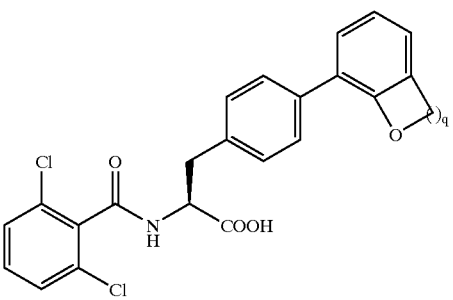

| Example | q | ms MH$^+$ | mp ° C. |
|---|---|---|---|
| 327 | 2 | 456 | 215–216 |
| 328 | 3 | 470 | 214–215 |

Example 329

N-(2,6-Dichlorobenzoyl)-4-(1-tert-butoxycarbonyl-2-pyrrolyl)-L-phenylalanine

The title compound was prepared in a similar method as described in Example 7 using 1-(t-butoxycarbonyl)pyrrole-2-boronic acid (Frontier Scientific). MS m/z 503 (MH$^+$), mp. 98–99° C.

Example 330

N-(2,6-Dichlorobenzoyl)-4-(3,5-dimethyl-4-isoxazolyl)-L-phenylalanine

The title compound and methyl ester were prepared in a similar method as described in Example 7. MS m/z 433 (MH$^+$), mp. 119° C.

Methyl ester of the title compound: MS m/z 447 (MH$^+$), mp. 152° C.

Example 331

N-(2,6-Dichloro-3-bromobenzoyl)-4-(2,6-dimethoxyphenyl)-L-phenylalanine

The title compound was prepared in a similar method as described in Example 322. MS m/z 553 (MH$^+$), mp. 234.8° C.

The following compounds (Examples 332–335) were prepared in a similar method as described in Example 2.

TABLE 25

![Structure: 2,6-dichloro-4-R¹-benzoyl amide of 4-(2-methoxyphenyl)phenylalanine]

| Example | R¹ | MS, m/z | mp., °C |
|---|---|---|---|
| 332 | CH₃NH— | 439 (MH⁺) | 82.8 |
| 333 | CH₃SO₂N(CH₃)— | 517 (MH⁺) | 79.3 |
| 334 | (CH₃)₂SO₂NH— | 532 (MH⁺) | 128.1 |

Example 335

N-[2-Chloro-4-(methansulfonylamino)benzoyl]-4-[2-(trifluoromethyl)phenyl]-L-phenylalanine The title compound was prepared in a similar manner as described in Example 3. MS: m/z 541 (MH⁺), mp. 114° C.

Example 336

N-(2,6-Dichlorobenzoyl)-3-chloro-4-(2-methoxyphenyl)-L-phenylalanine

The title compound was prepared in a similar method as described in Example 1 using N-(tert-butoxycarbonyl)-3-chloro-L-tyrosine methyl ester. ESMS m/z 479 (MH⁺), mp. 131° C.

The following compounds (Examples 337–339) were prepared in a similar method as described in Example 71.

TABLE 26

![Structure with R⁵ substituent]

| Example | R⁵ | MS m/z (MH⁺) | mp., °C |
|---|---|---|---|
| 337 | —COCH₂CH₃ | 500 | 118–119 |
| 338 | —CO(CH₂)₃CH₃ | 528 | 117.6 |
| 339 | —CO(CH₂)₅CH₃ | 556 | 86–88 |

The following compounds (Examples 340–342) were prepared a similar method as described in Example 73.

TABLE 27

![Structure with R⁵ and R⁶ substituents]

| Example | R⁵ | R⁶ | MS m/z (MH⁺) | mp., °C |
|---|---|---|---|---|
| 340 | —CH(OH)CH₃ | 3,4,5-trimethoxyphenyl (MeO, MeO, OMe) | 548 | 121–123 |
| 341 | —CH(OH)CH₂CH₃ | 3-methoxyphenyl (MeO) | 502 | 117–119 |

TABLE 27-continued

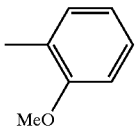

| Example | R⁵ | R⁶ | MS m/z (MH⁺) | mp., °C. |
|---|---|---|---|---|
| 342 | —CH(OH)(CH₂)₃CH₃ | (2-methoxyphenyl, o-tolyl with OMe) | 528 (M − H)⁻ | 158–159 |

Example 343

N-(2,6-Dichlorobenzoyl)-3-acetylamino-4phenyl-L-phenylalanine

The title compound was prepared in a similar procedure as described in Example 80. ESMS m/z 471 (MH⁺).

The following compounds (Examples 344–345) were prepared in a similar procedure as described in Example 64 using ethyl chloroformate.

TABLE 28

| Example | R⁶ | MS m/z (MH⁺) |
|---|---|---|
| 344 | phenyl | 501 |
| 345 | 2-methoxyphenyl (MeO) | 531 |

Example 346

N-(2,6-Dichlorobenzoyl)-4-(2,6-dimethoxy-4-hydroxyphenyl)-L-phenylalanine

1) A mixture of 2,6-dimethoxy-4-(tert-butyl-diphenylsilyloxy)benzeneboronic acid (3 g), N-(2,6-dichlorobenzoyl)-4-bromo-L-phenylalanine ethyl ester (0.8 g), Pd(PPh₃)₄ (1 g) and K₂CO₃ (2.1 g) in DME/H₂O (20 mL/0.5 mL) was heated at 80° C. for 6 hour under N₂. The mixture was diluted with EtOAc and washed with water, dried and evaporated. The residue was dissolved in EtOAc and the solution was filtered through a silica gel column and evaporated. The residue was dissolved in THF, and TBAF (1.6 M in THF, 4 ml) was added. The mixture was stirred at room temperature for 1 hour, diluted with water and extracted with EtOAc. The extract was washed with water, dried and evaporated. The residue was purified by flash column chromatography (silica gel; eluent: EtOAc/hexane 1/2) to yield 0.5 g of N-(2,6-dichlorobenzoyl)-4-(2,6-dimethoxy-4-hydroxyphenyl)-L-phenylalanine ethyl ester. ESMS m/z: 490 (MH⁺).

2) The product obtained above (0.05 g) was hydrolyzed with LiOH in a similar method as described in Example 1-5) to give 0.04 g of the title compound. ESMS m/z: 490 (MH⁺).

The following compounds (Examples 347–350) were prepared in a similar procedure as described in Example 32.

TABLE 29

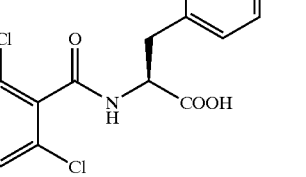

| Example | Rᵇ | MS m/z (MH⁺) |
|---|---|---|
| 347 | (3-methyl-4-allyloxy-2,6-dimethoxyphenyl) | 530 |

TABLE 29-continued

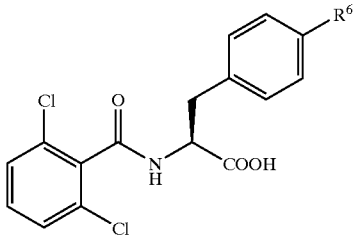

| Example | R<sup>b</sup> | MS m/z (MH<sup>+</sup>) |
|---|---|---|
| 348 | 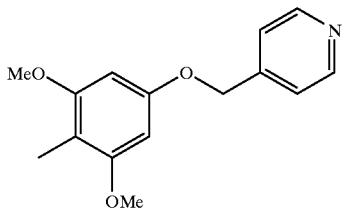 | 581 |
| 349 | 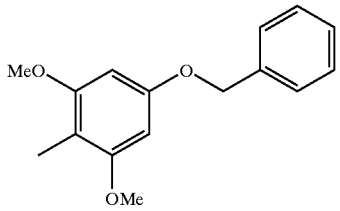 | 581 |
| 350 | | 580 |

Example 351

N-(2,6-Dichlorobenzoyl)-3-[1-(hydroxyimino)ethyl]-4-(2-methoxyphenyl)-L-phenylalanine 1) To a solution of N-(2,6-dichlorobenzoyl)-3-acetyl-4-(2-methoxyphenyl)-L-phenylalanine ethyl ester (0.15 g) in n-BuOH (5 mL) were added $NH_2OH$ HCl salt (23 mg) and NaOAc (40 mg). The mixture was refluxed for 6 hour, then evaporated. The residue was diluted with $CH_2Cl_2$, washed with 1N HCl, dried and evaporated. The residue was purified by preparative TLC (silica gel; eluent: EtOAc/hexane 1:1) to give N-(2,6-dichlorobenzoyl)-3-[1-(hydroxyimino)ethyl]-4-(2-methoxyphenyl)-L-phenylalanine ethyl ester. ESMS: m/z 490 (MH<sup>+</sup>).

2) The product obtained above was hydrolyzed with LiOH in a similar manner as described in Example 1-5) to give the title compound. ESMS: m/z 501 (MH<sup>+</sup>).

Example 352

N-(2,6-Dichlorobenzoyl)-3-[1-(methoxyimino)ethyl]-4-(2-methoxyphenyl)-L-phenylalanine 1) To a solution of N-(2,6-dichlorobenzoyl)-3-acetyl-4-(2-methoxyphenyl)-L-phenylalanine ethyl ester (0.12 g) in EtOH (5 mL) were added $NH_2OMe$ HCl salt (24 mg) and DIEA (60 mg). The mixture was refluxed for 2 h and evaporated. The residue was diluted with EtOAc, washed with 1N HCl, dried, and evaporated. The residue was purified by preparative TLC (silica gel; eluent: EtOAc/hexane 2:1) to give 0.058 g of N-(2,6-dichlorobenzoyl)-3-[1-(methoxyimino)ethyl]-4-(2-methoxyphenyl)-L-phenylalanine ethyl ester. ESMS: m/z 534 (M−H)<sup>−</sup>.

2) The product obtained above was hydrolyzed with LiOH in a similar manner as described in Example 1-5) to give 0.04 g of the title compound. ESMS: m/z 513 (M−H)<sup>−</sup>, mp. 106.8° C.

The following compounds (Examples 353–356) were prepared in a similar method as described in one of above Examples:

TABLE 30

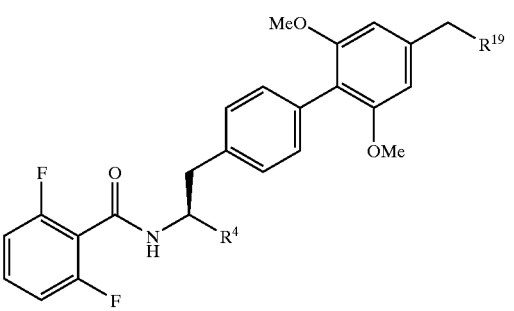

| Example | R<sup>4</sup> | R<sup>19</sup> | ESMS m/z (MH<sup>+</sup>) | mp. ° C. |
|---|---|---|---|---|
| 353 | COOH | 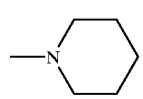 | 538 | 232 |

TABLE 30-continued

[Structure: 2,6-difluorobenzoyl amide of phenylalanine derivative with 4-aryl substituent bearing MeO, OMe, and CH₂-R¹⁹ groups; α-carbon bears R⁴]

| Example | R⁴ | R¹⁹ | ESMS m/z (MH⁺) | mp. °C. |
|---|---|---|---|---|
| 354 | COOEt | —N(piperidinyl) · HCl | 567 | 150 |
| 355 | COOH | —N(piperazinyl)NMe | 553 | 225 |
| 356 | COOEt | —N(piperazinyl)NMe · 2 HCl | 582 | 226 |

Example 357
N-(2,6-Dichlorobenzoyl-4-[2,6-dimethoxy-4-(succinimidomethyl)phenyl]-L-phenylalanine 1) DEAD (0.13 mL) was added to an ice-cooled solution of N-(2,6-dichlorobenzoyl)-4-[2,6-dimethoxy-4-(hydroxymethyl)phenyl]-L-phenylalanine tert-butyl ester (250 mg), triphenylphosphine (175 mg) and succinimide (90 mg) in THF (3 mL) under $N_2$. The mixture was stirred at 0° C. for 30 min, and warmed to room temperature and stirred for 2 h. The mixture was partitioned between $H_2O$ and EtOAc, and the aqueous layer was extracted with EtOAC. The combined organic layer was dried (MgSO₄), and concentrated in vacuo. The residue was purified by preparative TLC (silica gel; eluent: EtOAc/hexane 1:1) to give N-(2,6-dichlorobenzoyl)4-[2,6-dimethoxy-4-(succinimidomethyl)phenyl]-L-phenylalanine tert-butyl ester (138 mg).

2) TFA (2 mL) was added to a solution of the product obtained above (120 mg) in $CH_2Cl_2$ (4 mL). The mixture was stirred at room temperature for 3 days, and the mixture was concentrated in vacuo. The residue was purified by column chromatography (silica gel; eluent: $CH_2Cl_2$/MeOH 95:5) and recrystallization from EtOH/$H_2O$ to give the title compound (61 mg). mp. 137° C. ESMS: m/z 608 [M+Na]⁺.

Example 358
N-(2,6-Dichlorobenzoyl)-4-(2,6-dimethoxy-4-[(3-methyl-2,5-dioxo-1-imidazolidinyl)methyl]phenyl]-L-phenylalanine The title compound was prepared in a similar procedure as described in Example 357, but replacing succinimide with 1-methylhydantoin. mp. 248° C., ESMS: m/z 624 [M+Na]⁺.

Example 359
N-(2,6-Dichlorobenzoyl)-4-(6-methoxy-2-hydroxyphenyl)-L-phenylalanine N-(2,6-Dichlorobenzoyl)-4-(6-methoxy-2-hydroxyphenyl)-L-phenylalanine ethyl ester was hydrolyzed with LiOH in a similar method as described in Example 1-5) to give the title compound. mp. 224.4° C., ESMS: m/z 460 (MH⁺), 458 (M–H)⁻.

Example 360
N-(2,6-Dichlorobenzoyl)-4-(2,6-dihyroxyphenyl)-L-phenylalanine 1) 2,6-Di(methoxymethoxy)benzeneboronic acid (0.25 g) was coupled with N-(2,6-dichlorobenzoyl)-O-(trifluoromethanesulfonyl)-L-tyrosine ethyl ester in a similar procedure as described in Example 5-3) to afford N-(2,6-dichlorobenzoyl)-4-[2,6-di(methoxymethoxy)phenyl]-L-phenylalanine ethyl ester. ESMS: m/z 562 (MH⁺).

2) To a solution of the product obtained above (0.076 g) in EtOH (5 mL) was added HCl (4N in dioxane, 1.2 mL) and the mixture was stirred under $N_2$ for 4 hours at room temperature. The mixture was evaporated to give N-(2,6-dichlorobenzoyl)-4-(2,6-dihyroxyphenyl)-L-phenylalanine ethyl ester (61.6 mg). ESMS: m/z 474 (MH⁺).

3) The product obtained above (61.6 mg) was hydrolyzed with LiOH (33.8 mg) in a similar manner as described in Example 1-5) to give N-(2,6-dichlorobenzoyl)-4-(2,6-dihydroxyphenyl)-L-phenylalanine (58.3 mg). ESMS: m/z 446 (MH⁺), 444 (M–H)⁻, mp. 238° C.

Reference Examples

Reference Example 1
2,6-Dichlorobenzeneboronic acid

1-Bromo-2,6-dichlorobenzene (2.00 g) was dissolved in freshly distilled THF (7 mL). This solution was cooled to −78° C. and n-BuLi (8.3 mL of a 1.6M solution in hexane) was added dropwise to the cold solution under $N_2$. The mixture was stirred for 5 min at −78° C. and (MeO)₃B (2.2 mL) was added. The resulting mixture was allowed to warm to room temperature and stirred overnight. Water was added and the resulting mixture was stirred for 0.5 h, then acidified with HOAc and extracted with EtOAc. The organic layer was further washed with water and brine, dried (MgSO₄) filtered and evaporated to yield 2,6-dichlorobenzeneboronic acid (1.6 g)

Reference Example 2

2,6-Dicyanobenzeneboronic acid 1,3-Dicyanobenzene (1.00 g) was dissolved in freshly distilled THF (70 mL). This solution was cooled to −96° C. and LDA (4.2 mL of a 2M solution) was added dropwise to the cold solution under N₂. The mixture was stirred for 30 min at −96° C. and (MeO)₃B (1.3 mL) was added. The resulting mixture was allowed to warm to room temperature and stirred overnight. Water was added and the resulting mixture was stirred for 0.5 h, then acidified with HOAc and extracted with EtOAc. The organic layer was further washed with water and brine, dried (MgSO₄), filtered and evaporated. The residue was taken up in CH₂Cl₂, filtered and evaporated to yield 2,6-dicyanobenzeneboronic acid(0.56 g).

Reference Example 3

2,6-Dimethoxy-4-propylbenzeneboronic acid

1) Ethyltriphenylphosphonium bromide (4.69 g) was dissolved in anhydrous THF (70 mL) and the mixture cooled to 0–5° C. n-BuLi (5.05 mL of 2.5 M in hexane) was added dropwise and the resulting mixture was stirred at room temperature for 3 h. The mixture was cooled to −78° C. and a solution of 3,5-dimethoxybenzaldehyde (2 g) in anhydrous THF (14 mL) was added. The mixture was allowed to warm up to room temperature then stirred overnight. The mixture was concentrated, and the residue was taken up with AcOEt, washed with water and brine, dried (MgSO₄), filtered and evaporated. The residue was purified by column chromatography (silica gel; eluent: hexane and AcOEt 10:1) to give 3,5-dimethoxy-1-(1-propenyl)benzene as a mixture of cis and trans isomers (2.15 g).

2) The product obtained above was dissolved in EtOH (60 mL) and 10% Pd/C (215 mg) was added. The mixture was stirred under H₂ atmosphere for 19 h. The mixture was passed through a silica pad using CH₂Cl₂ as solvent, and evaporated to give 3,5-dimethoxy-1-propylbenzene (1.76 g).

3) The product obtained above was converted to the title compound by following the procedure similar to Example 7-(1) but replacing 1,3-dimethoxy benzene with 3,5-dimethoxy-1-propylbenzene.

Reference Example 4

2,6-Dimethoxy-4-trifluoromethylbenzeneboronic acid 1) 3-Methoxy-5-(trifluoromethyl)aniline (5 g) was suspended in 20% HCl (200 mL), stirred for 30 min, cooled to 0–5° C. and diazotized with NaNO₂ (2.17 g) added in small portions. The mixture was stirred for 30 min at that temperature and added dropwise to boiling water (200 mL). The mixture was refluxed for 15 min, allowed to cool to room temperature and extracted with AcOEt, dried (MgSO₄), filtered and evaporated. The residue was then purified by column chromatography (silica gel; eluent: hexane and AcOEt) to give 3-methoxy-5-(trifluoromethyl)phenol (3.6 g)

2) The product obtained above was dissolved in acetone (20 mL). K₂CO₃ (5.18 g) and MeI (1.75 mL) were added. The mixture was stirred under N₂ at room temperature for 2 days, evaporated, taken up with water (50 mL), extracted with CH₂Cl₂, dried (MgSO₄), filtered and evaporated. The residue was purified by column chromatography (silica gel; eluent: hexane/AcOEt 10:1 to 1:1) to give the desired 3,5-dimethoxy-α,α,α-trifluorotoluene (2.97 g).

3) The product obtained above was converted to the title compound by following the procedure similar to Example 7-(1) but replacing 1,3-dimethoxybenzene by 3,5-dimethoxy-α,α,α-trifluorotoluene.

Reference Example 5

4-(1,3-Dioxolan-2-yl)-2,6-dimethoxybenzeneboronic acid 1) 4-bromo-3,5-dimethoxybenzaldehyde (3 g) was dissolved in toluene (50 mL) and ethylene glycol (6.8 mL) and a catalytic amount of p-TSA were added. The mixture was refluxed overnight using a Dean Stark apparatus and evaporated. The residue was purified by column chromatography (silica gel; eluent hexane/AcOEt 5:1 to 2:1) to give 4-bromo-3,5-dimethoxybenzaldehyde ethylene acetal (2.63 g).

2) The product obtained above was treated in a similar procedure as described in Example 7-1) to give the title compound.

Reference Example 6

2,6-Dimethoxy-3-methoxymethoxybenzeneboronic acid

1) To anhydrous K₂CO₃ (3.55 g) in acetone (10 mL) under N₂ was added 2,4-dimethoxyphenol (3.3 g, J.O.C. 1984, 49, 4740) in acetone (20 mL). Chloromethyl methyl ether (1.79 mL) was added dropwise and the mixture was stirred at room temperature for 18 h then heated to 50° C. for 24 h. Additional quantity of chloromethyl methyl ether (1.79 mL) was added and the mixture was stirred for another day at 50° C. and evaporated. The residue was taken up with water and extracted with AcOEt. The extract was dried (MgSO₄), filtered and evaporated. The residue was purified by column chromatography (silica gel; eluent: hexane/AcOEt 20:1 to 10:1) to give 1,3-dimethoxy-4-methoxymethoxybenzene (1.18 g).

2) The product obtained above was treated in a similar procedure as described in Example 7-1) replacing 1,3-dimethoxy benzene by 1,3-dimethoxy-4-methoxymethyloxybenzene to give the title compound.

Reference Example 7

6-Methoxy-1,4-benzodioxan-5-ylboronic acid 1) 1,4-Benzodioxan-6-carboxaldehyde (5.20 g) was dissolved in MeOH (60 mL) containing conc. H₂SO₄ (0.6 mL). At 0° C. an aqueous solution of 30% H₂O₂ (4.7 mL) was added to the mixture over 5 minutes. The mixture was warmed to room temperature, stirred an additional 18 h and evaporated. The residue was taken up with H₂O and extracted with CH₂Cl₂. The extract was dried (Na₂SO₄), filtered and evaporated. The residue was purified by column chromatography (silica gel; eluent: hexane to hexane/EtOAc 3:1) to give 6-hydroxy-1,4-benzodioxan (3.85 g). ESMS: m/z 153 MH⁺.

2) To the mixture of the product obtained above (3.83 g), K₂CO₃ (7.0 g) and n-Bu₄NI (186 mg) in DMF (10 mL) was added iodomethane (2.3 mL) and the mixture was stirred at room temperature under $N_2$ for 24 h, filtered and washed with EtOAc (3×15 mL). The filtrate was washed with brine, dried over $Na_2SO_4$, and concentrated. The residue was purified by column chromatography (silica gel; eluent hexane to hexane/EtOAc 4:1) to give 6-methoxy-1,4-benzodioxan (3.25 g). ESMS: m/z 167 ($MH^+$).

3) The product obtained above was converted to the title compound by a similar method as described in Example 7-(1).

Reference Example 8

6-Methoxy-2-methoxymethoxybenzeneboronic acid

The title compound was prepared from 3-methoxyphenol by a similar method as described in Reference Example 6.

Reference Example 9

2,6-Dimethoxy-4-[(t-butyldiphenylsilyloxy)methyl]benzeneboronic acid

1) A mixture of 3,5-dimethoxybenzyl alcohol (4.0 g), t-butyl-diphenylsilyl chloride (6.54 g) and imidazole (3.28 g) in DMF (60 mL) was stirred at room temperature for 24 h. DMF was evaporated and the residue was purified by column chromatography (silica gel; eluent: hexane to hexane/EtOAc 20%) to yield 8.5 g of 3,5-dimethoxy-1-[(t-butyldiphenylsilyloxy)methyl]benzene. ESMS: m/z 407 ($MH^+$).

2) The product obtained above was treated in a similar procedure as described in Example 7-1) to give the title compound. ESMS: m/z 451 ($MH^+$).

Reference Example 10

2,6-Dimethoxy-4-(thiomorpholinomethyl)benzeneboronic acid

1) Thiomorpholine (3.4 g) was added to a solution of 3,5-dimethoxybenzyl chloride (2 g) in THF (25 mL) and the mixture was stirred overnight at room temperature. The solid material was removed by filtration and the filtrate was evaporated. The residue was purified by column chromatography (silica gel; eluent: EtOAc/hexane 1/2) to yield 2 g of 3,5-dimethoxy-1-(thiomorpholino-methyl)benzene. ESMS: m/z 253 (M).

2) The product obtained above was treated in a similar procedure as described in Example 7-1) to give the title compound.

Reference Example 11

2,6-Dimethoxy-4-[(4-tert-butoxycarbonylpiperazinyl)methyl]benzeneboronic acid

The title compound was prepared in a similar procedure as described in Reference Example 10 but replacing thiomorpholine with N-(tert-butoxycarbonyl)piperazine.

The following compounds (Reference Example 12–17) were prepared in a similar method as described in Reference Example 10 by replacing thiomorpholine with the requisite amines.

Reference Example 12

2,6-Dimethoxy-4-(diethylamino)methyl]benzeneboronic acid

Reference Example 13

2,6-Dimethoxy-4-(piperidinomethyl)benzeneboronic acid

Reference Example 14

2,6-Dimethoxy-4-(morpholinomethyl)benzeneboronic acid

Reference Example 15

2,6-Dimethoxy-4-[(4-benzyl-1-piperazinyl)methyl]benzeneboronic acid

Reference Example 16

2,6-Dimethoxy-4-[(dimethylamino)methyl]benzeneboronic acid

Reference Example 17

2,6-Dimethoxy-4-[(4-tert-butoxycarbonylpiperazinyl)methyl]benzeneboronic acid

Reference Example 18

2,6-Dimethoxy-4-(2-hydroxyethyl)benzene boronic acid

1) A solution of (3,5-dimethoxy)phenylacetic acid (3 g) in $Et_2O$ (100 mL) was cooled to 0° C. and $LiAlH_4$ (1M in $Et_2O$, 16.8 mL) was added. The mixture was warmed to room temperature and stirred for 5 h, whereupon the pH was adjusted to 5 using HCl (1 M). The mixture was washed with $H_2O$/EtOAc and the organic layer was separated. The aqueous layer was extracted with EtOAc. The combined organic layers were dried ($MgSO_4$) and concentrated in vacuo to give 3,5-dimethoxy-4-(2-hydroxyethyl)benzene (2.8 g) as a crude product.

2) The product was treated in a similar procedure as described in Example 7-1) to give the title compound.

Reference Example 19

2,6-Dimethoxy-4-(tert-butyl-diphenylsilyloxy)benzeneboronic acid

1) A mixture of 3,5-dimethoxybenzyl alcohol (4.0 g), tert-butyl-diphenylsilyl chloride (6.54 g) and imidazole (3.28 g) in DMF (60 mL) was stirred at room temperature for 24 h. DMF was evaporated and the residue was purified by column chromatography (silica gel; eluent: hexane to hexane/EtOAc 20%) to yield 8.5 g of 3,5-dimethoxybenzyl tert-butyldiphenylsilyl ether. ESMS: m/z 407 ($MH^+$).

2) The product obtained above was treated in a similar procedure as described in Example 7 to give the title compound. ESMS: m/z 451 ($MH^+$).

Reference Example 20

2,6-Dimethoxy-4-hydroxymethylbenzeneboronic acid 3,5-Dimethoxybenzyl alcohol was treated in a similar procedure as described in Example 7 to yield the title compound.

Reference Example 21

2,6-Dimethoxy-3-hydroxymethylbenzeneboronic acid

The title compound was prepared in a similar method as described in Example 7 from 2,4-dimethoxybenzylalcohol.

Reference Example 22

1-Bromo-2,4-dimethoxy-6-cyanobenzene

To a solution of 3,5-dimethoxybenzonitrile (2 g) in $CH_2Cl_2$ (100 mL) was added pyridinium tribromide (4 g). The mixture was stirred for 24 h at room temperature then washed successively with aqueous $NaHCO_3$, water and brine, dried ($MgSO_4$) filtered and evaporated. The residue was crystallized from $CH_2Cl_2$ and hexane to yield the title compound (1.8 g).

Reference Example 23

N-Allyl-N-tert-butoxycarbonyl-4-bromo-3,5-dimethoxyaniline

1) 3,5-Dimethoxyaniline (7.55 g) was dissolved in $CH_2Cl_2$ (100 mL) under $N_2$ and the solution was cooled to −78° C. A solution of tetrabutylammonium tribromide (25 g) in $CH_2Cl_2$ (100 mL) was added and the mixture was stirred at that temperature for 45 min. The mixture was allowed to warm up to room temperature, stirred for 1.5 h and extracted with 1N HCl. The extract was neutralized with 3 N NaOH and extracted with AcOEt. The extract was dried ($MgSO_4$), filtered and evaporated. The residue was purified by column chromatography (silica gel; eluent: hexane/AcOEt 4:1 to 2:3) to give 4-bromo-3,5-dimethoxyaniline (3.76 g).

2) The product obtained above (3 g) was then dissolved in anhydrous THF (25 mL) under $N_2$ and DIEA (5.4 mL) was added. A solution of di-tert-butyl dicarbonate (3.39 g) in anhydrous THF (20 mL) was added and the mixture was stirred at 45° C. for 3.5 days. The solvent was evaporated and the residue was taken up with AcOEt, washed successively with 1N HCl, sat. $NaHCO_3$ and brine. The organic layer was dried ($MgSO_4$), filtered and evaporated. The residue was purified by column chromatography (silica gel; eluent hexane/AcOEt 4:1) to give a solid. The solid was triturated with hexane to remove remaining di-tert-butyl dicarbonate and N-tert-butoxycarbonyl-4-bromo-3,5-dimethoxyaniline was isolated by filtration (3.67 g).

3) NaH (60%, 0.585 g) was added to a solution of the product obtained above in anhydrous THF/DMF (100/6 mL) and the mixture was stirred for a few minutes. Allyl bromide (1.13 mL) was added and the mixture was stirred at room temperature overnight, concentrated and the residue was purified by column chromatography (silica gel; eluent: hexane/AcOEt 4:1) to give the title compound (3.96 g).

Synthesis of Benzoic Acids

Reference Example 24

4-Amino-2,6-dichlorobenzoic acid methyl ester

1) To 2,6-dichloro-4-nitrobenzoic acid (12.8 g, U.S. Pat. No. 3,423,475) was added anhydrous $CH_2Cl_2$ (60 mL) and thionyl chloride (40 mL) then the resulting mixture was refluxed for 19 h. The mixture was allowed to cool to room temperature and evaporated. Additional $CH_2Cl_2$ (10 mL) was added and the solution was evaporated. MeOH (100 mL) was added to the residue and the mixture was refluxed for 17 h. The mixture was allowed to cool to room temperature and placed in an ice-bath. The precipitated solid was collected by filtration to give methyl 2,6-dichloro-4-nitrobenzoate (10.8 g, 80%).

2) To a mixture of the product obtained above in EtOH (250 mL) was added a solution of $Na_2S_2O_4$ (45 g) in water (100 mL). The mixture was refluxed for 2 h, stirred at room temperature overnight, filtered and concentrated. The residue was dissolved in 1N HCl (250 mL), stirred for 2 h, neutralized with 10% NaOH and extracted with AcOEt. The extract was dried ($MgSO_4$), filtered and evaporated. The residue was recrystallized from AcOEt/hexane to give the title compound (7.48 g).

Reference Example 25

4-Bromo-2,6-dichlorobenzoic acid and 4-bromo-2,6-dichloro benzoyl chloride

1) 4-Amino-2,6-dichlorobenzoic acid methyl ester (1.00 g) was suspended in 40% aq. HBr and the mixture was cooled 1 to 0–5° C. After $NaNO_2$ (376 mg) was added in small portions, the mixture was stirred for about 5 min. Copper (100 mg) was added and the mixture was warmed up to 100° C. The mixture was then stirred at 100° C. for 30 min, diluted with water and extracted with AcOEt. The extract was dried ($MgSO_4$), filtered and evaporated. The residue was purified by column chromatography (silica gel; eluent: hexane and AcOEt 50:1) to give 4-bromo-2,6-dichlorobenzoic acid methyl ester (1.07 g).

2) The product obtained above (1.06 g) was dissolved in THF/MeOH (50 mL, 6:1) and LiOH (1M, 7.47 mL) was added. The mixture was refluxed for 1 day, evaporated, and the residue was taken up with water (50 mL) and acidified to pH <2 with 1N HCl. The mixture was extracted with AcOEt, dried ($MgSO_4$), filtered and evaporated to give 4-bromo-2,6-dichlorobenzoic acid (0.94 g).

3) To a solution of the product obtained above in $CH_2Cl_2$ (20 mL), was added thionyl chloride (2.51 mL). The mixture refluxed for 5 h, evaporated, and coevaporated with $CH_2Cl_2$ to give 4-bromo-2,6-dichlorobenzoyl chloride.

Reference Example 26

2,6-Dichloro-4-hydroxybenzoic acid

1) 4-Amino-2,6-dichlorobenzoic acid methyl ester (0.5 g) was suspended in 20% HCl (25 mL) and stirred for 30 min then cooled to 0–5° C. After slow addition of $NaNO_2$ (188 mg), the mixture was stirred for 30 min at that temperature and added to boiling water (50 mL). The mixture was then refluxed for 2 h, allowed to cool to room temperature and extracted with AcOEt, dried ($MgSO_4$), filtered and evaporated. The residue was purified by preparative TLC (silica gel; eluent: $CH_2Cl_2$) to give 2,6-dichloro-4-hydroxybenzoic acid methyl ester (275 mg).

2) To a solution of the product obtained above (265 mg) in THF/MeOH (25 mL, 6:1) was added 1N NaOH (3.6 mL), and the mixture was refluxed for 1 day. 1N NaOH (3.6 mL) was added and the mixture was refluxed for another day. The mixture was evaporated and the residue was taken up with water, acidified to pH <2 with 1 N HCl and extracted with AcOEt containing a little amount of MeOH. The extract was dried ($MgSO_4$), filtered and evaporated to give the title compound (248 mg).

Reference Example 27

2,6-Dichloro-4-fluorobenzoic acid

4-Amino-2,6-dichlorobenzoic acid methyl ester (0.5 g) was suspended in 15% HCl (10 mL) and stirred for 30 min then cooled to 0–5° C. After addition of NaNO$_2$ (188 mg) in small portions, the mixture was stirred for 30 min at that temperature. Precooled HBF$_4$ (0.46 mL) was added and the mixture was stirred for 30 min. The resulting precipitate was collected and washed successively with cold water, MeOH and ether. The solid was then dried over conc. H$_2$SO$_4$ in a vacuum dessicator for a few days. The solid was heated with a bunsen burner until all the solid has melted. The resulting fumes were collected over water (distilling apparatus). The product was then recovered with Et$_2$O. The solvent was evaporated and the crude product was purified by preparative TLC (silica gel; eluent: hexane/AcOEt 50:1 to 20:1) to give 2,6-dichloro-4-fluorobenzoic acid methyl ester (241 mg).

2) To a solution of the product obtained above (233 mg) in CCl$_4$ was added TMSI (164 mL). The mixture was then stirred under N$_2$ at 50° C. for 2 days. Water was added and the mixture was stirred for 1 h. 1N HCl (25 mL) was added and the mixture was extracted with AcOEt. The extract was dried (MgSO$_4$), filtered and evaporated. The residue was purified by column chromatography (silica gel; eluent: CHCl$_3$/MeOH gradient) to give the title compound (38 mg).

Reference Example 28

2-Chloro-4-(2-thiazolinylamino)benzoic acid

1) A mixture of 4-amino-2-chlorobenzoic acid methyl ester (0.5 g) and 2-chloroethylisothiocyanate (0.26 mL) in THF (20 mL) was refluxed for 24 h. THF was distilled and the residue was purified by column chromatography (silica gel: eluent: hexane/EtOAc 3:1-1:1) to yield 2-chloro-4-(2-thiazolinylamino)benzoic acid methyl ester (74 mg). ESMS: m/z 271 (MH$^+$).

2) The product obtained above was hydrolyzed with LiOH to give the title compound (43 mg). ESMS: m/z 257 (MH$^+$).

Reference Example 29

2-Chloro-4-(2-oxazolinylamino)benzoic acid

1) A mixture of 4-amino-2-chlorobenzoic acid methyl ester (0.5 g) and 2-chloroethylisocyanate (0.23 mL) in THF (20 mL) was heated under reflux for 24 h. THF was distilled and the residue was purified by column chromatography (silica gel; eluent: hexane/EtOAc 3:1-1:1) to yield 4-[3-(2-chloethyl)ureido]-2-chlorobenzoic acid methyl ester (0.63 mg). ESMS: m/z 291 (MH$^+$).

2) NaOMe (0.21 g) was added to a solution of the product obtained above (0.58 g) in THF (20 mL) and the mixture was refluxed overnight. THF was distilled, and the residue was extracted with EtOAc. The extract was washed with water, dried (MgSO$_4$) and evaporated. The residue was purified by column chromatography (silica gel; eluent: EtOAc) to yield 2-chloro-4-(2-oxazolidinylamino)benzoic acid methyl ester (0.46 g). ESMS: m/z 254 (MH$^+$).

3) The product obtained above was hydrolyzed with LiOH to give the title compound. ESMS: m/z 240 (MH$^+$).

Reference Example 30

2-Chloro-4-(2-oxo-1-pyrrolidinyl)benzoic acid

1) To a solution of 4-amino-2-chlorobenzoic acid methyl ester hydrochloride (0.52 g) and DIEA (0.27 mL) in CH$_2$Cl$_2$ (20 mL) at 0° C. under N$_2$ was added 4-chlorobutyryl chloride (0.3 mL) and the mixture was stirred for 4 h at that temperature. DMAP (0.23 mmol) was added and the mixture was stirred at room temperature overnight. 4-Chlorobutyryl chloride (0.3 mL) and DIEA (0.09 mL) were added and the mixture was stirred for 24 h. The mixture was diluted with CH$_2$Cl$_2$ (100 mL) and the solution was washed successively with 1N HCl, std. NaHCO$_3$, brine, dried and evaporated. The residue was purified by column chromatography (silica gel; eluent: hexane/EtOAc 3:1) to yield 4-(4-chlorobutyryl) amino-2-chlorobenzoic acid methyl ester (0.64 g). ESMS: m/z 290 (MH$^+$).

2) NaOMe (0.33 g) was added to a solution of the product obtained above (0.64 g) in THF (20 mL) and the mixture was refluxed for 3 h. THF was removed and the residue was partitioned between EtOAc and water. EtOAc layer was separated and the aqueous layer was extracted with EtOAc. The combined extract was dried (MgSO$_4$) and evaporated. The residue was purified by column chromatography (silica gel; eluent: hexane/EtOAc 1:1) to yield 2-chloro-4-(2-oxo-1-pyrrolidinyl)benzoic acid methyl ester. ESMS: m/z 254 (MH$^+$).

3) The product obtained above was hydrolyzed with LiOH to give the title compound. ESMS: m/z 240 (MH$^+$).

Reference Example 31

2-Chloro-4-(1-pyrrolyl)benzoic acid

1) A mixture of 4-amino-2-chlorobenzoic acid methyl ester (0.46 g) and 2,5-dimethoxytetrahydrofuran (0.33 mL) in AcOH (16 mL) was heated under reflux for 2 h. The mixture was cooled to room temperature, diluted with water and extracted with EtOAc. The extract was washed with satd. NaHCO$_3$ and brine, dried (MgSO$_4$), filtered and evaporated. The residue was purified by column chromatography (silica gel; eluent: hexane/EtOAc 5/1) to yield 0.48 g of 2-chloro-4-1-pyrrolyl)benzoic acid methyl ester. ESMS: m/z 236 (MH$^-$).

2)The product obtained above was hydrolyzed with LiOH to give the title compound. ESMS: m/z 220 (M–H)$^-$.

Reference Example 32

2-Chloro-4-(2-trifluoroacetyl-1-pyrrolyl)benzoic acid

1) Trifluoroacetic anhydride (0.55 mL) was added to a solution of 2-chloro-4-(1-pyrrolyl)benzoic acid methyl ester (0.3 g) in CH$_2$Cl$_2$ (5 mL) and the mixture was stirred at room temperature for 4 h. The mixture was diluted with CH$_2$Cl$_2$ and the mixture was stirred with satd. NaHCO$_3$ for 30 min. The organic layer was separated and washed with brine, dried (MgSO$_4$), filtered and evaporated. The residue was purified by column chromatography (silica gel; eluent: hexane/EtOAc 5/1) to yield 0.4 g of 2-chloro-4-(2-trifluoroacetyl-1-pyrrolyl)benzoic acid methyl ester. ESMS: m/z 330 (M–1).

2) The product obtained above was hydrolyzed with LiOH to give the title compound. ESMS: m/z 318 (MH$^+$).

Reference Example 33

2-Chloro-4-(2,5-dichloro-1-pyrrolyl)benzoic acid

1) N-Chlorosuccinimide (0.56 g) was added under N$_2$ to an ice-cold solution of 2-chloro-4-(1-pyrrolyl)benzoic acid methyl ester (0.5 g) in THF (7 mL). The mixture was warmed up to room temperature and stirred overnight. THF was removed and the residue was treated with Et$_2$O and filtered. The filtrate was evaporated and the residue was purified by column chromatography (silica gel; eluent: hexane/EtOAc 10/1) to yield 0.61 g of 2-chloro-4-(2,5-dichloro-1-pyrrolyl)benzoic acid methyl ester. ESMS: m/z 306 (MH$^+$).

2) The product obtained above was hydrolyzed with LiOH to give the title compound. ESMS: m/z 290 (MH$^+$).

Reference Example 34

2-Chloro-4-(2-formyl-1-pyrrolyl)benzoic acid

1) A solution of DMF (0.1 mL) in CH$_2$Cl$_2$ (2 mL) was added dropwise with stirring to a solution of oxalyl chloride (0.2 mL) in CH$_2$Cl$_2$ (16 mL) at −30° C. under N$_2$. The mixture was stirred for 15 min and a solution of 2-chloro-4-(1-pyrrolyl)benzoic acid methyl ester (0.5 g) in DMF (4 mL) was added. The mixture was stirred at that temperature for 3 h and allowed to warm to room temperature. The mixture was stirred overnight and evaporated. The residue was partitioned between EtOAc and 0.2 M NaOAc. The EtOAc layer was separated and the aqueous solution was extracted with EtOAc. The combined EtOAc layer was washed with brine, dried (MgSO$_4$), filtered and evaporated. The residue was purified by column chromatography (silica gel; eluent: hexane/EtOAc 3/1) to yield 2-chloro-4-(2-formyl-1-pyrrolyl)benzoic acid methyl ester (0.41 g). ESMS: 264 (MH$^+$).

2) The product obtained above was hydrolyzed with LiOH to give the title compound. ESMS: m/z 248 (M−H)$^−$.

Reference Example 35

2-Chloro-4-[N-methyl-N-(methylsulfonyl)amino]benzoic acid

1) A solution of di-tert-butyl dicarbonate (1.39 g) in dioxane (15 mL) was added dropwise to an ice-cold solution of 4-amino-2-chlorobenzoic acid (1.0 g) in 1N NaOH (12.8 mL). The mixture was allowed to warm to room temperature and stirred overnight. Dioxane was removed and the aqueous solution was extracted with Et$_2$O. The aqueous solution was acidified with 1N HCl to pH ~2. The precipitated solid was collected by filtration, washed with 1N HCl and water, and dried under vacuum to yield 4-(tert-butoxycarbonylamino)-2-chlorobenzoic acid (1.13 g). ESMS: m/z 294 (MH$^+$).

2) NaOMe (0.16 g) was added to a solution of the product obtained above (0.36 g) in DMF (10 mL) under N$_2$. The mixture was cooled to 0° C., and MeI (0.5 mL) was added. The mixture was stirred overnight at room temperature. NaOMe (0.14 g) and MeI (0.55 mL) were added and the mixture stirred for 6 h. THF was removed and the residue was partitioned between EtOAc and water. The EtOAc layer was separated and the aqueous layer was extracted with EtOAc. The combined EtOAc extract was washed with brine, dried (MgSO$_4$), filtered and evaporated. The residue was purified by column chromatography (silica gel; eluent: hexane/EtOAc 1/1) to yield 2-chloro-4-[N-methyl-N-(tert-butoxycarbonyl)amino]benzoic acid methyl ester (0.38 g). ESMS: m/z 322 (M+Na)$^+$.

3) A solution of the product obtained above in CH$_2$Cl$_2$ (10 mL) was treated with TFA (5 mL) for 2 h. The mixture was evaporated and the residue was taken up with EtOAc. The EtOAc solution was washed successively with 10% Na$_2$CO$_3$ and brine, dried (MgSO$_4$), filtered and evaporated to give 0.25 g 2-chloro-4-(methylamino)benzoic acid methyl ester. ESMS: m/z 200 (MH$^+$).

4) Methanesulfonyl chloride (0.2 mL) was added under N$_2$ to a solution of the product obtained above (0.25 g) and pyridine (0.2 mL) in CH$_2$Cl$_2$ (20 mL) and the mixture was heated at 40° C. for 4 h. Pyridine (0.2 mL) and methanesulfonyl chloride (0.2 mL) were added and the mixture was heated for 2 h. The mixture was diluted with CH$_2$Cl$_2$ and the solution was washed with 1N HCl and water, dried (MgSO$_4$), filtered and evaporated. The residue was purified by column chromatography (silica gel; eluent: hexane/EtOAc 3/1-1/1) to give 2-chloro-4-[N-methyl-N-(methanesulfonyl)amino]benzoic acid methyl ester (0.26 g). ESMS: m/z 278 (MH$^+$).

5) The product obtained above was hydrolyzed with LiOH to give the title compound. ESMS: m/z 264 (MH$^+$).

Reference Example 36

2-Chloro-4-thioureidobenzoic acid

1) Benzoyl thiocyanate was generated by refluxing a solution of benzoyl chloride (0.31 mL) and ammonium thiocyanate (0.20 g) in acetone (15 mL) for 30 min. To this solution was added a solution of 4-amino-2-chlorobenzoic acid methyl ester (0.5 g) in CH$_3$CN (10 mL) and the mixture was refluxed for 5 h. The solvent was removed and the residue was partitioned between CH$_2$Cl$_2$ and water. The organic layer was separated, washed with brine, dried and evaporated. The residue was purified by column chromatography to yield 2-chloro-4-(3-benzoylthioureido)benzoic acid methyl ester (0.71 g). ESMS: 349 (MH$^+$).

2) The product obtained above was hydrolyzed with LiOH to give the title compound. ESMS: m/z 231 (MH$^+$).

Reference Example 37

2,6-Dichloro-4-phenyl benzoic acid

1) To a solution of 2,6-dichloro-4-bromobenzoic acid methyl ester (0.55 g) in THF (10 mL) was added benzeneboronic acid (1.30 g), Pd(PPh$_3$)$_4$ (0.16 g) and 2M Na$_2$CO$_3$ (5 mL). The mixture was refluxed for 4 h under N$_2$. After cooling, the mixture was diluted with EtOAc and washed with water and brine. The organic layer was dried (Na$_2$SO$_4$), filtered, and concentrated. The residue was purified by preparative TLC (silica gel; eluent: hexane to EtOAc/hexane 1/1) to yield crude 2,6-dichloro-4-phenylbenzoic acid methyl ester (0.57 g). ESMS: m/z 281 (MH$^+$).

2) The product obtained above was hydrolyzed with LiOH to give the title compound. ESMS: m/z 267 (MH$^+$), 265 (M−H)$^−$.

Reference Example 38

2,6-Dichloro-4-[2-(N-methyl)pyrrolyl]benzoic acid
(J. Med. Chem. 41, 2019 (1998))

1) 2,6-Dichloro-4-[2-(N-tert-butoxycarbonyl)pyrrolyl]benzoic acid methyl ester was obtained in a similar manner as described in Reference Example 37-1) by replacing benzeneboronic acid with 2-(N-tert-butoxycarbonyl)pyrroleboronic acid.

2) To a solution of the product obtained above in CH$_2$Cl$_2$ (5 mL) was added TFA (5 mL). After 2 h under N$_2$, the mixture was diluted with CH$_2$Cl$_2$, washed with water and brine, dried (Na$_2$SO$_4$), filtered, and concentrated to give 2,6-dichloro-4-(2-pyrrolyl)benzoic acid methyl ester.

3) To a solution of the product obtained above (0.20 g) in THF (5 mL) were added NaH (0.07 g) and MeI (0.14 mL).

After stirring 2 h at room temperature, the mixture was diluted with EtOAc and washed with water and brine. The organic layer was dried ($Na_2SO_4$), filtered and concentrated. The residue was purified by preparative TLC (silica gel; eluent: EtOAc/hexane 1/10) to yield 2,6-dichloro-4-[2-(N-methyl)pyrrolyl]benzoic acid methyl ester (0.088 g).

4) The product obtained above was hydrolyzed with LiOH to give the title compound.

Reference Example 39

3-Bromo-2,6-dichlorobenzoic acid

1) To a solution of 2,6-dichloro-4-aminobenzoic acid methyl ester (2.80 g) in $CH_2Cl_2$ (20 mL) at −10° C. was added a solution of tetrabutylammonium tribromide (6.94 g) in $CH_2Cl_2$ (30 mL) dropwise at −10° C. After 2 h, the mixture was warmed to room temperature, washed with satd. $NaHCO_3$ and brine, dried ($Na_2SO_4$), filtered, and concentrated. The residue was purified by column chromatography (silica gel; eluent: EtOAc/hexane 1:4) to yield 2,6-dichloro-3-bromo-4-aminobenzoic acid methyl ester (2.99 g). ESMS: m/z 298 ($MH^+$).

2) To a mixture of the product obtained above (2.99 g) in $H_2SO_4$ (10 mL) and water (20 mL) at 0° C. was added $NaNO_2$ (0.73 g). After 15 min, the mixture was treated with $H_3PO_2$. After 60 min, the mixture was extracted with EtOAc. The extract was washed with satd. $NaHCO_3$ and brine, dried ($Na_2SO_4$), filtered, and concentrated. The residue was purified by column chromatography (silica gel; eluent: hexane to EtOAc/hexane 1:10) to yield 2,6-dichloro-3-bromobenzoic acid methyl ester (2.11 g). ESMS: m/z 282 ($MH^+$).

3) The product obtained above was hydrolyzed with LiOH to give the title compound. ESMS: m/z 268 ($MH^+$) and 266 ($M^-$−1).

Reference Example 40

2-Chloro-4-(tert-butoxycarbonyl)benzoic acid 1) 3-Chloro-4-methoxycarbonylbenzoic acid (0.24 g) was dissolved in DMF (2.5 mL) under $N_2$ then CDI (0.36 g) was added and the resulting mixture was stirred at 40° C. for 2 h. t-BuOH (0.54 mL) and DBU (0.33 mL) were added and the resulting mixture was stirred at 40° C. for 2 days. The mixture was evaporated and the residue was taken up with AcOEt, washed with 1N HCl and sat. $NaHCO_3$, dried ($MgSO_4$), filtered and evaporated. The residue was purified by column chromatography (silica gel; eluent: toluene) to give 2-chloro-4-(tert-butoxycarbonyl)benzoic acid methyl ester (216 mg).

2) The product obtained above was hydrolyzed with LiOH to give the title compound.

Reference Example 41

4-(N,N-Dimethylsulfamoyl)amino-2-chlorobenzoic acid

1) Pyridine (0.4 mL) was added to a solution of methyl 4-amino-2-chlorobenzoate (0.3 g) in $CH_2Cl_2$ (10 mL) at 0° C. under $N_2$. N,N-Dimethylsulfamoyl chloride (0.21 mL) was added and the mixture was stirred at room temperature for 16 hours and refluxed for 5 hours. DMAP (0.4 g) was added and the mixture was stirred for 3 hours. The mixture was diluted with $CH_2Cl_2$ (100 mL), washed successively with 1N HCl, brine, satd. NaHCO3 and brine, dried and evaporated. The residue was purified by flash column chromatography (silica gel; eluent: EtOAc/hexane 1:3) to give 0.31 g of methyl 4-(N,N-dimethylsulfamoyl)amino-2-chlorobenzoate. ESMS: m/z 293 ($MH^+$)

2) The product obtained above was hydrolyzed with LiOH in a similar manner as described in Example 1-5) to give the title compound. ESMS: m/z 279 ($MH^+$)

Reference Example 42

Trimethyl-(2-cyano-3-thienyl)tin

A mixture of 3-bromothiophene-2-carbonitrile (385 mg), hexamethylditin (615 mg) and $Pd(PPh_3)_4$ (116 mg) in toluene (8 mL) was stirred at 130° C. under $N_2$ for 16 h. The organic solvent was evaporated under reduced pressure, and the residue was purified by column chromatography (silica gel; eluent: AcOEt-hexane 1:20) to give the title compound (406 mg).

Reference Example 43

2,6-Di(methoxymethoxy)benzeneboronic acid

1) DIEA (26 mL) and methoxymethoxy chloride (8.20 mL) were added to a suspension of resorcinol (3.65 g) in $CH_2Cl_2$ (40 mL) under $N_2$ at 0° C. The mixture was stirred at the same temperature for 10 min and stirred at room temperature for 16 hours. DIEA (13 mL) and methoxymethoxy chloride (4 mL) were added to the mixture and the mixture was stirred for 1 hour. The mixture was added to water and extracted with $CHCl_3$. The extract was dried ($MgSO_4$) and evaporated, and the residue was purified by flash column chromatography (silica gel; eluent: EtOAc/hexane 15%) to give 1,3-di(methoxymethoxy)benzene (2.44 g).

2) The product obtained above was treated in a similar procedure as described in Example 7-1) to give the title compound.

RPMI-CS-1 Cell Adhesion Assay

The following assay established the activity of the present compounds in inhibiting $β_7$-mediated cell adhesion in a representative in vitro system. This assay measures the adhesive interactions of a B-cell line, RPMI, known to express $α_4β_7$ (Erle et al., *J. Immunol.* 153: 517–528 (1994)), to the alternatively spliced region of fibronectin referred to as CS-1, in the presence of test compounds. The test compounds were added in increasing concentrations to RPMI cells and then the cell-compound mixture was added to CS-1 coated microwells. The plates were incubated, washed and the percentage of attached cells were quantitated. The present assay directly demonstrates the cell adhesion inhibitory activity and adhesion modulatory activity of the present compounds.

RPMI-CS-1 Assay

The CS-1 derived peptide, CLHPGEILDVPST, and the scrambled control peptide, CLHGPIELVSDPT, were synthesized at Tanabe Research Laboratories, USA, Inc. on a Beckman 990 synthesizer using t-Boc methodology. The peptides were immobilized onto microtiter plates using the heterobifunctional crosslinker 3-(2-pyridyldithio)propionic acid N-hydroxysuccinimide ester (SPDP) as reported (Pierschbacher, et al., *Proc. Natl. Acad. Sci. USA* 80: 1224–1227 (1983)). Microtiter plates were coated with 20 μg/ml human serum albumin (HSA) for 2 hours at room temperature, washed once with PBS and derivatized with 10 μg/ml SPDP for 1 hour. After washing, 100 μl of a 100 μg/ml cysteine containing peptide solution which had been recently dissolved was added to the wells and allowed to crosslink to the plates overnight at 4≦ C. Unbound peptide was removed from the plates by washing with PBS. To block non-reacted sites, the plates were coated with 100 μl of a 2.5 mg/ml BSA solution in PBS for one hour at 37° C. 100 μl of RPMI cells ($2.5 \times 10^6$ cells/ml) in Dulbecco's Modified Eagles Medium (DMEM) plus 0.25% ovalbumin were added to peptide coated dishes and incubated for 1 hour at 37° C. Following this incubation, the plates were washed with PBS three times using an EL404 plate washer and the number of adherent cells was quantitated by measuring enzymatic activity of endogenous N-acetyl-hexosaminidase (Landegren, *J. Immunol. Methods*, 67: 379–388 (1984)). To do this, the enzyme substrate p-nitrophenyl-N-acetyl-β-D-glucoseaminide is dissolved at 7.5 mM in 0.1 M citrate buffer pH 5 and then mixed with an equal volume of 0.5% Triton X100. 50 μl of the substrate solution was added to the plates and the plates were incubated at 37° C. for 60 minutes. The reaction was stopped by the addition of 100 μl 50 mM EDTA buffer pH 10.4. The amount of liberated p-nitrophenol was quantitated by reading the optical density at 405 nm using a vertical pathway spectrophotometer to quantitate attachment (VMAX Kinetic Microplate Reader, Molecular Devices, Menlo Park, Calif.). This procedure is a modification of a previously published method (Cardarelli et al., *J. Biol. Chem.* 269: 18668–18673 (1994)).

In this assay, $IC_{50}$ value ranges (μM) are depicted by A, B, C and D. These ranges as follows.

$$D > 5 \geq C > 1 \geq B > 0.3 \geq A$$

The following TABLE 31 illustrates the $IC_{50}$ values for of the present invention in the RPMI-CS-1 assay. The ranges are as described above.

TABLE 31

| Example Number | RPMI-CS-1 |
| --- | --- |
| 1A | B |
| 1B | A |
| 2 | C |
| 3 | A |
| 4A | C |
| 4B | B |
| 5 | C |
| 6 | D |
| 7A | A |
| 7B | A |
| 8 | A |
| 9 | A |
| 10 | A |
| 11 | A |
| 12 | A |
| 13 | A |
| 14 | A |
| 15 | B |
| 16 | A |
| 17 | A |
| 18 | B |
| 19 | C |
| 20 | A |
| 21 | A |
| 22 | C |
| 23 | B |
| 24 | A |
| 25 | B |
| 26 | B |
| 27 | A |
| 28 | B |
| 29 | C |
| 30 | B |
| 31 | A |
| 32 | A |
| 33 | B |
| 34 | C |
| 35 | C |
| 36 | A |
| 37 | B |
| 38 | B |
| 39 | B |
| 40 | B |
| 41 | C |
| 42 | B |
| 43 | C |
| 44 | B |
| 45 | A |
| 46 | A |
| 47 | A |
| 48 | C |
| 49 | B |
| 50 | A |
| 51 | B |
| 52 | D |
| 53 | C |
| 54 | B |
| 55 | C |
| 56 | B |
| 57 | C |
| 58 | B |
| 59 | C |
| 60 | B |
| 61 | D |
| 62 | A |
| 63 | B |
| 64 | A |
| 65 | A |
| 66 | A |
| 67 | B |
| 68 | A |
| 69 | A |
| 70 | A |
| 71 | A |
| 72 | B |
| 73 | A |
| 74 | B |
| 75 | A |
| 76 | D |
| 77 | A |
| 78 | B |
| 79 | A |
| 80 | A |
| 81 | D |
| 82 | D |
| 83 | B |
| 84 | C |
| 85 | B |
| 86 | A |
| 87 | B |
| 88 | C |
| 89 | B |
| 90 | B |
| 91 | C |
| 92 | C |
| 93 | D |
| 94 | C |
| 95 | C |
| 96 | B |
| 97 | B |
| 100 | C |
| 101 | D |
| 102 | D |
| 103 | D |
| 104 | D |
| 105 | D |
| 106 | C |
| 107 | C |
| 108 | C |
| 109 | D |

TABLE 31-continued

| Example Number | RPMI-CS-1 |
|---|---|
| 110 | D |
| 111 | C |
| 112 | B |
| 113 | A |
| 114 | B |
| 115 | C |
| 116 | C |
| 117 | C |
| 118 | C |
| 119 | D |
| 120 | D |
| 121 | C |
| 122 | C |
| 123 | C |
| 124 | C |
| 125 | C |
| 126 | C |
| 127 | D |
| 128 | B |
| 129 | C |
| 130 | D |
| 131 | A |
| 132 | A |
| 133 | A |
| 134 | A |
| 135 | A |
| 136 | B |
| 137 | B |
| 138 | A |
| 139 | A |
| 140 | B |
| 141 | B |
| 142 | A |
| 143 | A |
| 144 | A |
| 145 | C |
| 146 | B |
| 147 | A |
| 148 | A |
| 149 | A |
| 150 | A |
| 151 | A |
| 152A | A |
| 152B | A |
| 152C | B |
| 153A | A |
| 153B | A |
| 154 | A |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | B |
| 177 | A |
| 178 | A |
| 179 | A |
| 180 | A |
| 181 | B |
| 182 | A |
| 183 | A |
| 184 | A |
| 186 | B |
| 187 | A |
| 188 | A |
| 189 | A |
| 190 | A |
| 191 | A |
| 192 | A |
| 193 | A |
| 194 | C |
| 195 | B |
| 196 | A |
| 197 | B |
| 198 | A |
| 199 | A |
| 200 | A |
| 201 | A |
| 202 | A |
| 203 | A |
| 204 | A |
| 205 | A |
| 206 | A |
| 207 | A |
| 208 | A |
| 209 | A |
| 210 | C |
| 211 | A |
| 212 | C |
| 213 | C |
| 214 | B |
| 215 | B |
| 216 | C |
| 217 | C |
| 218 | C |
| 219 | B |
| 220 | A |
| 221 | C |
| 222 | A |
| 223 | A |
| 224 | C |
| 225 | C |
| 226 | A |
| 227 | A |
| 228 | A |
| 229 | A |
| 230 | B |
| 231 | A |
| 232 | A |
| 233 | B |
| 234 | A |
| 235 | A |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | A |
| 250 | A |
| 251 | A |
| 252 | A |
| 253 | A |
| 254 | A |
| 255 | A |
| 256 | A |
| 257 | A |
| 258 | A |
| 259 | A |
| 262 | A |

TABLE 31-continued

| Example Number | RPMI-CS-1 |
|---|---|
| 263A | A |
| 263B | A |
| 264 | A |
| 265 | A |
| 266 | A |
| 267 | D |
| 268 | C |
| 269 | D |
| 270 | A |
| 271 | A |
| 272 | B |
| 273 | C |
| 274 | C |
| 275 | D |
| 276 | D |
| 277 | A |
| 278 | A |
| 279 | A |
| 280 | A |
| 281 | C |
| 282 | C |
| 283 | C |
| 284 | C |
| 285 | A |
| 286 | A |
| 287 | B |
| 288 | C |
| 289 | B |
| 290 | C |
| 291 | C |
| 292 | C |
| 293 | C |
| 294 | C |
| 295 | C |
| 296 | A |
| 297 | A |
| 298 | A |
| 299 | A |
| 300 | B |
| 301 | A |
| 302 | A |
| 303 | A |
| 304 | A |
| 305 | B |
| 306 | A |
| 307 | A |
| 308 | A |
| 309 | A |
| 310 | A |
| 311 | A |
| 312 | A |
| 316 | A |
| 317 | A |
| 319 | A |
| 320 | A |
| 321 | A |
| 322 | A |
| 323 | A |
| 324 | A |
| 325 | A |
| 326 | A |
| 327 | A |
| 328 | A |
| 329 | C |
| 331 | A |
| 332 | B |
| 333 | A |
| 334 | A |
| 335 | B |
| 336 | A |
| 337 | A |
| 338 | A |
| 339 | A |
| 340 | A |
| 341 | A |
| 342 | A |
| 343 | C |
| 344 | C |
| 345 | B |
| 346 | A |
| 347 | A |
| 348 | A |
| 349 | A |
| 350 | A |
| 351 | A |
| 352 | B |
| 353 | A |
| 354 | A |
| 355 | A |
| 356 | A |

What is claimed is:

1. A compound of the formula [I]:

$$[I]$$

wherein
  Ring A is a benzene ring;
  Q is a bond;
  N is an integer of 1 or 2;
  W is a —CH═CH— group;
  Z is oxygen atom or sulfur atom;
  $R^1$, $R^2$, and $R^3$ are the same or different and are selected from the group consisting of:
    hydrogen atom,
    halogen atom,
    a substituted or unsubstituted lower alkoxy group,
    a nitro group,
    a substituted or unsubstituted amino group,
    a carboxyl group or an amide or an ester thereof,
    a cyano group,
    a lower alkylthio group,
    a lower alkanesulfonyl group,
    a substituted or unsubstituted sulfamoyl group,
    a substituted or unsubstituted aryl group,
    a substituted or unsubstituted heterocyclic group, and
    hydroxyl group,
  or two of $R^1$, $R^2$, and $R^3$ may combine each other at the terminal thereof to form a lower alkylenedioxy group;
  $R^4$ is a carboxyl group, or an amide or an ester thereof;
  $R^5$ is a group selected from the group consisting of:
    hydrogen atom,
    a nitro group,
    a substituted or unsubstituted amino group,
    a hydroxyl group,
    a lower alkanoyl group,
    a substituted or unsubstituted lower alkyl group,
    a lower alkoxy group,
    a halogen atom, and
    2-oxopyrrolidinyl group;
  $R^6$ is a substituted or unsubstituted phenyl group; or a pharmaceutically acceptable salt thereof.

2. The compound according to claim 1, wherein the chemical structure is formula [I-A]:

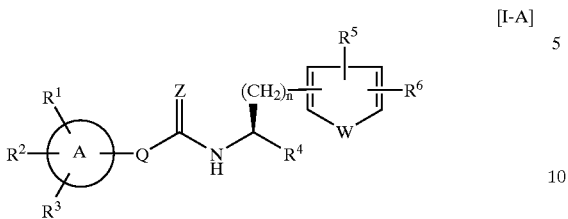

wherein symbols are the same as defined above.

3. The compound according to claim 1, with the proviso that Ring A is substituted in at least one of 2- and 6-positions.

4. The compound according to claim 1, wherein the chemical structure is formula [I-B]:

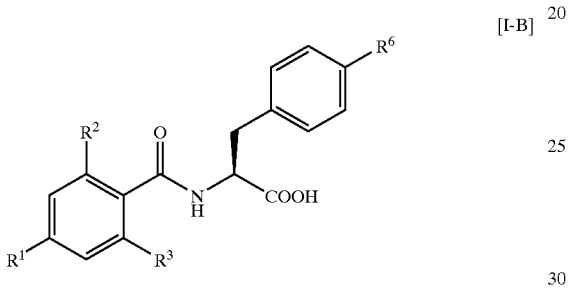

wherein symbols are the same as defined above.

5. The compound according to claim 4, wherein $R^1$ is hydrogen atom, a halogen atom, carboxyl group, carbamoyl group, nitro group, a substituted or unsubstituted amino group, a substituted or unsubstituted heterocyclic ring;
$R^2$ is hydrogen atom, or a halogen atom;
$R^3$ is hydrogen atom, or a halogen atom;
$R^6$ is a phenyl group which may be substituted at 2-, 4-, and/or 6-position of the phenyl group by a group selected from the group consisting of:
1) a halogen atom,
2) a substituted or unsubstituted lower alkoxy group,
3) a substituted or unsubstituted lower alkyl group,
4) a substituted or unsubstituted amino group,
5) a substituted or unsubstituted carbamoyl group, and
6) a substituted or unsubstituted sulfamoyl group.

6. The compound according to claim 1, wherein
$R^1$ $R^2$, and $R^3$ are selected from the group consisting of:
hydrogen atom;
a halogen atom,
a lower alkoxy group which may be substituted by a halogen atom,
a nitro group,
an amino group which may be substituted by 1–2 groups selected from the group consisting of 1) a lower alkyl group, 2) a lower alkanoyl group, 3) a halogenobenzoyl group, 4) a lower alkoxycarbonyl group, 5) a lower alkanesulfonyl group which may be substituted by a halogen atom, 6) a benzenesulfonyl group which may be substituted by a lower alkyl group, a trihalogeno-lower alkyl group, a halogen atom or a lower alkoxy group, 7) thiophenesulfonyl group, 8) a carbamoyl group which may be substituted by a lower alkyl group, a lower alkyl-phenyl group, 9) a thiocarbamoyl group which may be substituted by a lower alkyl group, phenyl group, a phenyl-lower alkyl group, 10) thiazolinyl group, and 11) a sulfamoyl group which may be substituted by a lower alkyl group;
a carboxyl group,
a carbamoyl group which may be substituted by a lower alkanesulfonyl group,
a lower alkoxycarbonyl group,
a cyano group,
a lower alkylthio group,
a lower alkanesulfonyl group,
a sulfamoyl group,
a phenyl group,
a pyrrolidinyl group which may be substituted by oxo group,
a pyrrolyl group which may be substituted by a group selected from the group consisting of 1) a lower alkanoyl group which may be substituted by a halogen atom, 2) a halogen atom, 3) formyl group, and 4) a lower alkyl group which may be substituted by hydroxy group,
a thienyl group,
an isoxazolyl group which may be substituted by a lower alkyl group,
a thiazolyl group,
a pyrazolyl group,
a pyrazinyl group,
a pyridyl group, and
hydroxyl group;
$R^4$ is selected from the group consisting of:
carboxyl group,
a lower alkoxycarbonyl group which may be substituted by 1) pyridyl group or 2) an amino group which may be substituted by a lower alkyl group,
a lower cycloalkoxy carbonyl group, and
a carbamoyl group which may be substituted by a hydroxy group or a lower alkanesulfonyl group;
$R_5$ is selected from the group consisting of:
hydrogen atom,
a nitro group,
an amino group which may be substituted by a lower alkanoyl group, a lower alkoxycarbonyl group or a lower alkanesulfonyl group,
a hydroxyl group,
a lower alkanoyl group,
a lower alkyl group which may be substituted by 1) hydroxyl group, or 2) an imino group which is substituted by hydroxyl group or a lower alkoxy group,
a lower alkoxy group,
a halogen atom, and
2-oxopyrrolidinyl group;
$R^6$ is a phenyl group which may have 1–5 substituents selected from the group consisting of:
1) a halogen atom,
2) a nitro group,
3) a formyl group,
4) a hydroxyl group,
5) a carboxyl group,
6) a lower alkoxy group which may be substituted by a group selected from the group consisting of i) a carboxyl group or an amide or an ester thereof, ii) hydroxyl group, iii) a cyano group, iv) a halogen atom, v) an amino group which may be substituted by a lower alkyl group, vi) a pyridyl group, vii) a thiazolyl group which may be substituted by a lower alkyl group, viii) an isoxazolyl group which may be substituted by a lower alkyl group, ix) a piperidyl group which may be substituted by a lower alkyl group, x) a pyrrolidinyl group which may be substituted by a lower alkyl group, xi) a phenyl group which may be substituted by a halogen atom, xii) a furyl group, xiii) a thienyl group, and xiv) a lower alkoxy group,
7) a lower alkyl group which may be substituted by a group selected from the group consisting of i) a halogen atom, ii) hydroxyl group, iii) carboxyl group or an amide or an ester thereof, iv) a lower alkoxy group, v) an amino group which may be substituted by 1–2 groups selected from the group consisting of a lower alkyl group, a hydroxy-lower alkyl group, a (lower alkylamino)-lower alkyl group, phenyl-lower alkyl group, a phenyl group, and a pyridyl group, vi) a piperidinyl group which may be substituted by a lower alkylenedioxy group, an oxo group or a hydroxy group, vii) a morpholino group which may be substituted by a lower alkyl group, viii) thiomorpholino group which may be oxidized, ix) piperazinyl group which may be substituted by a lower alkyl group, a hydroxy-lower alkyl group, a lower alkanoyl group or a phenyl-lower alkyl group, x) pyrrolidinyl group, which may be substituted by one group, and xi) an imidazolidinyl group which may be substituted by 1–3 groups selected from the group consisting of a lower alkyl group and oxo group,
8) a lower alkenyl group which may be substituted by carboxyl group or an amide or an ester thereof,
9) an amino group which may be substituted by a group selected from the group consisting of i) a phenyl group, ii) a lower alkoxycarbonyl group, iii) a lower alkanesulfonyl group, iv) a carbamoyl group which may be substituted by a lower alkyl group or a lower alkyl-phenyl group, v) a lower alkanoyl group, vi) a lower alkyl group, vii) a lower alkenyl group, and viii) a thiocarbamoyl group which may be substituted by a lower alkyl group,
10) a carbamoyl group which may be substituted by a lower alkyl group, a hydroxy-lower alkyl group, a morpholino-lower alkyl group, a phenyl-lower alkyl group or a lower alkanesulfonyl group,
11) a sulfamoyl group which may be substituted by a group consisting of i) a lower alkyl group, ii) a benzoyl group, iii) a lower alkoxycarbonyl group, and iv) a lower alkanoyl group,
12) a lower alkenyloxy group,
13) a lower alkylenedioxy group,
14) a piperazinylcarbonyl group which may be substituted by a lower alkyl group,
15) a lower alkanoyl group,
16) cyano group,
17) a lower alkylthio group,
18) a lower alkanesulfonyl group,
19) a lower alkylsulfinyl group, and
20) a group of the formula:

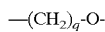

wherein q is an integer of 2 or 3.
7. The compound according to claim 6, wherein $R^1$ is selected from the group consisting of:
hydrogen atom,
a halogen atom,
a lower alkoxy group,
nitro group,
an amino group which may be substituted by a group selected from the group consisting of 1) a lower alkyl group, 2) a lower alkanoyl group, 3) a lower alkoxycarbonyl group, 4) a lower alkanesulfonyl group which may be substituted by a halogen atom, 5) a benzenesulfonyl group which may be substituted by a lower alkyl group, a trihalogeno-lower alkyl group, a halogen atom or a lower alkoxy group, 6) thiophenesulfonyl group, 7) a carbamoyl group which may be substituted by a lower alkyl group or a lower alkyl-phenyl group, 8) a thiocarbamoyl group which may be substituted by a lower alkyl group, and 9) a sulfamoyl group which may be substituted by a lower alkyl group,
carboxyl group
a carbamoyl group which may be substituted by a lower alkanesulfonyl group,
a lower alkanesulfonyl group,
a sulfamoyl group,
phenyl group,
a pyrrolidinyl group which may be substituted by oxo group,
a pyrrolyl group which may be substituted by a lower alkyl group,
a thienyl group,
an isoxazolyl group which may be substituted by a lower alkyl group,
a thiazolyl group
a pyrazolyl group,
a pyrazinyl group,
a pyridyl group, and
a hydroxyl group;
$R^2$ is hydrogen atom, or a halogen atom;
$R^3$ is hydrogen atom, or a halogen atom;
$R^4$ is
a carboxyl group,
a lower alkoxycarbonyl group which may be substituted by a lower alkyl-amino group, or
a carbamoyl group which may be substituted by a lower alkanesulfonyl group;
$R^5$ is selected from t he group consisting of:
hydrogen atom,
an amino group which may be substituted by a lower alkanoyl group, a lower alkoxycarbonyl group or a lower alkanesulfonyl group,
a lower alkanoyl group,
a lower alkyl group which may be substituted by 1) hydroxyl group, or 2) an imino group which is substituted by hydroxyl group or a lower alkoxy group,
a lower alkoxy group, and
a halogen atom;
$R^6$ is a phenyl group which may have 1–5 substituents selected from the group consisting of:
a halogen atom,
a formyl group,
a hydroxyl group,
a lower alkoxy group which may be substituted by 1) a carboxyl group, 2) a hydroxyl group, 3) a cyano group, 4) a halogen atom, 5) an amino group which may be substituted by a lower alkyl group, 6) a pyridyl group, 7) a phenyl group, 8) a thienyl group, or 9) a lower alkoxy group,
a lower alkyl group which may be substituted by 1) an amino group which may be substituted by a lower alkyl group, a hydroxy-lower alkyl group, a (lower alkylamino)-lower alkyl group or a phenyl group, 2) a piperidinyl group which may be substituted by a lower alkylenedioxy group, 3) a morpholino group which may be substituted by a lower alkyl group, 4) a thiomorpholino group in which sulfur atom may be oxidized, 5) a piperazinyl group which may be substituted by a lower alkyl group, a hydroxy-lower alkyl group, a lower alkanoyl group or a phenyl-lower alkyl group, 6) pyrrolidinyl group, which may be substituted by oxo group, or 7) an imidazolidinyl group which may be substituted by 1–3 groups selected from the group consisting of a lower alkyl group and oxo group, an amino group which may be substituted by 1) a lower alkoxycarbonyl group, 2) a lower alkanesulfonyl group, 3) a carbamoyl group which may be substituted by a lower alkyl group a lower alkyl-phenyl group, 4) a lower alkanoyl group, 5) a lower alkyl group, 6) a lower alkenyl group, or 7) a thiocarbamoyl group which may be substituted by a lower alkyl group, a carbamoyl group which may be substituted by 1) a lower alkyl group, 2) a hydroxy-lower alkyl group, 3) a morpholino-lower alkyl group, 4) a phenyl-lower alkyl group, or 5) a lower alkanesulfonyl group, a sulfamoyl group which may be substituted by a lower alkyl group, a lower alkenyloxy group, a lower alkylenedioxy group, a cyano group, a lower alkylthio group, and a lower alkanesulfonyl group.

8. The compound according to claim 5 or 7, wherein $R^1$ is 1) hydrogen atom, 2) a halogen atom, 3) a lower alkanoylamino group, 4) a lower alkoxycarbonylamino group, 5) a lower alkanesulfonylamino group which may be substituted by a halogen atom, 6) a benzenesulfonylamino group which may be substituted by a lower alkyl group, a trihalogeno-lower alkyl group, a halogen atom or a lower alkoxy group, 7) thiophenesulfonylamino group, 8) an ureido group which may be substituted by a lower alkyl group or a lower alkyl-phenyl group, 9) a lower alkyl-thioureido group, or 10) a lower alkylsulfamoylamino group, $R^2$ is a halogen atom, $R^3$ is hydrogen atom or a halogen atom, and $R^6$ is a phenyl group which may have 1–3 substituents selected from the group consisting of 1) a lower alkoxy group, 2) a lower alkyl group which may be substituted by a group selected from the group consisting of a lower alkylamino group, a hydroxy-lower alkylamino group, a lower alkylamino-lower alkylamino group, piperidinyl group, a lower alkyl-piperidinyl group, morpholino group, a lower alkyl-morpholino group, a thiomorpholino group, piperazinyl group, a lower alkyl-piperazinyl group, a lower alkanoyl-piperazinyl group, and a pyrrolidinyl group, 3) a sulfamoyl group which may be substituted by a lower alkyl group, 4) a carbamoyl group which may be substituted by a lower alkyl group.

9. The compound according to claim 8, wherein $R^1$ is hydrogen atom, $R^3$ is a halogen atom, and $R^6$ is 2-(lower alkoxy)phenyl group, 2,6-di(lower alkoxy)phenyl group, 2,6-di(lower alkoxy)-4-[[N,N-di(lower alkyl)amino]lower alkyl]phenyl group, 2,6-di(lower alkoxy)-4-[(4-lower alkyl-1-piperazinyl)lower alkyl]phenyl group, 2,6-di(lower alkoxy)-4-[1-piperidinyl-lower alkyl]phenyl group, 2,6-di(lower alkoxy)-4-[N,N-di(lower alkyl)carbamoyl]phenyl group or 2,6-di(lower alkoxy)-4-[(morpholino)lower alkyl]phenyl group.

10. The compound according to claim 9, wherein a lower alkoxy group is methoxy group.

11. N-(2,6-dichlorobenzoyl)-4-(2,6-dimethoxyphenyl)-L-phenylalanine;
N-(2,6-dichlorobenzoyl)-4-[2,6-dimethoxy-4-(piperidinomethyl)phenyl]-L-phenylalanine;
N-(2,6-dichlorobenzoyl)-4-[2,6-dimethoxy-4-[(4-methylpiperazinyl)amino]phenyl]-L-phenylalanine;
N-(2,6-dichlorobenzoyl)-4-[2,6-dimethoxy-4-(morpholinomethyl)phenyl]-L-phenylalanine;
N-(2,6-dichlorobenzoyl)-4-[2,6-dimethoxy-4-(N,N-dimethylamino)phenyl]-L-phenylalanine;
N-(2,6-dichlorobenzoyl)-4-[2,6-dimethoxy-4-(N,N-dimethylcarbamoyl)phenyl]-L-phenylalanine;
N-(2,6-dichloro-4-hydroxybenzoyl)-4-(2,6-dimethoxyphenyl)-L-phenylalanine;
N-(2,6-dichlorobenzoyl)-4-(2-ethoxy-6-methoxyphenyl)-L-phenylalanine;
N-(2,6-difluorobenzoyl)-4-(2-6,dimethoxyphenyl)-L-phenylalanine;
N-(2,6-dichlorobenzoyl)-4-(2,3-methylenedioxy-6-methoxyphenyl)-L-phenylalanine; -
N-(2,6-dichlorobenzoyl)-3-(1-hydroxyethy)-4-(2,6dimethoxyphenyl)-L-phenylalanine;
N-(2,6-dichlorobenzoyl)-4-(2,4,6-trimethoxyphenyl)-L-phenylalanine;
N-[2,6-dichloro-4-[(trifluoromethanesulfonyl)amino]benzoyl]-4-(2,6-dimethoxyphenyl)-L-phenylalanine; or
N-[2,6-dichloro-4-[(2-thienylsulfonyl)amino]benzoyl]-4-(2,6-dimethoxyphenyl)-L-phenylalanine;
or a lower alkyl ester thereof;
or pharmaceutically acceptable salt thereof.

12. A pharmaceutical composition which comprises a therapeutically effective amount of the compound as set forth in claim 1 and a pharmaceutically acceptable carrier or diluent.

13. A pharmaceutical composition which comprises a therapeutically effective amount of the compound as set forth in claim 2 and a pharmaceutically acceptable carrier or diluent.

14. A pharmaceutical composition which comprises a therapeutically effective amount of the compound as set forth in claim 3 and a pharmaceutically acceptable carrier or diluent.

15. A pharmaceutical composition which comprises a therapeutically effective amount of the compound as set forth in claim 4 and a pharmaceutically acceptable carrier or diluent.

16. A pharmaceutical composition which comprises a therapeutically effective amount of the compound as set forth in claim 5 and a pharmaceutically acceptable carrier or diluent.

17. A pharmaceutical composition which comprises a therapeutically effective amount of the compound as set forth in claim 6 and a pharmaceutically acceptable carrier or diluent.

18. A pharmaceutical composition which comprises a therapeutically effective amount of the compound as set forth in claim 7 and a pharmaceutically acceptable carrier or diluent.

19. A pharmaceutical composition which comprises a therapeutically effective amount of the compound as set forth in claim 8 and a pharmaceutically acceptable carrier or diluent.

20. A pharmaceutical composition which comprises a therapeutically effective amount of the compound as set forth in claim 9 and a pharmaceutically acceptable carrier or diluent.

21. A pharmaceutical composition which comprises a therapeutically effective amount of the compound as set forth in claim 10 and a pharmaceutically acceptable carrier or diluent.

22. The pharmaceutical composition comprising a therapeutically effective amount of:

N-(2,6-dichlorobenzoyl)-4-(2,6-dimethoxyphenyl)-L-phenylalanine;
N-(2,6-dichlorobenzoyl)-4-[2,6-dimethoxy-4-(1-piperidinomethyl)phenyl]-L-phenylalanine;
N-(2,6-dichlorobenzoyl)-4-[2,6-dimethoxy-4-[(4-methylpiperazinyl)amino]phenyl]-L-phenylalanine;
N-(2,6-dichlorobenzoyl)-4-[2,6-dimethoxy-4-(morpholinomethyl)phenyl]-L-phenylalanine;
N-(2,6-dichlorobenzoyl)-4-[2,6-dimethoxy-4-(N,N-dimethylamino)phenyl]-L-phenylalanine;
N-(2,6-dichlorobenzoyl)-4-[2,6-dimethoxy-4-(N,N-dimethylcarbamoyl)phenyl]-L-phenylalanine;
N-(2,6-dichloro-4-hydroxybenzoyl)-4-(2,6-dimethoxyphenyl)-L-phenylalanine;
N-(2,6-dichlorobenzoyl)-4-(2-ethoxy-6-methoxyphenyl)-L-phenylalanine;
N-(2,6-difluorobenzoyl)-4-(2-6,dimethoxyphenyl)-L-phenylalanine;
N-(2,6-dichlorobenzoyl)-4-(2,3-methylenedioxy-6-methoxyphenyl)-L-phenylalanine;
N-(2,6-dichlorobenzoyl)-3-(1-hydroxyethy)-4-(2,6-dimethoxyphenyl)-L-phenylalanine;
N-(2,6-dichlorobenzoyl)-4-(2,4,6-trimethoxyphenyl)-L-phenylalanine;
N-[2,6-dichloro-4-[(trifluoromethanesulfonyl)amino]benzoyl]-4-(2,6-dimethoxyphenyl)-L-phenylalanine; or -
N-[2,6-dichloro-4-[(2-thienylsulfonyl)amino]benzoyl]4-(2,6-dimethoxyphenyl)-L-phenylalanine;
or a lower alkyl ester thereof;
or a pharmaceutically acceptable salt thereof; and a pharmaceutically acceptable carrier or diluent.

23. A method for inhibiting the adhesion of a cell expressing an α4 integrin to MAdCAM-1, VCAM-1 or CS-1, which comprises
administering to a patient in need of such treatment an inhibitory amount of the compound as set forth in claim 1.

24. A method for inhibiting the adhesion of a cell expressing an α4 integrin to MAdCAM-1, VCAM-1 or CS-1, which comprises
administering to a patient in need of such treatment an inhibitory amount of the compound as set forth in claim 2.

25. A method for inhibiting the adhesion of a cell expressing an α4 integrin to MAdCAM-1, VCAM-1 or CS-1, which comprises
administering to a patient in need of such treatment an inhibitory amount of the compound as set forth in claim 3.

26. A method for inhibiting the adhesion of a cell expressing an α4 integrin to MAdCAM-1, VCAM-1 or CS-1, which comprises
administering to a patient in need of such treatment an inhibitory amount of the compound as set forth in claim 4.

27. A method for inhibiting the adhesion of a cell expressing an α4 integrin to MAdCAM-1, VCAM-1 or CS-1, which comprises
administering to a patient in need of such treatment an inhibitory amount of the compound as set forth in claim 5.

28. A method for inhibiting the adhesion of a cell expressing an α4 integrin to MAdCAM-1, VCAM-1 or CS-1, which comprises
administering to a patient in need of such treatment an inhibitory amount of the compound as set forth in claim 6.

29. A method for inhibiting the adhesion of a cell expressing an α4 integrin to MAdCAM-1, VCAM-1 or CS-1, which comprises
administering to a patient in need of such treatment an inhibitory amount of the compound as set forth in claim 7.

30. A method for inhibiting the adhesion of a cell expressing an α4 integrin to MAdCAM-1, VCAM-1 or CS-1, which comprises
administering to a patient in need of such treatment an inhibitory amount of the compound as set forth in claim 8.

31. A method for inhibiting the adhesion of a cell expressing an α4 integrin to MAdCAM-1, VCAM-1 or CS-1, which comprises
administering to a patient in need of such treatment an inhibitory amount of the compound as set forth in claim 9.

32. A method for inhibiting the adhesion of a cell expressing an α4 integrin to MAdCAM-1, VCAM-1 or CS-1, which comprises
administering to a patient in need of such treatment an inhibitory amount of the compound as set forth in claim 10.

33. A method for inhibiting the adhesion of a cell expressing an α4 integrin to MAdCAM-1, VCAM-1 or CS-1, which comprises
administering to a patient in need of such treatment an inhibitory amount of:

N-(2,6-dichlorobenzoyl)-4-(2,6-dimethoxyphenyl)-L-phenylalanine;
N-(2,6-dichlorobenzoyl)-4-[2,6-dimethoxy-4-(piperidinomethyl)phenyl]-L-phenylalanine;
N-(2,6-dichlorobenzoyl)-4-[2,6-dimethoxy-4-[(4-methylpiperazinyl)amino]phenyl]-L-phenylalanine;
N-(2,6-dichlorobenzoyl)-4-[2,6-dimethoxy-4-(morpholinomethyl)phenyl]-L-phenylalanine;
N-(2,6-dichlorobenzoyl)-4-[2,6-dimethoxy-4-(N,N-dimethylamino)phenyl]-L-phenylalanine;
N-(2,6-dichlorobenzoyl)-4-[2,6-dimethoxy-4-(N,N-dimethylcarbamoyl)phenyl]-L-phenylalanine;
N-(2,6-dichloro-4-hydroxybenzoyl)-4-(2,6-dimethoxyphenyl)-L-phenylalanine;
N-(2,6-dichlorobenzoyl)-4-(2-ethoxy-6-methoxyphenyl)-L-phenylalanine;
N-(2,6-difluorobenzoyl)-4-(2-6,dimethoxyphenyl)-L-phenylalanine;
N-(2,6-dichlorobenzoyl)-4-(2,3-methylenedioxy-6-methoxyphenyl)-L-phenylalanine;
N-(2,6-dichlorobenzoyl)-3-(1-hydroxyethy)-4-(2,6-dimethoxyphenyl)-L-phenylalanine;
N-(2,6-dichlorobenzoyl)-4-(2,4,6-trimethoxyphenyl)-L-phenylalanine;
N-[2,6-dichloro-4-[(trifluoromethanesulfonyl)amino]benzoyl]-4-(2,6-dimethoxyphenyl)-L-phenylalanine; or
N-[2,6-dichloro-4-[(2-thienylsulfonyl)amino]benzoyl]-4-(2,6-dimethoxyphenyl)-L-phenylalanine;
or a lower ester thereof;
or pharmaceutically acceptable salt thereof.

34. The method according to claim 24, wherein said patient suffers from a condition selected from the group consisting of rheumatoid arthritis, asthma, psoriasis, eczema, contact dermatitis and other skin inflammatory diseases, diabetes, multiple sclerosis, systemic lupus erythematosus (SLE), inflammatory bowel disease, and other diseases involving leukocyte infiltration of the gastrointestinal tract, or other epithelial lined tissues.

35. The method according to claim 34, wherein said condition is inflammatory bowel disease.

36. A process for preparing the compound of the formula [I]:

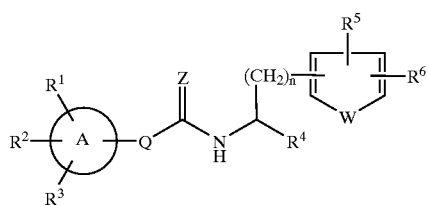

wherein the symbols are the same as defined in claim 1, or a pharmaceutically acceptable salt thereof, comprising:

(1) condensing a compound of the formula [II]:

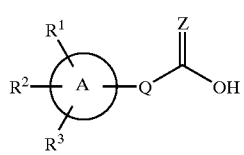

wherein the symbols are the same as defined above, a salt thereof or a reactive derivative thereof with a compound of the formula [III]:

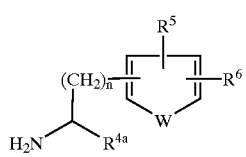

wherein $R^{4a}$ is an ester group, and other symbols are the same as defined above, or a salt thereof, (2) converting the ester group into a carboxyl group, if desired, and (3) converting the carboxyl group of the resulting compound into an ester group, an amide group or a pharmaceutically acceptable salt thereof, if further desired.

37. A process for preparing the compound of the formula [I]:

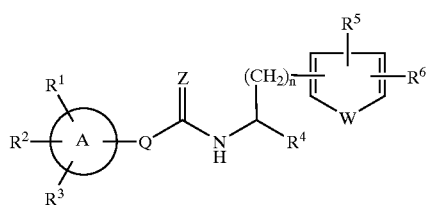

wherein the symbols are the same as defined in claim 1, or a pharmaceutically acceptable salt thereof, comprising:

(1) reacting a compound of the formula [IV]:

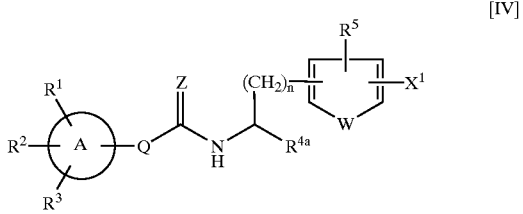

wherein $X^1$ is a leaving group, $R^{4a}$ is an ester group, and other symbols are the same as defined above, with a compound of the formula [V]:

wherein the symbols are the same as defined above, (2) converting the ester group into a carboxyl group, if desired, and (3) converting the carboxyl group of the resulting compound into an ester group, an amide group or a pharmaceutically acceptable salt thereof, if further desired.

38. A process for preparing the compound of the formula [I]

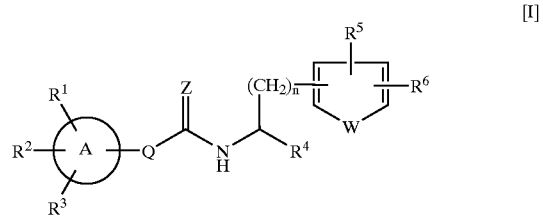

wherein the symbols are the same as defined in claim 1, or a pharmaceutically acceptable salt thereof, comprising:

(1) converting a compound of the formula [IV]:

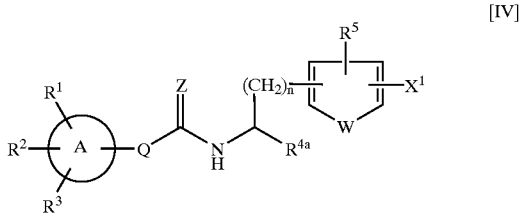

wherein $X^1$ is a leaving group, $R^{4a}$ is an ester group, and other symbols are the same as defined above, to the corresponding organotin compound, (2) reacting the organotin compound with a compound of the formula [VIII]:

wherein X is a leaving group and $R^6$ is the same as defined above, (3) converting the ester group of the compound of the formula [Ia] into a carboxyl group, if desired, and (4) converting the carboxyl group of the resulting compound into an ester group, an amide group or a pharmaceutically acceptable salt thereof, if further desired.

39. N-(2,6-dichlorobenzoyl)-4-(2,6-dimethoxyphenyl)-L-phenylalanine.

40. The method according to claim 34, wherein said epithelial lined tissues are selected from the group consisting of skin, urinary tract, respiratory airway, and joint synovium.

41. The method according to claim 35, wherein said inflammatory bowel disease is selected from the group consisting of ulcerative colitis and Crohn's disease.

42. A method for the treatment of a patient suffering from or susceptible to conditions caused by adhesion of a cell expressing an $\alpha_4$ integrin to MAdCAM-1 VCAM-1 or CS-1, which comprises administering to said patient an inhibitory amount of the compound as set forth in claim 1 or 11.

* * * * *